US007825297B2

(12) United States Patent
Shah et al.

(10) Patent No.: US 7,825,297 B2
(45) Date of Patent: Nov. 2, 2010

(54) EXPRESSION OF ANTIFUNGAL PLANT PROTEINS IN TRANSGENIC PLANTS

(75) Inventors: Dilip Maganlal Shah, Chesterfield, MO (US); Anita Kay Snyder, St. Louis, MO (US)

(73) Assignee: Donald Danforth Plant Science Center, St. Louis, MO (US)

( * ) Notice: Subject to any disclaimer, the term of this patent is extended or adjusted under 35 U.S.C. 154(b) by 0 days.

(21) Appl. No.: 11/961,810

(22) Filed: Dec. 20, 2007

(65) Prior Publication Data

US 2008/0201800 A1    Aug. 21, 2008

Related U.S. Application Data

(60) Provisional application No. 60/871,682, filed on Dec. 22, 2006.

(51) Int. Cl.
*C12N 15/09* (2006.01)
*C12N 15/82* (2006.01)
*A01H 5/00* (2006.01)

(52) U.S. Cl. .................. 800/301; 800/278; 800/279; 800/298; 800/320; 800/317; 435/468; 435/419; 435/418

(58) Field of Classification Search .................. None
See application file for complete search history.

(56) References Cited

U.S. PATENT DOCUMENTS

| 5,538,525 A | 7/1996 | Broekaert et al. |
| 5,689,052 A | 11/1997 | Brown et al. |
| 6,911,577 B2 | 6/2005 | Simmons et al. |
| 6,916,970 B2 | 7/2005 | Liang et al. |

FOREIGN PATENT DOCUMENTS

| AR | 064503 | 4/2009 |
| EP | 0392225 | 10/1990 |
| WO | 2008080014 | 7/2008 |

OTHER PUBLICATIONS

Cote et al . Accession No. BE942125; deposited Oct. 3, 2009.*
VandenBosch et al. Accession No. BF003550; Deposited Oct. 6, 2000.*
Bowles, "Defense-Related Proteins in Higher Plants", Annu. Rev. Biochem, 1990; pp. 873-907; vol. 59.
Brears et al., "Genetic Engineering for Disease Resistance in Plants", CIBA Agricultural Biotechnology, 1994; pp. 10-13.
Broekaert et al., "Antimicrobial Peptides From Plants", Critical Reviews in Plant Sciences, 1997; pp. 297-323; vol. 16.
Broekaert et al., "Plant Defensins: Novel Antimicrobial Peptides as Components of the Host Defense System", Plant Physiol, 1995; pp. 1353-1358; vol. 108.
Broekaert et al., "An Automated Quantitative Assay for Fungal Growth Inhibition", FEMS Microbiology Letters, 1990; pp. 55-60; vol. 69.
Da Silva Conceicao et al., "Plant Defensins In Pathogenesis-related Proteins in Plants", S. Muthukrishnan, ed, 1999; pp. 247-260; New York: CRC Press.
Gao et al., "Fungal Pathogen Protection in Potato by Expression of a Plant Defensin Peptide", Nature Biotechnology, 2000; pp. 1307-1310; vol. 18.
Hammond-Kosack et al., "Plant Pathogens: How Can Molecular Genetic Information on Plant Pathogens Assist in Breeding Disease Resistant Crops", Proceedings of the 4th International Crop Science Congress, Sep. 26-Oct. 1, 2004, pp. 1-18, Brisbane, Australia.
Hanks et al., "Defensin Gene Family in Medicago Truncatula: Structure, Expression and Induction by Signal Molecules", Plant Mol Biol, 2005; pp. 385-399; vol. 58.
International Search Report for PCT/US2007/088442 dated Oct. 7, 2008.
Lay et al., "Defensins-Components of the Innate Immune System in Plants", Current Protein Peptide Science, 2005, pp. 85-101, vol. 6.
Spelbrink et al., "Differential Antifungal and Calcium Channel-Blocking Activity among Structurally Related Plant Defensins", Plant Physiol, Aug. 2004; pp. 2055-2067; vol. 135.
Terras et al., "Analysis of Two Novel Classes of Plant Antifungal Proteins from Radish (*Raphanus sativus* L.) Seeds", J Biol Chem, 1992. pp. 15301-15309, vol. 267 No. 22.
Thevissen et al., "Defensins from Insects and Plants Interact with Fungal Glucosylceramides", J Biol Chem, 2004, pp. 3900-3905, vol. 279 No. 6.
Thevissen et al., "Fungal Membrane Responses Induced by Plant Defensins and Thionins", J Biol Chem, 1996 pp. 15018-15025 vol. 271 No. 25.
Thevissen et al., "Fungal sphingolipids as targets for the development of selective antifungal therapeutics", Curr Drug Targets, 2005; pp. 923-928; vol. 6.
Thomma et al., "Plant Defensins", Planta, 2002, pp. 193-202, vol. 216.
Wesley et al., "Construct Design for Efficient, Effective and High-Throughput Gene Silencing in Plants", The Plant Journal, 2001, pp. 581-590, vol. 27(6).
Almeida et al., "Solution Structure of Pisum Sativum Defensin 1 by High Resolution NMR: Plant Defensins, Identical Backbone with Different Mechanisms of Action", J Mol Biology, 2002, pp. 749-757; vol. 315.
Chen et al., "Characterization of Arabidopsis Thaliana-Fusarium Graminearum Interactions and Identification of Variation in Resistance Among Ecotypes", Molecular Plant Pathology, 2006, pp. 391-403, vol. 7(5).

(Continued)

*Primary Examiner*—Medina A Ibrahim
(74) *Attorney, Agent, or Firm*—Thompson Coburn LLP; Charles P. Romano

(57) ABSTRACT

DNA constructs that provide for production of potent antifungal proteins in transgenic plants and transformed yeast cells are described. Methods of using the DNA constructs to produce transgenic plants that inhibit growth of plant pathogenic fungi are also disclosed. The use of transformed yeast cells containing the DNA constructs to produce the antifungal proteins and methods of isolating the antifungal proteins are also described.

25 Claims, 16 Drawing Sheets

OTHER PUBLICATIONS

Makandar et al., "Genetically Engineered Resistance to Fusarium Head Blight in Wheat by Expression of Arabidopsis NPR1", MPMI, 2006, pp. 123-129, vol. 19, No. 2.

Urban et al., "Arabidopsis is Susceptible to the Cereal Ear Blight Fungal Pathogens Fusarium Graminearum and Fusarium Culmorum", The Plant Journal, 2002, pp. 961-973, vol. 32.

Choi et al., "Expression of BrD1, a Plant Defensin from Brassica Rapa, Confers Resistance against Brown Planthopper (*Nilaparvata lugens*) in Transgenic Rices", Molecules and Cells, Aug. 31, 2009, pp. 131-137, vol. 28.

Osborn et al., "Isolation and Characterisation of Plant Defensins from Seeds of *Asteraceae, Fabaceae, Hippocastanaceae* and *Saxifragaceae*", FEBS Letters, 1995, pp. 257-262, vol. 368.

* cited by examiner

```
ACCESSION                                                                          SEQ ID NO NUMBER
            1                                                                80
AJ497738  (1) ------------------------MVAEARTCESQSHKFKGPCASDHNCASVCQTERFSGGHCRGFRRRCFCTTHC- SEQ ID NO:1
AW559768  (1) ----ARSVPLVSTISXFLLHLVATGPSMVAEARTCESQSHKFKGPCASDHNCASVCQTERFSGGHCRGFRRRCFCTTHC- SEQ ID NO:2
BQ152800  (1) ---------------------------TCESQSHKFKGPCASDHNCASVCQTERFSGGHCRGFRXRCFCTTHC- SEQ ID NO:3
AJ498514  (1) ----------------------PSMVAEARTCESQSHKFKGPCASDHNCASVCQTERFSGGHCRGFRRRCFCTTHC- SEQ ID NO:4
AL385796  (1) ---MARSVFLVSTIFVFLLVLVATGPSMVAEARTCESQSHKFKGPCASDHNCASVCQTERFSGGHCRGFRRRCFCTTHC- SEQ ID NO:5
CA990100  (1) -----------------------------------------SDHNCASVCQTERFSGGHCRGFRRRCFCTTHC- SEQ ID NO:6
AW573770  (1) ---MARSVSLVFTIFVFLLLVVATGPSMVAEARTCESQSHKFKGPCASDHNCASVCQTERFSGGHCRGFRRRCFCTTHC- SEQ ID NO:7
BQ151713  (1) -------------------------------------------------RFSGGHCRGFRRRCFCTTHC- SEQ ID NO:8
BE943479  (1) ----------STIFVFLLFLVATGPSVVAEARTCESQSHKFKGPCASDHNCASVCQTERFSGGHCRGFRRRCFCTTHC- SEQ ID NO:9
BG583978  (1) -----------------------------------------NCASVCQTERFSGGHCRGFRRRCFCTTHC- SEQ ID NO:10
BG589141  (1) -------------------------MVAEARTCESQSHKFKGPCANDHNCASVCQTERFSGGHCRGFRRRCFCTTHW- SEQ ID NO:11
BI310743  (1) ---MGSFSSFGFTIFVFLLLLVATGPSMVAEARTCESQSHKFKGPCASDHNCASVCQTERFSGGHCRGFRRRCFCTTHC- SEQ ID NO:12
BI269012  (1) ----------------------------SHKFKGPCASDHNCASVCQTERFSGGHCRGFRRRCFCTTHC- SEQ ID NO:13
BG452606  (1) -------------------------MVAEARTCESQSHKFKGPCASDHNCASVCQTERFSGGHCRGFRRRCFCTTHC- SEQ ID NO:14
AL381562  (1) ---------------VFLLLLLVATGPSMVAEARTCESQSHKFKGPCASDHNCASVCQTERFSGGHCRGFRRRCFCTTHC- SEQ ID NO:15
BE942125  (1) ---------LVSTIFVFLLLLVATGPSMVAEARTCESQSHKFKGPCASDHNCASVCQTERFSGGHCRGFRRRCFCTTHC- SEQ ID NO:16
BG455536  (1) --------TSLVSTIFVFLLLLVATGPSMVAEARTCESQSHKFKGPCASDHNCASVCQTERFSGGHCRGFRRRCFCTTHC- SEQ ID NO:17
BQ157926  (1) -------GTSLVSTIFVFLLLLVATGPSMVAEARTCESQSHKFKGPCASDHNCASVCQTERFSGGHCRGFRRRCFCTTHC- SEQ ID NO:18
BI263488  (1) --------TSLVSTIFVFLLLLVATGPSMVAEARTCESQSHKFKGPCASDHNCASVCQTERFSGGHCRGFRRRCFCTTHC- SEQ ID NO:19
BG457444  (1) --------HQVSTIFVFLLLLVATGPSMVAEARTCESQSHKFKGPCASDHNCASVCQTERFSGGHCRGFRRRCFCTTHC- SEQ ID NO:20
BG582065  (1) -------------IFVFLLLLVATGPSMVAEARTCESQSHKFKGPCASDHNCASVCQTERFSGGHCRGFRRRCFCTTHC- SEQ ID NO:21
AW560708  (1) -------------------------MVAEARTCESQSHKFKGPCASDHNCASVCQTERFSGGHCRGFRRRCFCTTHC- SEQ ID NO:22
BQ144130  (1) ----------------------SMVAEARTCESQSHKFKGPCASDHNCASVCQTERFSGGHCRGFRRRCFCTTHC- SEQ ID NO:23
BG454920  (1) -------------------------MVAEARTCESQSHKFKGPCASDHNCASVCQTERFSGGHCRGFRRRCFCTTHC- SEQ ID NO:24
BM812997  (1) --------VPLVSTIFVFLLLLVATGPSMVAEARTCESQSHKFKGPCASDHNCASVCQTERFSGGHCRGFRRRCFCTTHC- SEQ ID NO:25
CX538973  (1) ------GSVPLVSTIFVFLLLLVATGPSMVAEARTCESQSHKFKGPCASDHNCASVCQTERFSGGHCRGFRRRCFCTTHC- SEQ ID NO:26
BF003550  (1) ---MARSVPLVSTIFVFLLLLVATG------------------------------------------------- SEQ ID NO:27
BF003550  (1) ---------------------GPSMVAEARTCESQSHKFKGPCASDHNCASVCQTERFSGGHCRGFRRRCFCTTHC- SEQ ID NO:28
BQ122363  (1) ----------------------GPSMVAEARTCESQSHKFKGPCASDHNCASVCQTERFSGGHCRGFRRRCFCTTHC- SEQ ID NO:29
BQ144201  (1) --------------------ATGPSMVAEARTCESQSHKFKGPCASDHNCASVCQTERFSGGHCRGFRRRCFCTTHC- SEQ ID NO:30
AL381563  (1) ---------------VFLLLLLVATGPSMVAEARTCESQSHKFKGPCASDHNCASVCQTERFSGGHCRGFRRRCFCTTHC- SEQ ID NO:31
CA918547  (1) ------SVPLVSTIFVFLLLLVATGPSMVAEARTCESQSHKFKGPCASDHNCASVCQTERFSGGHCRGFRRRCFCTTHC- SEQ ID NO:32
AL386553  (1) ---MARSVPLVSTIFVFLLLLVATGPSMVAEARTCESQSHKFKGPCASDHNCASVCQTERFFGGHCRGFRRRCFCTTHC- SEQ ID NO:33
BQ156240  (1) -------------------------------------------FVCQTERFFGGHXRGFRXXCFCTTHC- SEQ ID NO:34
BQ144143  (1) ----------------------------ARGDHNCASVCQTERFSGGH-------------- SEQ ID NO:35
BQ144143  (1) -----------------------------------------------CRGFRRRCFCTTHC- SEQ ID NO:36
BF634083  (1) ---------------------------------------------------------HC- SEQ ID NO:37
BI269582  (1) --------------------------------------QTERFFGGHCRGFRRRXCFCTTHC- SEQ ID NO:38
BQ155489  (1) --------------------ATGPSMVAXARTCESQSHKFKGPXXSDHNXXXVCQTERFFGGHCRGFRRXCFCTTHC- SEQ ID NO:39
BG455005  (1) -------------------------------------------------GFRRRCFCTTHC- SEQ ID NO:40
BQ156458  (1) ------------------LVAXGPSMVAEARTCESQSXKFKGPCXSDXNCAXVCQTERFFGGHXRGFRRRCFCTTHC- SEQ ID NO:41
BG454853  (1) -----------------------------------------------IPHEGGFRRRCFCTTHC- SEQ ID NO:42
BQ151713  (1) SARGARSVPLVSTIFVFLLLLVATGPSMVAEARTCESQSHKFKGPCASDHNCASVCQTL---------------- SEQ ID NO:43
BG583978  (1) ------------VFLLLLLVATGPSMVAEARTCESQSHKFKGPCASD--------------- SEQ ID NO:44
BG583286  (1) -------------FVLLLLLVATGPSMVAEARTCESQSHKFKGPCASDHNCASVCQ------------- SEQ ID NO:45
BE998785  (1) ----ARSVPLVSTIFVFLLLLVATGPSMVAEARTCESQSHKFKGPCASDHNCASVCQTERFSGGHCRGFRRRCFCTTHC- SEQ ID NO:46
AL386552  (1) ---MARSVPLVSTIFVFLLLLVATGPSMVAEARTCESQSHKFKGPCASDHNCASVCQTERFSGGHCRGFRRRCFCTTHC- SEQ ID NO:47
BQ152697  (1) ----ARSVPLVSTIFVFLLLLVATGPSMVAEARTCESQSHKFKGPCASDHNCASVCQTERFSGGHCRGFRRRCFCTTHC- SEQ ID NO:48
CX523737  (1) ----ARSVPLVSTIFVFLLLLVATGPSMVAEARTCESQSHKFKGPCASDHNCASVCQTERFSGGHCRGFRRRCFCTTHC- SEQ ID NO:49
CX538427  (1) ----ARSVPLVSTIFVFLLLLVATGPSMVAEARTCESQSHKFKGPCASDHNCASVCQTERFSGGHCRGFRRRCFCTTHC- SEQ ID NO:50
AL387540  (1) ---MARSVPLVSTIFVFLLLLVATGPSMVAEARTCESQSHKFKGPCASDHNCASVCQTERFSGGHCRGFRRRCFCTTHC- SEQ ID NO:51
AL387541  (1) ---MARSVPLVSTIFVFLLLLVATGPSMVAEARTCESQSHKFKGPCASDHNCASVCQTERFSGGHCRGFRRRCFCTTHC- SEQ ID NO:52
AW287924  (1) ---MARSVPLVSTIFVFLLLLVATGPSMVAEARTCESQSHKFKGPCASDHNCASVCQTERFSGGHCRGFRRRCFCTTHC- SEQ ID NO:53
BE941578  (1) ---MARSVPLVSTIFVFLLLLVATGPSMVAEARTCESQSHKFKGPCASDHNCASVCQTERFSGGHCRGFRRRCFCTTHC- SEQ ID NO:54
BF636345  (1) ---MARSVPLVSTIFVFLLLLVATGPSMVAEARTCESQSHKFKGPCASDHNCASVCQTERFSGGHCRGFRRRCFCTTHC- SEQ ID NO:55
BE999096  (1) ---MARSVPLVSTIFVFLLLLVATGPSMVGEARTCESQSHKFKGPCASDHNCASVCQTERFSGGHCRGFRRRCFCTTHC- SEQ ID NO:56
BG450117  (1) ---MARSVPLVSTIFVFLLLLVATGPSMVAEARTCESQSHKFKGPCASDHNCASVCQTERFSGGHCRGFRXRCFCTTHC- SEQ ID NO:57
BI263014  (1) ---MARSVPLVSTIFVFLLLLVATGPSMVAEARTCESQSHKFKGPCASDHNCASVCQTERFSGGHCRGFRRRCFCTTHC- SEQ ID NO:58
BI270683  (1) ---MARSVPLVSTIFVFLLLLVATGPSMVAEARTCESQSHKFKGPCASDHNCASVCQTERFSGGHCRGFRRRCFCTTHC- SEQ ID NO:59
BI310744  (1) ---MARSVPLVSTIFVFLLLLVATGPSMVAEARTCESQSHKFKGPCASDHNCASVCQTERFSGGHCRGFRRRCFCTTHC- SEQ ID NO:60
BQ144133  (1) ---MARSVPLVSTIFVFLLLLVATGPSMVAEARTCESQSHKFKGPCASDHNCASVCQTERFSGGHCRGFRRRCFCTTHC- SEQ ID NO:61
BQ145044  (1) ---MARSVPLVSTIFVFLLLLVATGPSMVAEARTCESQSHKFKGPCASDHNCASVCQTERFSGGHCRGFRRRCFCTTHC- SEQ ID NO:62
BQ153111  (1) ---MARSVPLVSTIFVFLLLLVATGPSMVAEARTCESQSHKFKGPCASDHNCASVCQTERFSGGHCRGFRRRCFCTTHC- SEQ ID NO:63
BQ154835  (1) ---MARSVPLVSTIFVFLLLLVATGPSMVAEARTCESQSHKFKGPCASDHNCASVCQTERFSGGHCRGFRRRCFCTTHC- SEQ ID NO:64
BQ157484  (1) ---MARSVPLVSTIFVFLLLLVATGPSMVAEARTCESQSHKFKGPCASDHNCASVCQTERFSGGHCRGFRRRCFCTTHC- SEQ ID NO:65
BQ157772  (1) ---MARSVPLVSTIFVFLLLLVATGPSMVAEARTCESQSHKFKGPCASDHNCASVCQTERFSGGHCRGFRRRCFCTTHC- SEQ ID NO:66
BQ159085  (1) ---MARSVPLVSTIFVFLLLLVATGPSMVAEARTCESQSHKFKGPCASDHNCASVCQTERFSGGHCRGFRRRCFCTTHC- SEQ ID NO:67
CX535058  (1) ---MARSVPLVSTIFVFLLLLVATGPSMVAEARTCESQSHKFKGPCASDHNCASVCQTERFSGGHCRGFRRRCFCTTHC- SEQ ID NO:68
BF633368  (1) ---MARSVPLVSTIFVFLLLLVATGPSMVAEARTCESQSHKFKGPCASDHNCASVCQTERFSGGHCRGFRRRCFCTTHC- SEQ ID NO:69
Consensus (1)    marsvplvstifvflllvatgpsmvaeaRTCESQSHKFKGPCASDHNCASVCQTERFSGGHCRGFRRRCFCTTHC- SEQ ID NO:70
Mature    (1)                             RTCESQSHKFKGPCASDHNCASVCQTERFSGGHCRGFRRRCFCTTHC- SEQ ID NO:71
```

Key: GenBank Accession Numbers for the corresponding nucleotide sequences of the ESTs encoding the deduced peptides are shown.

Figure 1.

```
      M   A   R   S   V   P   L   V   S   T   I   F   V   F   L   L   L   V
  1   CCATGGCTAGGTCCGTGCCACTCGTGTCCACCATCTTCGTGTTCCTCCTCCTCGTGG

A   T   G   P   S   M   V   A   E   A   R   T   C   E   S   Q   S   H   K   F
 61   CCACCGGCCCAAGCATGGTCGCCGAGGCCAGGACCTGCGAGTCCCAATCCCACAAGTTCA

K   G   P   C   A   S   D   H   N   C   A   S   V   C   Q   T   E   R   F   S
121   AGGGCCCATGCGCCAGCGACCACAACTGCGCCTCCGTGTGCCAAACCGAGCGCTTCTCCG

G   G   R   C   R   G   F   R   R   R   C   F   C   T   T   H   C   *
180   GCGGCAGGTGCAGGGGCTTCCGCAGGAGGTGCTTCTGCACCACCCACTGCTAATCTAGA
```

EXPRESSION OF ANTIFUNGAL PLANT PROTEINS IN TRANSGENIC PLANTS

CROSS REFERENCE TO RELATED APPLICATIONS

This application claims priority to the Dec. 22, 2006 filing date of U.S. Provisional Patent Application No. 60/871,682, which is herein incorporated by reference in its entirety.

TECHNICAL FIELD OF THE INVENTION

The present invention relates to antifungal polypeptides derived from plants, and methods for controlling pathogenic fungi employing the antifungal polypeptides. The antifungal polypeptides may be applied directly to a plant, applied to a plant in the form of microorganisms that produce the polypeptides, or the plants may be genetically modified to produce the polypeptides. The present invention also relates to DNA constructs, microorganisms and plants transformed with the DNA constructs, and compositions useful in controlling pathogenic plant fungi.

BACKGROUND

Protection of agriculturally important crops from pathogenic fungi is crucial in improving crop yields. Fungal infections are a particular problem in damp climates and may become a major concern during crop storage, where such infections can result in spoilage and contamination of food or feed products with fungal toxins. Unfortunately, modern growing methods, harvesting and storage systems can promote plant pathogen infections.

Control of plant pathogens is further complicated by the need to simultaneously control multiple fungi of distinct genera. For example, fungi such as *Alternaria; Ascochyta; Botrytis; Cercospora; Colletotrichum; Diplodia; Erysiphe; Fusarium; Gaeumanomyces; Helminthosporium; Macrophomina; Nectria; Peronospora; Phakopsora; Phoma; Phymatotrichum; Phytophthora; Plasmopara; Podosphaera; Puccinia; Pythium; Pyrenophora; Pyricularia; Rhizoctonia; Scerotium; Sclerotinia; Septoria; Thielaviopsis; Uncinula; Venturia;* and *Verticillium* species are all recognized plant pathogens. Consequently, resistant crop plant varieties or fungicides that control only a limited subset of fungal pathogens may fail to deliver adequate protection under conditions where multiple pathogens are present. It is further anticipated that plant pathogenic fungi may become resistant to existing fungicides and crop varieties, necessitating the introduction of fungal control agents with distinct modes of action to combat the resistant fungi.

One approach to inhibiting plant pathogenic activity has been to identify and isolate polypeptides and proteins exhibiting antifungal activity against plant pathogenic fungi (Bowles, 1990; Brears et al., 1994). The antifungal polypeptides and proteins that include chitinases, cysteine-rich chitin-binding proteins, β-1,3-glucanases, permatins (including zeamatins), thionins, ribosome-inactivating proteins, and non-specific lipid transfer proteins are believed to play important roles in plant defense against fungal infection. The use of these protein products to control plant pathogens in transgenic plants has been reported, for example, in European Patent Application 0 392 225.

Another group of proteins known as defensins have been shown to inhibit plant pathogens. Defensins are small cysteine-rich peptides of 45-54 amino acids that constitute an important component of the innate immunity of plants (Thomma et al., 2002; Lay and Anderson, 2005). Widely distributed in plants, defensins vary greatly in their amino acid composition. However, they all have a compact shape which is stabilized by either four or five intramolecular disulfide bonds. Plant defensins have been extensively studied for their role in plant defense. Some plant defensins inhibit the growth of a broad range of fungi at micromolar concentrations (Broekaert et al., 1995; Broekaert et al., 1997; da Silva Conceicao and Broekaert, 1999) and, when expressed in transgenic plants, confer strong resistance to fungal pathogens (da Silva Conceicao and Broekaert, 1999; Thomma et al., 2002; Lay and Anderson, 2005). Two small cysteine-rich proteins isolated from radish seed, Rs-AFP1 and Rs-AFP2, inhibited the growth of many pathogenic fungi when the pure protein was added to an in vitro antifungal assay medium (U.S. Pat. No. 5,538,525). Transgenic tobacco plants containing the gene encoding Rs-AFP2 protein were found to be more resistant to attack by fungi than non-transformed plants.

Antifungal defensin proteins have also been identified in Alfalfa (*Medicago sativa*) and shown to inhibit plant pathogens such as *Fusarium* and *Verticillium* in both in vitro tests and in transgenic plants (U.S. Pat. No. 6,916,970). Under low salt in vitro assay conditions, the Alfalfa defensin AlfAFP1 inhibited *Fusarium culmorum* growth by 50% at 1 ug/ml and *Verticillium dahliae* growth by 50% at 4 ug/ml (i.e. $IC_{50}$ values of 1 ug/ml and 4 ug/ml, respectively). Expression of the AlfAFP1 protein in transgenic potato plants was also shown to confer resistance to *Verticillium dahliae* in both greenhouse and field tests (Gao et al, 2000). Mode-of-action analyses have also shown that AlfAFP1 (which is alternatively referred to as MsDef1, for *Medicago sativa* Defensin 1) induces hyper-branching of *F. graminearum* and can block L-type calcium channels (Spelbrink et al, 2004).

Other defensin genes have also been identified in the legume *Medicago truncatula* (Hanks et al, 2005). The cloned MtDef2 protein has been demonstrated through in vitro experiments to have little or no antifungal activity (Spelbrink et al, 2004). Analysis of the sequence database search identified 10 tentative consensus sequences (10 unique defensin-encoding genes represented by multiple ESTs) and six singletons (i.e. six unique defensin genes represented by a single EST) with homology to known *Medicago* defensin genes. One of the tentative consensus sequences was identified as TC85327 and shown to be expressed in both mock-treated and mycorrhizal fungus-infected *Medicago truncatula* roots. There was no demonstration that proteins encoded by any of the TC85327 *Medicago truncatula* sequences possessed antifungal activity in this study (Hanks et al, 2005).

Although defensin proteins such as AlfAFP1 (MsDef1) and Rs-AFP2 have been used to obtain transgenic plants that are resistant to fungal infections, other proteins that provide for increased levels of resistance are needed. In particular, proteins with increased specific activities against fungal pathogens would be particularly useful in improving the levels of fungal resistance obtained in transgenic plants. Furthermore, proteins that inhibit fungal pathogens via distinct modes of action would also be useful in combating fungal pathogens that have become resistant to defensin proteins such as AlfAFP1 (MsDef1) and Rs-AFP2.

SUMMARY

The instant invention first provides for isolated DNA constructs useful for expressing MtDef4 antifungal proteins. The isolated DNA constructs comprise a heterologous promoter, a sequence that encodes a MtDef4 polypeptide with at least 85% sequence identity to SEQ ID NO:112, and a polyadenylation sequence, wherein the promoter, the sequence encoding a signal peptide, the sequence encoding a mature MtDef4 polypeptide and the polyadenylation sequence are operably linked.

Isolated DNA constructs of the invention can further comprise a sequence that encodes a signal peptide that is operably linked to the sequence that encodes the MtDef4 polypeptide. The signal peptides used in DNA constructs of the invention are selected from the group consisting of yeast signal peptides, monocot plant signal peptides, dicot plant signal peptides, and synthetic signal peptides. Yeast signal peptides can be selected from the group consisting of an α-factor signal peptide, an invertase signal peptide, and a PHO1 signal peptide. Dicot plant signal peptides can be selected from the group consisting of a MtDef1.1, a MsDef1.6, a MtDef2.1, a MtDef4 and a tobacco PR1b signal peptide. Monocot plant signal peptides can be selected from the group consisting of a cysteine endoproteinase signal peptide and an α-amylase signal peptide. The MtDef4 signal peptides can be selected from a group consisting of SEQ ID NO:117, SEQ ID NO:118, SEQ ID NO:119, SEQ ID NO:120, SEQ ID NO:121. SEQ ID NO:122, and SEQ ID NO:123 signal peptide sequences.

A variety of DNA sequences encoding distinct MtDef4 polypeptides can be used in the DNA constructs of the instant invention. In general, a sequence that encodes a MtDef4 polypeptide with at least 85% sequence identity to SEQ ID NO:112 is used. The encoded MtDef4 polypeptide sequences of the DNA construct include, but are not limited to, sequences that encode mature MtDef4 proteins. Mature MtDef4 proteins encoded by these sequences can be selected from the group of polypeptide sequences consisting of an MtDef4 consensus sequence (SEQ ID NO: 71), amino acids 30-76 of AL386553 (SEQ ID NO:105), MtDef4.1 (SEQ ID NO:112), MtDef4.2 (SEQ ID NO:114), MtDef4.3 (SEQ ID NO:116), MtDef4.1 (H33R) (SEQ ID NO:125), MtDef4.1 (H33R, C3S, C47S) (SEQ ID NO:135), MtDef4.1 (H33R, C14S, C34S) (SEQ ID NO:136), MtDef4.1 (H33R, C20S, C41S) (SEQ ID NO:137), and MtDef4.1 (H33R, C24S, C43S) (SEQ ID NO:138). The encoded MtDef4 polypeptide sequences of the DNA construct also include sequences that encode MtDef4 proproteins comprising a MtDef4 signal peptide and a mature MtDef4 protein. MtDef4 proprotein polypeptide sequences include, but are not limited to, an MtDef4 proprotein consensus sequence (SEQ ID NO: 99), unique MtDef4 proproteins such as AL385796 (SEQ ID NO:77), AW573770 (SEQ ID NO:78), AL386553 (SEQ ID NO:80), AL386552 (SEQ ID NO:81), BE999096 (SEQ ID NO:87), MtDef4.1 proprotein sequences (SEQ ID NO:111), MtDef4.2 proprotein sequences (SEQ ID NO:113), MtDef4.3 proprotein sequences (SEQ ID NO:115), a MtDef4.1 (H33R) proprotein sequence (SEQ ID NO:151), polypeptides that have at least 70% sequence identity to these sequences, and the biological functional equivalents of these sequences. The MtDef4 polypeptide encoded by the DNA construct can thus comprise an amino acid sequence selected from the group consisting of a MtDef4 consensus sequence (SEQ ID NO: 71), amino acids 30-76 of AL386553 (SEQ ID NO:105), a mature MtDef4.1 sequence (SEQ ID NO:112), a mature MtDef4.2 (SEQ ID NO:114) sequence, a mature MtDef4.3 (SEQ ID NO:116), a mature MtDef4.1 (H33R) sequence (SEQ ID NO:125), a mature MtDef4.1 (H33R, C3S, C47S) sequence (SEQ ID NO:135), a mature MtDef4.1 (H33R, C14S, C34S) sequence (SEQ ID NO:136), a mature MtDef4.1 (H33R, C20S, C41S) sequence (SEQ ID NO:137), a mature MtDef4.1 (H33R, C24S, C43S) sequence (SEQ ID NO:138), a MtDef4 proprotein consensus sequence (SEQ ID NO: 99), a MtDef4 proprotein sequence AL385796 (SEQ ID NO:77), AW573770 (SEQ ID NO:78), BI310743 (SEQ ID NO:79), AL386553 (SEQ ID NO:80), AL386552 (SEQ ID NO:81), BE999096 (SEQ ID NO:87), a MtDef4.1 proprotein sequence (SEQ ID NO:111), a MtDef4.2 proprotein sequence (SEQ ID NO:113), MtDef4.3 proprotein sequence (SEQ ID NO:115), and a MtDef4.1 (H33R) proprotein sequence (SEQ ID NO:151).

A DNA sequence that encodes a MtDef4 polypeptide is contained within a sequence that can be selected from the group consisting of a MtDef4.1 (H33R) coding sequence (SEQ ID NO:144), a synthetic MtDef4.1 (H33R) gene (SEQ ID NO:72), AL386552 (SEQ ID NO: 100), AL385796 (SEQ ID NO:101), AL386553 (SEQ ID NO:102), AW573770 (SEQ ID NO: 103), BE999096 (SEQ ID NO:104), a MtDef4.1 genomic clone (SEQ ID NO:108), a MtDef4.2 genomic clone (SEQ ID NO:109), a MtDef4.3 genomic clone (SEQ ID NO:110), a MtDef4.2 deduced coding sequence (SEQ ID NO:124), a MtDef4.1 deduced coding sequence (SEQ ID NO:126), a MtDef4 TC94214 consensus sequence (SEQ ID NO:141), a MsDef4.1 cDNA sequence (SEQ ID NO:142), a MtDef4.3 deduced coding sequence (SEQ ID NO:143), a mature MtDef4.1 (H33R, C3S, C47S) coding sequence (SEQ ID NO:146), a mature MtDef4.1 (H33R, C14S, C34S) coding sequence (SEQ ID NO:147), a mature MtDef4.1 (H33R, C20S, C41S) coding sequence (SEQ ID NO:148) and a mature MtDef4.1 (H33R, C24S, C43S) coding sequence (SEQ ID NO:149).

In certain embodiments of the invention, the isolated DNA construct uses promoter and polyadenylation sequences that provide for expression of operably linked sequences when introduced into a transgenic plant. Sequences encoding MtDef4 polypeptides that are at least 85% identical to SEQ ID NO:112 are operably linked to the promoter and polyadenylation sequences that provide for expression in transgenic plants. The promoter that provides for expression in plants can be selected from the group consisting of a constitutive promoter, a tissue specific promoter, a stress induced promoter, and a fungal infection induced promoter. Constitutive promoters are selected from the group consisting of a CaMV35S promoter, a FMV35S promoter, a maize ubiquitin promoter, and a rice actin promoter. Polyadenylation sequences can be selected from the group consisting of a CaMV35S, a NOS, a rice lactate dehydrogenase, and a wheat Hsp17 polyadenylation sequence.

In other embodiments of the invention, the isolated DNA construct can further comprise an intron sequence that provides for expression of operably linked sequences when introduced into the nuclear genome of a plant and when the intron sequence is operably linked to the promoter, the sequence that encodes a signal peptide, the sequence that encodes a mature MtDef4 polypeptide, and the polyadenylation sequence. This intron sequence can be selected from the group comprising a rice actin intron, a maize hsp70 intron, a maize small subunit RUBISCO intron, a maize ubiquitin intron, a maizeAdh1 intron, a rice phenylalanine ammonia lyase intron, a sucrose synthase intron, a CAT-1 intron, a pKANNIBAL intron, the PIV2 intron and a Super Ubiquitin intron.

The DNA construct that provides for expression of a mature MtDef4 protein in plants can comprise a polynucleotide containing a maize ubiquitin promoter and intron, a synthetic MtDef4.1 (H33R) gene encoding both an MtDef4 signal peptide and mature MtDef4 protein and polyadenylation signal. Another DNA construct that provides for expression of a mature MtDef4 protein in plants can comprise a FMV promoter, a super ubiquitin intron, a genomic MtDef4.1 sequence encoding a signal peptide, an intron and a mature MtDef4 protein, and a tNOS terminator. DNA constructs that provide for MtDef4 protein expression in plants can further comprise sequences encoding vacuolar targeting or endoplasmic reticulum retention peptides that are operably linked to the MtDef4 polypeptide are also contemplated by this invention. A DNA construct that provides for expression of a mature MtDef4 protein in plants can comprise a FMV promoter, a super ubiquitin intron, a genomic MtDef4.1 sequence encoding a signal peptide, an intron and a mature MtDef4 protein that is operably linked to a vacuolar or endoplasmic reticulum targeting peptide, and a tNOS terminator. Examples of DNA constructs for expression of MtDef4 proteins in plants include SEQ ID NO:74, SEQ ID NO:75, SEQ ID NO:76, and SEQ ID NO:150.

The DNA constructs of the invention can further comprise a sequence encoding a selectable marker. This selectable marker is typically used to select transgenic plants containing the DNA construct. The selectable marker can be selected from the group consisting of a neomycin phosphotransferase protein, a phosphinothricin acetyltransferase protein, a glyphosate resistant 5-enol-pyruvylshikimate-3-phosphate synthase (EPSPS) protein, a hygromycin phosphotransferase protein, a dihydropteroate synthase protein, a sulfonylurea insensitive acetolactate synthase protein, an atrazine insensitive Q protein, a nitrilase protein capable of degrading bromoxynil, a dehalogenase protein capable of degrading dalapon, a 2,4-dichlorophenoxyacetate monooxygenase protein, a methotrexate insensitive dihydrofolate reductase protein, and an aminoethylcysteine insensitive octopine synthase protein.

The DNA constructs of the invention can further comprise a sequence encoding a scoreable marker. This scoreable marker is typically used to identify transgenic plants containing the DNA construct. The scoreable marker can be selected from the group consisting of a beta-glucuronidase protein, a green fluorescent protein, a yellow fluorescent protein, a beta-galactosidase protein, a luciferase protein derived from a luc gene, a luciferase protein derived from a lux gene, a sialidase protein, streptomycin phosphotransferase protein, a nopaline synthase protein, an octopine synthase protein and a chloramphenicol acetyl transferase protein.

Transgenic plants comprising the aforementioned DNA constructs that express MtDef4 polypeptides in such plants are also provided by this invention. The transgenic plant can be a monocot plant or a dicot plant. Transgenic monocot plants of the invention can be selected from the group consisting of barley, corn, flax, oat, rice, rye, sorghum, turf grass, sugarcane, and wheat. Transgenic dicot plants of the invention can be selected from the group consisting of alfalfa, *Arabidopsis*, barrel medic, banana, broccoli, bean, cabbage, canola, carrot, cassava, cauliflower, celery, citrus, cotton, a cucurbit, eucalyptus, garlic, grape, onion, lettuce, pea, peanut, pepper, potato, poplar, pine, sunflower, safflower, soybean, strawberry, sugar beet, sweet potato, tobacco, and tomato.

In other embodiments of the invention, the DNA construct uses a promoter and a polyadenylation sequence that provide for expression of operably linked sequences when introduced into a yeast cell. This promoter can be selected from the group consisting of an AOX1 promoter, an AOX2 promoter, a PHO promoter, a MOX promoter, a DAS promoter, an ADH promoter, a GAPDH promoter, and a LAC4 promoter. This polyadenylation sequence can selected from the group consisting of an AOX1, an AOX2, a CYC1, a p40, a p76, a MOX, a LAC4, and an actin polyadenylation sequence. The DNA construct can comprise a polynucleotide encoding an operably linked AOX1 promoter, yeast α-factor signal sequence, mature MtDef4.1 (H33R) defensin sequence, and an AOX1 polyadenylation sequence. Alternatively, the DNA construct can comprise a polynucleotide encoding an operably linked AOX1 promoter, yeast α-factor signal sequence, mature MtDef4.1 defensin sequence, and an AOX1 polyadenylation sequence. Examples of DNA constructs for expression of mature MtDef4 proteins in yeast include SEQ ID NO:73 or SEQ ID NO:157.

DNA constructs for expression of mature MtDef4 proteins in yeast can further comprise a selectable or scoreable marker gene. The selectable marker gene can be selected from the group consisting of genes encoding a ADE protein, a HIS5 protein, a HIS4 protein, a LEU2 protein, a URA3 protein, ARG4 protein, a TRP1 protein, a LYS2 protein, a protein conferring resistance to a bleomycin or phleomycins antibiotic, a protein conferring resistance to chloramphenicol, a protein conferring resistance to G418 or geneticin, a protein conferring resistance to hygromycin, a protein conferring resistance to methotrexate, an a ARO4-OFP protein, and a FZF1-4 protein.

The scoreable marker gene can be selected from the group consisting of genes encoding a beta-glucuronidase protein, a green fluorescent protein, a yellow fluorescent protein, a beta-galactosidase protein, a luciferase protein derived from a luc gene, a luciferase protein derived from a lux gene, a sialidase protein, streptomycin phosphotransferase protein, a nopaline synthase protein, an octopine synthase protein and a chloramphenicol acetyl transferase protein.

Yeast cells comprising the aforementioned DNA constructs that comprise a promoter and a polyadenylation sequence that provide for expression of operably linked sequences encoding MtDef4 proteins in yeast are also provided by this invention. The yeast cells can be selected from the group consisting of *Candida, Kluveromyces, Hansuela, Pichia, Saccharomyces, Schizosaccharomyces*, and *Yarrowia*.

The instant invention further provides for methods of obtaining transgenic plants capable of inhibiting growth of a plant pathogenic fungus. These methods comprise the steps of: introducing the DNA construct that provides for expression of a MtDef4 polypeptide in a plant, a plant cell or a plant tissue and obtaining a transgenic plant comprising this DNA construct that expresses a plant pathogenic fungus inhibitory amount of a MtDef4 polypeptide. The transgenic plant obtained by this method can be a monocot plant or a dicot plant. Transgenic monocot plants of the invention can be selected from the group consisting of barley, corn, flax, oat, rice, rye, sorghum, turf grass, sugarcane, and wheat. Transgenic dicot plants of the invention can be selected from the group consisting of alfalfa, *Arabidopsis*, barrel medic, banana, broccoli, bean, cabbage, canola, carrot, cassava, cauliflower, celery, citrus, cotton, a cucurbit, eucalyptus, garlic, grape, onion, lettuce, pea, peanut, pepper, potato, poplar, pine, sunflower, safflower, soybean, strawberry, sugar beet, sweet potato, tobacco, and tomato. To practice this method, the DNA construct can be introduced into said plant in step (a) by a method selected from the group consisting of particle bombardment, DNA transfection, DNA electroporation and T-DNA mediated transformation.

The DNA construct used in certain embodiments of this method can further comprise a selectable marker gene. When the DNA construct further comprises a selectable marker gene, a transgenic plant of the invention is obtained by growing said plant, plant cell, or plant tissue under conditions requiring expression of the selectable marker gene for plant growth. This selectable marker gene can be selected from the group consisting of genes encoding a neomycin phosphotransferase protein, a phosphinothricin acetyltransferase protein, a glyphosate resistant 5-enol-pyruvylshikimate-3-phosphate synthase (EPSPS) protein, a hygromycin phosphotransferase protein, a dihydropteroate synthase protein, a sulfonylurea insensitive acetolactate synthase protein, an atrazine insensitive Q protein, a nitrilase protein capable of degrading bromoxynil, a dehalogenase protein capable of degrading dalapon, a 2,4-dichlorophenoxyacetate monoxygenase protein, a methotrexate insensitive dihydrofolate reductase protein, and an aminoethylcysteine insensitive octopine synthase protein.

These methods of obtaining transgenic plants can also employ DNA constructs that further comprise a scoreable marker gene that functions in plants. In this case, expression of the scoreable marker gene is assayed to obtain a transgenic plant cell or a regenerated transgenic plant. Scoreable marker genes can be selected from the group consisting of genes encoding a beta-glucuronidase protein, a green fluorescent protein, a yellow fluorescent protein, a beta-galactosidase protein, a luciferase protein derived from a luc gene, a luciferase protein derived from a lux gene, a sialidase protein, streptomycin phosphotransferase protein, a nopaline synthase protein, an octopine synthase protein and a chloramphenicol acetyl transferase protein.

In this method, a transgenic plant that expresses a plant pathogenic fungus inhibitory amount of said mature MtDef4 polypeptide can be obtained by assaying expression of a MtDef4 encoding transgene in said transgenic plant. Expression of said MtDef4 encoding transgene can be assayed by a method selected from the group consisting of an immunoassay, an enzyme-linked immunoassay, an assay based on detection by RNA hybridization, and an assay based on detection by a reverse-transcriptase polymerase chain reaction. Alternatively, the expression of said MtDef4 encoding transgene is assayed by exposing said transgenic plant to a plant pathogenic fungus and determining if growth of said plant pathogenic fungus is inhibited. A plant pathogenic fungus inhibitory amount of mature MtDef4 polypeptide is at least 0.05 PPM, 0.5 PPM, 1.0 PPM, or 2.0 PPM, where PPM are "parts per million" of MtDef4 protein present in fresh weight plant tissue. Typically, microgram amounts of MtDef4 protein are present per gram fresh weight of transgenic plant tissue. In preferred embodiments, the plant pathogenic fungus inhibitory amount of MtDef4 protein is at least 0.5 PPM. In more preferred embodiments, the plant pathogenic fungus inhibitory amount of MtDef4 is at least 1.0 PPM. In the most preferred embodiments, the plant pathogenic fungus inhibitory amount of MtDef4 is at least 2.0 PPM.

This method provides for inhibition of the growth of a variety of plant pathogenic fungi. The plant pathogenic fungus inhibited by the method can be from the group consisting of an *Alternaria* sp., an *Ascochyta* sp., a *Botrytis* sp.; a *Cercospora* sp., a *Colletotrichum* sp., a *Diplodia* sp., an *Erysiphe* sp., a *Fusarium* sp., *Gaeumanomyces* sp., *Helminthosporium* sp., *Macrophomina* sp., a *Nectria* sp., a *Peronospora* sp., a *Phakopsora* sp., a *Phoma* sp., a *Phymatotrichum* sp., a *Phytophthora* sp., a *Plasmopara* sp., a *Puccinia* sp., a *Podosphaera* sp., a *Pyrenophora* sp., a *Pyricularia* sp, a *Pythium* sp., a *Rhizoctonia* sp., a *Scerotium* sp., a *Sclerotinia* sp., a *Septoria* sp., a *Thielaviopsis* sp., an *Uncinula* sp, a *Venturia* sp., and a *Verticillium* sp.

This invention also provides for transgenic plants capable of inhibiting the growth of a plant pathogenic fungus that are produced by the methods described herein. Transgenic plants produced by a process comprising the steps of introducing a DNA construct of the invention into a plant, a plant cell or a plant tissue and obtaining a transgenic plant comprising said DNA construct that expresses a plant pathogenic fungus inhibitory amount of a MtDef4 polypeptide are also thus contemplated by this invention. The transgenic plant obtained by this method can be a monocot plant or a dicot plant. Transgenic monocot plants of the invention can be selected from the group consisting of barley, corn, flax, oat, rice, rye, sorghum, turf grass, sugarcane, and wheat. Transgenic dicot plants of the invention can be selected from the group consisting of alfalfa, *Arabidopsis*, barrel medic, banana, broccoli, bean, cabbage, canola, carrot, cassava, cauliflower, celery, citrus, cotton, a cucurbit, eucalyptus, garlic, grape, onion, lettuce, pea, peanut, pepper, potato, poplar, pine, sunflower, safflower, soybean, strawberry, sugar beet, sweet potato, tobacco, and tomato. A plant pathogenic fungus inhibitory amount of mature MtDef4 polypeptide is at least 0.05 PPM, 0.5 PPM, 1.0 PPM, or 2.0 PPM, where PPM are "parts per million" of MtDef4 protein present in fresh weight plant tissue.

The instant invention further provides for methods of producing a MtDef4 polypeptide that has at least 85% sequence identity to the amino acid sequence as set forth in SEQ ID NO:112. The methods for producing the mature MtDef4 polypeptide comprise the steps of: culturing a yeast cell comprising a DNA construct that provides for expression of a MtDef4 polypeptide in yeast under conditions wherein said yeast cell expresses a MtDef4 polypeptide and isolating the MtDef4 polypeptide from the culture of the preceding step. The MtDef4 polypeptide can be isolated in the second step from the cell culture medium. Alternatively, the MtDef4 polypeptide can be isolated from the yeast cells. In certain embodiments of this method, the MtDef4 polypeptide is a mature MtDef4 protein. The yeast cell used in this method can be a *Pichia* cell that comprises a DNA construct containing an AOX1 promoter that is operably linked to a sequence encoding a signal peptide and a sequence encoding a mature MtDef4 polypeptide and the conditions that provide for expression of the mature MtDef4 protein would comprise culturing said *Pichia* cell in the presence of methanol.

The invention also provides for an antibody that recognizes a MtDef4 polypeptide with at least 85% sequence identity to SEQ ID NO:112. Kits for specifically detecting a MtDef4 polypeptide with at least 85% sequence identity to SEQ ID NO:112, comprising the antibody that recognizes a mature MtDef4 polypeptide with at least 85% sequence identity to SEQ ID NO:112 and a reagent for detecting said antibody, are also provided by this invention.

Certain isolated nucleotide sequences are also provided by this invention. The isolated nucleotide sequences of the invention comprise a synthetic MtDef4.1 (H33R) coding sequence (SEQ ID NO:72), MtDef4.2 genomic clone sequence (SEQ ID NO:109), an MtDef4.2 deduced coding sequence (SEQ ID NO:124), an MtDef4.3 genomic clone sequence (SEQ ID NO:110), an MtDef4.3 deduced coding sequence (SEQ ID NO:143), a mature MtDef4 (H33R, C3S, C47S) coding sequence (SEQ ID NO:146), a mature MtDef4.1 (H33R, C14S, C34S) coding sequence (SEQ ID NO:147), a mature MtDef4.1 (H33R, C20S, C41S) coding sequence (SEQ ID NO:148) and a mature MtDef4.1 (H33R, C24S, C43S) coding sequence (SEQ ID NO:149). Oligonucleotides derived from the above sequences are further contemplated. Such nucleotides may be used to identify transgenic plants containing these nucleotide sequences or to identify material obtained from these transgenic plants. Methods for using these oligonucleotides to identify the transgenic plant materials and kits for performing these methods are also contemplated.

Certain isolated peptide sequences are also provided by this invention. The isolated peptide sequences of the invention comprise a MtDef4.2 mature peptide sequence (SEQ ID NO:114), a MtDef4.3 mature peptide sequence (SEQ ID NO:116),), a MtDef4.1 (H33R, C3S, C47S) mature peptide sequence (SEQ ID NO:135), MtDef4.1 (H33R, C14S, C34S) mature peptide sequence (SEQ ID NO:136), a MtDef4.1 (H33R, C20S, C41S) mature peptide sequence (SEQ ID NO:137), or a MtDef4.1 (H33R, C24S, C43S) (SEQ ID NO:138) mature peptide sequence.

BRIEF DESCRIPTION OF THE DRAWINGS

The description refers to the accompanying drawings in which like references refer to like parts throughout the several views in which:

FIG. 1 shows an alignment of the MtDef4 EST deduced amino acid sequences and the derived MtDef4 consensus peptide sequence in TC94214. In the deduced MtDef4 pro-protein consensus sequence (SEQ ID NO: 70), amino acids comprising the deduced signal peptide sequence are in lower case and underlined, while the amino acids encoding the mature consensus MtDef4 protein are in upper case. The sense strand of the nucleotide sequence of the expressed sequence tag corresponding to SEQ ID NO:37 is provided in the sequence listing. The mature MtDef4 consensus sequence is also shown (SEQ ID NO:71).

DETAILED DESCRIPTION OF THE INVENTION

I. Definitions

Figure 2:
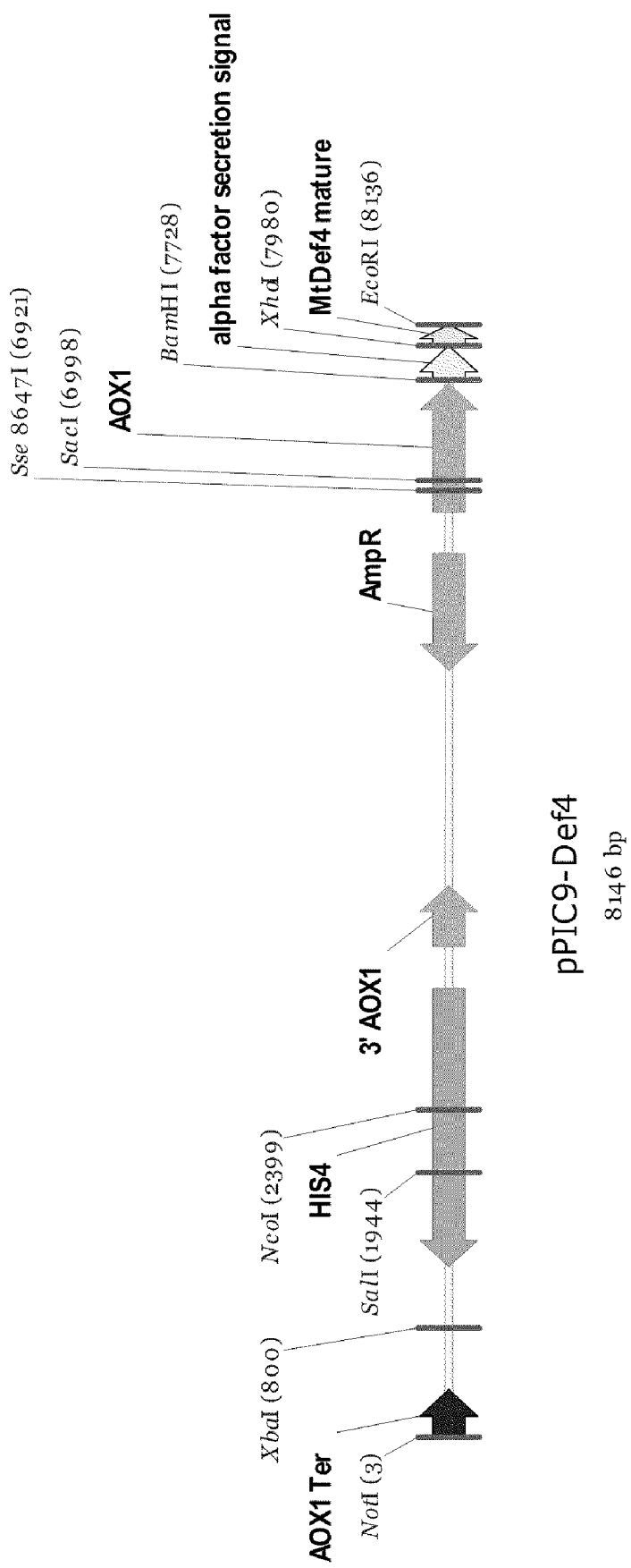
FIG. 2 shows a linear representation of the pPIC9 vector used to express various MtDef4 proteins. The sequence of the MtDef4 expression cassette comprising the AOX1 promoter, the yeast α-mating factor sequences that encode the signal peptide, pro-peptide and KEX2 cleavage site, the MtDef4.1 (H33R) gene, and AOX1 polyadenylation signal wherein all expression elements are operably linked is provided in SEQ ID NO: 73.

"Consensus sequence" refers to an amino acid, DNA or RNA sequence created by aligning two or more homologous sequences and deriving a new sequence that represents the common amino acid, DNA or RNA sequence.

The phrases "antifungal polypeptide" or "antifungal protein" as used herein refer to polypeptides or proteins which exhibit any one or more of the following characteristics of inhibiting the growth of fungal cells, killing fungal cells, disrupting or retarding stages of the fungal life cycle such as spore germination, sporulation, or mating, and/or disrupting fungal cell infection, penetration or spread within a plant.

The phrase "biological functional equivalents" as used herein refers to peptides, polypeptides and proteins that contain a sequence or structural feature similar to an MtDef4 protein of the present invention, and which exhibit the same or similar antifungal activity of an MtDef4 protein of the present invention. Biological functional equivalents also include peptides, polypeptides and proteins that react with (i.e. specifically bind) to monoclonal and/or polyclonal antibodies raised against an MtDef4 protein and that exhibit the same or similar antifungal activity as an MtDef4 protein.

The phrases "combating fungal damage", "combating or controlling fungal damage" or "controlling fungal damage" as used herein refer to reduction in damage to a crop plant or crop plant product due to infection by a fungal pathogen. More generally, these phrases refer to reduction in the adverse effects caused by the presence of an undesired fungus in the crop plant. Adverse effects of fungal growth are understood to include any type of plant tissue damage or necrosis, any type of plant yield reduction, any reduction in the value of the crop plant product, and/or production of undesirable fungal metabolites or fungal growth by-products including but not limited to mycotoxins.

The phrase "DNA construct" as used herein refers to any DNA molecule in which two or more ordinarily distinct DNA sequences have been covalently linked. Examples of DNA constructs include but not limited to plasmids, cosmids, viruses, BACs (bacterial artificial chromosome), YACs (yeast artificial chromosome), plant minichromosomes, autonomously replicating sequences, phage, or linear or circular single-stranded or double-stranded DNA sequences, derived from any source, that are capable of genomic integration or autonomous replication. DNA constructs can be assembled by a variety of methods including but not limited to recombinant DNA techniques, DNA synthesis techniques, PCR (Polymerase Chain Reaction) techniques, or any combination of techniques.

The phrase "a plant pathogenic fungus inhibitory amount", as used herein in the context of a transgenic plant expressing an MtDef4 polypeptide, refers to an amount of an MtDef4 polypeptide that results in any measurable decrease in fungal growth in the transgenic plant and/or any measurable decrease in the adverse effects caused by fungal growth in the transgenic plant.

The phrase "a heterologous promoter", as used herein in the context of a DNA construct, refers to either: i) a promoter that is derived from a source distinct from the operably linked structural gene or ii) a promoter derived the same source as the operably linked structural gene, where the promoter's sequence is modified from its original form.

The term "homolog" as used herein refers to a gene related to a second gene by identity of either the DNA sequences or the encoded protein sequences. Genes that are homologs can be genes separated by the event of speciation (see "ortholog"). Genes that are homologs may also be genes separated by the event of genetic duplication (see "paralog"). Homologs can be from the same or a different organism and may perform the same biological function in either the same or a different organism.

The phrases "MtDef4 polypeptide" or "MtDef4 protein" as used herein refer to: i) polypeptides or proteins with at least 70% sequence identity to a mature MtDef4 polypeptide or protein sequence and ii) polypeptides or proteins with at least 70% sequence identity to MtDef4 proprotein polypeptide sequence comprising an MtDef4 signal peptide and a mature MtDef4 protein. Mature MtDef4 polypeptide sequences include, but are not limited to, a MtDef4 consensus sequence (SEQ ID NO: 71), amino acids 30-76 of AL386553 (SEQ ID NO:105), MtDef4.1 (SEQ ID NO:112), MtDef4.2 (SEQ ID NO:114), MtDef4.3 (SEQ ID NO:116), MtDef4.1 (H33R) (SEQ ID NO:125), MtDef4.1 (H33R, C3S, C47S) (SEQ ID NO:135), MtDef4.1 (H33R, C14S, C34S) (SEQ ID NO:136), MtDef4.1 (H33R, C20S, C41S) (SEQ ID NO:137), MtDef4.1 (H33R, C24S, C43S) (SEQ ID NO:138), polypeptides that have at least 70% sequence identity to these sequences, and the biological functional equivalents of these sequences. MtDef4 pro-protein polypeptide sequences include, but are not limited to, an MtDef4 proprotein consensus sequence (SEQ ID NO: 99), the unique MtDef4 proproteins of SEQ ID NO: 77, 78, 80, 81 or 87, a MtDef4.1 proprotein sequence (SEQ ID NO:111), a MtDef4.2 proprotein sequence (SEQ ID NO:113), a MtDef4.3 proprotein sequence (SEQ ID NO:115), a MtDef4.1 (H33R) proprotein (SEQ ID NO:151), polypeptides that have at least 70% sequence identity to these sequences, and the biological functional equivalents of these sequences.

The phrase "inhibiting growth of a plant pathogenic fungus" as used herein refers to methods that result in any measurable decrease in fungal growth, where fungal growth includes but is not limited to any measurable decrease in the numbers an/or extent of fungal cells, spores, conidia, or mycelia. As used herein, "inhibiting growth of a plant pathogenic fungus" is also understood to include any measurable decrease in the adverse effects cause by fungal growth in a plant. Adverse effects of fungal growth in a plant include any type of plant tissue damage or necrosis, any type of plant yield reduction, any reduction in the value of the crop plant product, and/or production of undesirable fungal metabolites or fungal growth by-products including but not limited to mycotoxins.

The term "orthologs" as used herein refers to two or more homologous genes in different species that evolved from a common ancestral gene by speciation. Orthologs may have the same biological function in different species.

The phrase "operably linked" as used herein refers to the joining of nucleic acid sequences such that one sequence can provide a required function to a linked sequence. In the context of a promoter, "operably linked" means that the promoter is connected to a sequence of interest such that the transcription of that sequence of interest is controlled and regulated by that promoter. When the sequence of interest encodes a protein and when expression of that protein is desired, "operably linked" means that the promoter is linked to the sequence in such a way that the resulting transcript will be efficiently translated. If the linkage of the promoter to the coding sequence is a transcriptional fusion and expression of the encoded protein is desired, the linkage is made so that the first translational initiation codon in the resulting transcript is the initiation codon of the coding sequence. Alternatively, if the linkage of the promoter to the coding sequence is a translational fusion and expression of the encoded protein is desired, the linkage is made so that the first translational initiation codon contained in the 5' untranslated sequence associated with the promoter and is linked such that the resulting translation product is in frame with the translational open reading frame that encodes the protein desired. Nucleic acid sequences that can be operably linked include but are not limited to sequences that provide gene expression functions (i.e. gene expression elements such as promoters, 5' untranslated regions, introns, protein coding regions, 3' untranslated regions, polyadenylation sites, and/or transcriptional terminators), sequences that provide DNA transfer and/or integration functions (i.e. T-DNA border sequences, site specific recombinase recognition sites, integrase recognition sites), sequences that provide for selective functions (i.e. antibiotic resistance markers, biosynthetic genes), sequences that provide scoreable marker functions (i.e. reporter genes), sequences that facilitate in vitro or in vivo manipulations of the sequences (i.e. polylinker sequences, site specific recombination sequences) and sequences that provide replication functions (i.e. bacterial origins of replication, autonomous replication sequences, centromeric sequences).

The phrase "percent identity" as used herein refers to the number of elements (i.e., amino acids or nucleotides) in a sequence that are identical within a defined length of two optimally aligned DNA, RNA or protein segments. To calculate the "percent identity", the number of identical elements is divided by the total number of elements in the defined length of the aligned segments and multiplied by 100. When percentage of identity is used in reference to proteins it is understood that certain amino acid residues may not be identical but are nonetheless conservative amino acid substitutions that reflect substitutions of amino acid residues with similar chemical properties (e.g., acidic or basic, hydrophobic, hydrophilic, hydrogen bond donor or acceptor residues). Such substitutions may not change the functional properties of the molecule. Consequently, the percent identity of protein sequences can be increased to account for conservative substitutions.

The term "regeneration" as used herein refers to any method of obtaining a whole plant from any one of a seed, a plant cell, a group of plant cells, plant callus tissue, or an excised piece of a plant.

The term "transformation" as used herein refers to a process of introducing an exogenous DNA sequence (e.g., a vector, a recombinant DNA molecule) into a cell or protoplast in which that exogenous DNA is incorporated into a chromosome or is capable of autonomous replication.

The phrase "transgenic plant" refers to a plant or progeny thereof derived from a transformed plant cell or protoplast, wherein the plant DNA contains an introduced exogenous DNA molecule not originally present in a native, non-transgenic plant of the same species.

The term "vector" as used herein refers to a DNA or RNA molecule capable of replication in a host cell and/or to which another DNA or RNA segment can be operatively linked so as to bring about replication of the attached segment. A plasmid is an exemplary vector.

DNA Constructs Comprising Plant Expression Cassettes

The construction of expression cassettes for use in monocotyledonous plants or dicotyledonous plants is well established. Expression cassettes are DNA constructs where various promoter, coding, and polyadenylation sequences are operably linked. In general, expression cassettes typically comprise a promoter that is operably linked to a sequence of interest which is operably linked to a polyadenylation or terminator region. In certain instances including but not limited to the expression of transgenes in monocot plants, it may also be useful to include an intron sequence. When an intron sequence is included it is typically placed in the 5' untranslated leader region of the transgene. In certain instances, it may also be useful to incorporate specific 5' untranslated sequences in a transgene to enhance transcript stability or to promote efficient translation of the transcript.

A variety of promoters can be used in the practice of this invention. One broad class of useful promoters are referred to as "constitutive" promoters in that they are active in most plant organs throughout plant development. For example, the promoter can be a viral promoter such as a CaMV35S or FMV35S promoter. The CaMV35S and FMV35S promoters are active in a variety of transformed plant tissues and most plant organs (e.g., callus, leaf, seed and root). Enhanced or duplicate versions of the CaMV35S and FMV35S promoters are particularly useful in the practice of this invention (U.S. Pat. No. 5,378,619, incorporated herein by reference in its entirety). Other useful nopaline synthase (NOS) and octopine synthase (OCS) promoters (which are carried on tumor-inducing plasmids of *A. tumefaciens*), the cauliflower mosaic virus (CaMV) 19S promoters, a maize ubiquitin promoter, the rice Act1 promoter and the Figwort Mosaic Virus (FMV) 35S promoter (see e.g., U.S. Pat. No. 5,463,175; incorporated herein by reference in its entirety). It is understood that this group of exemplary promoters is non-limiting and that one skilled in the art could employ other promoters that are not explicitly cited here in the practice of this invention.

Promoters that are active in certain plant tissues (i.e. tissue specific promoters) can also be used to drive expression of MtDef4. Expression of MtDef4 in the tissue that is typically infected by the fungal pathogens is anticipated to be particularly useful. Thus, expression in reproductive tissues, seeds, roots, or leaves can be particularly useful in combating infection of those tissues by certain fungal pathogens in certain crops. Examples of useful tissue-specific, developmentally regulated promoters include but are not limited to the β-conglycinin 7S promoter (Doyle et al., 1986), seed-specific promoters (Lam and Chua, 1991), and promoters associated with napin, phaseolin, zein, soybean trypsin inhibitor, ACP, stearoyl-ACP desaturase, or oleosin genes. Examples of root specific promoters include but are not limited to the RB7 and RD2 promoters respectively described in U.S. Pat. Nos. 5,459,252 and 5,837,876.

Another class of useful promoters are promoters that are induced by various environmental stimuli. Promoters that are induced by environmental stimuli include but are not limited to promoters induced by heat (i.e. heat shock promoters such as Hsp70), promoters induced by light (i.e. the light-inducible promoter from the small subunit of ribulose 1,5-bisphosphate carboxylase, ssRUBISCO, a very abundant plant polypeptide), promoters induced by cold (i.e. COR promoters), promoters induced by oxidative stress (i.e. Catalase promoters), promoters induced by drought (i.e. the wheat Em and rice rab16A promoters) and promoters induced by multiple environmental signals (i.e. rd29A promoters, Glutathione-S-transferase (GST) promoters).

Promoters that are induced by fungal infections in plants can also be used to drive expression of MtDef4. Useful promoters induced by fungal infections include those promoters associated with genes involved in phenylpropanoid metabolism (e.g., phenylalanine ammonia lyase, chalcone synthase promoters), genes that modify plant cell walls (e.g., hydroxyproline-rich glycoprotein, glycine-rich protein, and peroxidase promoters), genes encoding enzymes that degrade fungal cell walls (e.g., chitinase or glucanase promoters), genes encoding thaumatin-like protein promoters, or genes encoding proteins of unknown function that display significant induction upon fungal infection. Maize and Flax promoters, designated as Mis1 and Fis1, respectively, are also induced by fungal infections in plants and can be used (U.S. Patent Application 20020115849).

An intron may also be included in the DNA expression construct, especially in instances when the sequence of interest is to be expressed in monocot plants. For monocot plant use, introns such as the maize hsp70 intron (U.S. Pat. No. 5,424,412; incorporated by reference herein in its entirety), the maize ubiquitin intron, the Adh intron 1 (Callis et al., 1987), the sucrose synthase intron (Vasil et al., 1989) or the rice Act1 intron (McElroy et al., 1990) can be used. Dicot plant introns that are useful include introns such as the CAT-1 intron (Cazzonnelli and Velten, 2003), the pKANNIBAL intron (Wesley et al., 2001; Collier et al., 2005), the PIV2 intron (Mankin et al., 1997) and the "Super Ubiquitin" intron (U.S. Pat. No. 6,596,925, incorporated herein by reference in its entirety; Collier et al., 2005) that have been operably integrated into transgenes. It is understood that this group of exemplary introns is non-limiting and that one skilled in the art could employ other introns that are not explicitly cited here in the practice of this invention.

Certain embodiments of this invention comprise a sequence encoding a signal peptide that allows for secretion of the mature MtDef4 protein from the cells. Portions of the MtDef4 genomic clone (SEQ ID NO:124), full length MtDef4 ESTs (SEQ ID NO:100, SEQ ID NO: 101, SEQ ID NO:102, SEQ ID NO:103, SEQ ID NO:104), MtDef4.1 (H33R) (SEQ ID NO:108), MtDef4.2 (SEQ ID NO:109), and MtDef4.3 (SEQ ID NO:110) contain sequences that encode MtDef4 signal peptides that can be used for secreting mature MtDef4 from plant or other cells. More specifically, nucleotide sequences encoding any of the signal peptide sequences of SEQ ID NO:117, 118, 119, 120, 121, 122, or 122 can be used to secrete mature MtDef4 from plant or other cells.

MtDef4 signal peptide encoding sequences can be used in the DNA constructs of the invention in a variety of ways. These MtDef4 signal sequences can be the MtDef4 signal sequences that are associated with a given MtDef4 mature protein coding sequence in a given MtDef4 cDNA or genomic clone. Alternatively, the MtDef4 signal can be operably linked to a distinct mature MtDef4 protein encoding sequence (i.e. MtDef4 signal peptide and mature protein encoding sequences derived from distinct genomic or cDNA clones can be operably linked). In the DNA constructs, nucleotide sequences encoding any MtDef4 proprotein comprising both a MtDef4 signal peptide and mature MtDef4 protein can also be used instead of two distinct signal peptide and mature MtDef4 protein encoding sequences. MtDef4 proproteins encoded by these sequences include but are not limited to an MtDef4 proprotein consensus sequences (SEQ ID NO: 70 and 99), unique MtDef4 proproteins such as AL385796 (SEQ ID NO:77), AW573770 (SEQ ID NO:78), AL386553 (SEQ ID NO:80), AL386552 (SEQ ID NO:81), BE999096 (SEQ ID NO:87), MtDef4.1 proprotein sequences (SEQ ID NO:111), MtDef4.2 proprotein sequences (SEQ ID NO:113), MtDef4.3 proprotein sequences (SEQ ID NO:115), polypeptides that have at least 70% sequence identity to these sequences, and the biological functional equivalents of these sequences. It is anticipated that the MtDef4 signal peptides can be used to secrete MtDef4 mature peptides from either monocot or dicot plant cells. Synthetic nucleotide sequences can also be obtained that encode the MtDef4 signal peptide sequences. The sequence of the MtDef4 gene fragment encoding a signal peptide can be deduced from the MtDef4 signal peptide sequence through use of the genetic code. The following table provides a list of MtDef4 signal peptides that can be used to secrete mature MtDef4 or other proteins from cells.

TABLE 1

MtDef4 Signal Peptide Sequences

| SEQ ID NO: | Amino Acid Sequence | Source |
|---|---|---|
| SEQ ID NO: 117 | Marsvplvstifvfllllvatgpsmvaea | MtDef4 signal peptide consensus |
| SEQ ID NO: 118 | Marsvplvstifvfllllvatgpsmvaea | MtDef4.1 (H33R) |
| SEQ ID NO: 119 | Marsvplvstifvfflllivatemgpsmvaa | MtDef4.2 |
| SEQ ID NO: 120 | Marsvplvstifvfflllvatemgpimvaea | MtDef4.3 |
| SEQ ID NO: 121 | Marsvflvstifvfllvlvatgpsmvaea | AL385796* |
| SEQ ID NO: 122 | Marsvslvftifvfllllvvatgpsmvaea | AW573770* |
| SEQ ID NO: 123 | Marsvplvstifvfllllvatgpsmvgea | BE999096* |

*GenBank Accession Number (including signal and mature peptide sequences)

Alternatively, the signal peptide sequences derived from other *Medicago* defensin proteins (Hanks et al, 2005) can be used. Examples of *Medicago* defensin protein signal peptides include, but are not limited to, signal peptides of MtDef1.1, MsDef1.6 and MtDef2.1. Another example of a useful signal peptide encoding sequence that can be used in monocot plants is the signal peptide derived from a barley cysteine endoproteinase gene (Koehler and Ho, 1990). Another example of a useful signal peptide encoding sequence that can be used in dicot plants is the tobacco PR1b signal peptide. It is understood that this group of exemplary signal peptides is non-limiting and that one skilled in the art could employ other signal peptides that are not explicitly cited here in the practice of this invention.

In this invention, a sequence encoding a mature MtDef4 protein is typically linked to the signal peptide encoding sequence. A variety of DNA sequences encoding a variety of mature MtDef4 proteins can be used in practicing this invention. The DNA sequence can encode mature MtDef4 proteins that include, but are not limited to, consensus MtDef4 mature peptide sequences such as SEQ ID NO:71, MtDef4 mature peptide sequences derived from unique MtDef4 encoding ESTs such as SEQ ID NO:80, MtDef4.1 (SEQ ID NO:112), MtDef4.1 (H33R) (SEQ ID NO:125), MtDef4.2 (SEQ ID NO:114), MtDef4.3 (SEQ ID NO:116), MtDef4.1 (H33R, C3S, C47S) (SEQ ID NO:135), MtDef4.1 (H33R, C14S, C34S) (SEQ ID NO:136), MtDef4.1 (H33R, C20S, C41S)

(SEQ ID NO:137), MtDef4.1 (H33R, C24S, C43S) (SEQ ID NO:138) and the biological functional equivalents of any of the foregoing amino acid sequences. Biological functional equivalents of an MtDef4 protein also include, but are not limited to, mature MtDef4 polypeptides with at least 85% sequence identity to SEQ ID NO:112. In certain embodiments of the invention, a mature MtDef4 protein-encoding sequence can be physically derived or obtained from either genomic DNA or cDNA obtained from *Medicago truncatula* plant tissue. Such methods for obtaining similar defensin genes from *Medicago truncatula* have been described (Hanks et al, 2005). The native or endogenous MtDef4-encoding nucleotide sequence is derived from a dicotyledonous plant in which it is ordinarily expressed under the control of the endogenous MtDef4 promoter sequence. Consequently, it is expected that the endogenous or naturally occurring MtDef4-encoding nucleotide sequence can be expressed in plants. In general, nucleic acids that encode MtDef4 proteins can be obtained from MtDef4 consensus nucleotide sequences, from synthetic MtDef4 genes derived by "back-translation" of MtDef4 polypeptide sequences, from genomic clones, from deduced coding sequences derived from genomic clones, from cDNA or EST sequences, and from any of the foregoing sequences that have been subjected to mutagenesis. Examples of nucleic acids that contain mature MtDef4 protein-encoding nucleotide sequences include but are not limited to a MtDef4.1 (H33R) synthetic gene (SEQ ID NO:72), full length MtDef4 ESTs (SEQ ID NO:100, SEQ ID NO:101, SEQ ID NO:102, SEQ ID NO:103, SEQ ID NO:104), MtDef4.1 genomic clone (SEQ ID NO:108), a MtDef4.2 genomic clone (SEQ ID NO:109), a MtDef4.3 genomic clone (SEQ ID NO:110); and a MtDef4 consensus nucleotide sequence (SEQ ID NO:141). Variant MtDef4 protein-encoding sequences derived by mutagenesis of MtDef4 nucleotide sequences or by direct synthesis that encode MtDef4 polypeptide substitutions such as a mature MtDef4.1 (H33R) coding sequence (SEQ ID NO:144), a mature MtDef4.1 (H33R, C3S, C47S) coding sequence (SEQ ID NO:146), a mature MtDef4.1 (H33R, C14S, C34S) coding sequence (SEQ ID NO: 147), a mature MtDef4.1 (H33R, C20S, C41S) coding sequence (SEQ ID NO:148) and a mature MtDef4.1 (H33R, C24S, C43S) coding sequence (SEQ ID NO:149) are also contemplated. Nucleotide sequences encoding various MtDef4 proteins can also be obtained from genomic sequences such as those for MtDef4.1 (SEQ ID NO:108), MtDef4.2 (SEQ ID NO:109), or MtDef4.3 (SEQ ID NO:110) by removing deduced intron sequences to obtain the deduced MtDef4 coding sequences for MtDef4.1 (SEQ ID NO:126), MtDef4.2 (SEQ ID NO:124), and MtDef4.3 (SEQ ID NO:143). Removal of the intron sequences from MtDef4 genomic clones can be effected by in vitro mutagenesis techniques. Alternatively, the intron sequences can be removed in silico (in a computer file) and the resultant deduced coding sequence synthesized by standard DNA synthesis techniques. It is further recognized that the closely related plant *Medicago sativa* is a source of MsDef4 ESTs that encode MsDef4 proteins that are either identical to, or otherwise biologically equivalent to, the MtDef4 polypeptides of this invention. An example of a MsDef4 EST is provided here by the MsDef4.1 cDNA sequence (SEQ ID NO:142). The MsDef4.1 EST sequence encodes the same amino acid sequence (i.e. SEQ ID NO:111) as the MtDef4.1 gene (SEQ ID NO:108). Nucleotide sequences encoding the MtDef4 polypeptides of this invention can be derived from other *Medicago* sp. such as *Medicago sativa* and can thus also be used in this invention. Portions of the aforementioned nucleotide sequences containing the sequences that encode mature MtDef4 peptides can be operably linked to either the native MtDef4 signal peptide sequence to which they are ordinarily linked or to another signal peptide via standard recombinant DNA techniques or by DNA synthesis methods.

In other embodiments of the invention, the MtDef4-encoding gene can be synthesized de novo from an MtDef4 mature peptide sequence. The sequence of the MtDef4 gene can be deduced from the MtDef4 peptide sequence through use of the genetic code. Computer programs such as "BackTranslate" (GCG™ Package, Acclerys, Inc. San Diego, Calif.) can be used to convert a peptide sequence to the corresponding nucleotide sequence that encodes the peptide. Examples of mature MtDef4 protein sequences that can be used to obtain corresponding nucleotide encoding sequences include, but are not limited to, consensus MtDef4 mature peptide sequences such as SEQ ID NO:71, MtDef4 mature peptide sequences derived from unique mtDef4 encoding ESTs such as SEQ ID NO:80, MtDef4.1 (SEQ ID NO:112), MtDef4.1 (H33R) (SEQ ID NO:125), MtDef4.2 (SEQ ID NO:114), MtDef4.3 (SEQ ID NO:116), MtDef4.1 (H33R, C3S, C47S) (SEQ ID NO:135), MtDef4.1 (H33R, C14S, C34S) (SEQ ID NO:136), MtDef4.1 (H33R, C20S, C41S) (SEQ ID NO:137), MtDef4.1 (H33R, C24S, C43S) (SEQ ID NO:138) and the biological functional equivalents of any of the foregoing amino acid sequences. Biological functional equivalents of an MtDef4 protein can also include mature MtDef4 polypeptides with at least 85% sequence identity to SEQ ID NO:112.

Furthermore, the synthetic MtDef4-encoding nucleotide sequence can designed so that it will be expressed in plants. U.S. Pat. No. 5,500,365 describes a method for synthesizing plant genes to optimize the expression level of the protein encoded by the synthesized gene. This method relates to the modification of the structural gene sequences of the exogenous transgene, to make them more "plant-like" and therefore more efficiently transcribed, processed, translated and expressed by the plant. Features of genes that are expressed well in plants include use of codons that are commonly used by the plant host and elimination of sequences that can cause undesired intron splicing or polyadenylation in the coding region of a gene transcript. A similar method for obtaining enhanced expression of transgenes in monocotyledonous plants is disclosed in U.S. Pat. No. 5,689,052. Furthermore, the synthetic design methods disclosed in U.S. Pat. No. 5,500, 365 and U.S. Pat. No. 5,689,052 could also be used to synthesize a signal peptide encoding sequence that is optimized for expression in plants in general or monocot plants in particular. A non-limiting example of a synthetic nucleotide sequence optimized for expression in monocot plants is SEQ ID NO:72. The synthetic gene represented by SEQ ID NO:72 encodes an MtDef4.1 (H33R) proprotein comprising an MtDef4 signal peptide that is operably linked to an MtDef4.1 (H33R) mature peptide sequence (SEQ ID NO:125).

Figure 9:
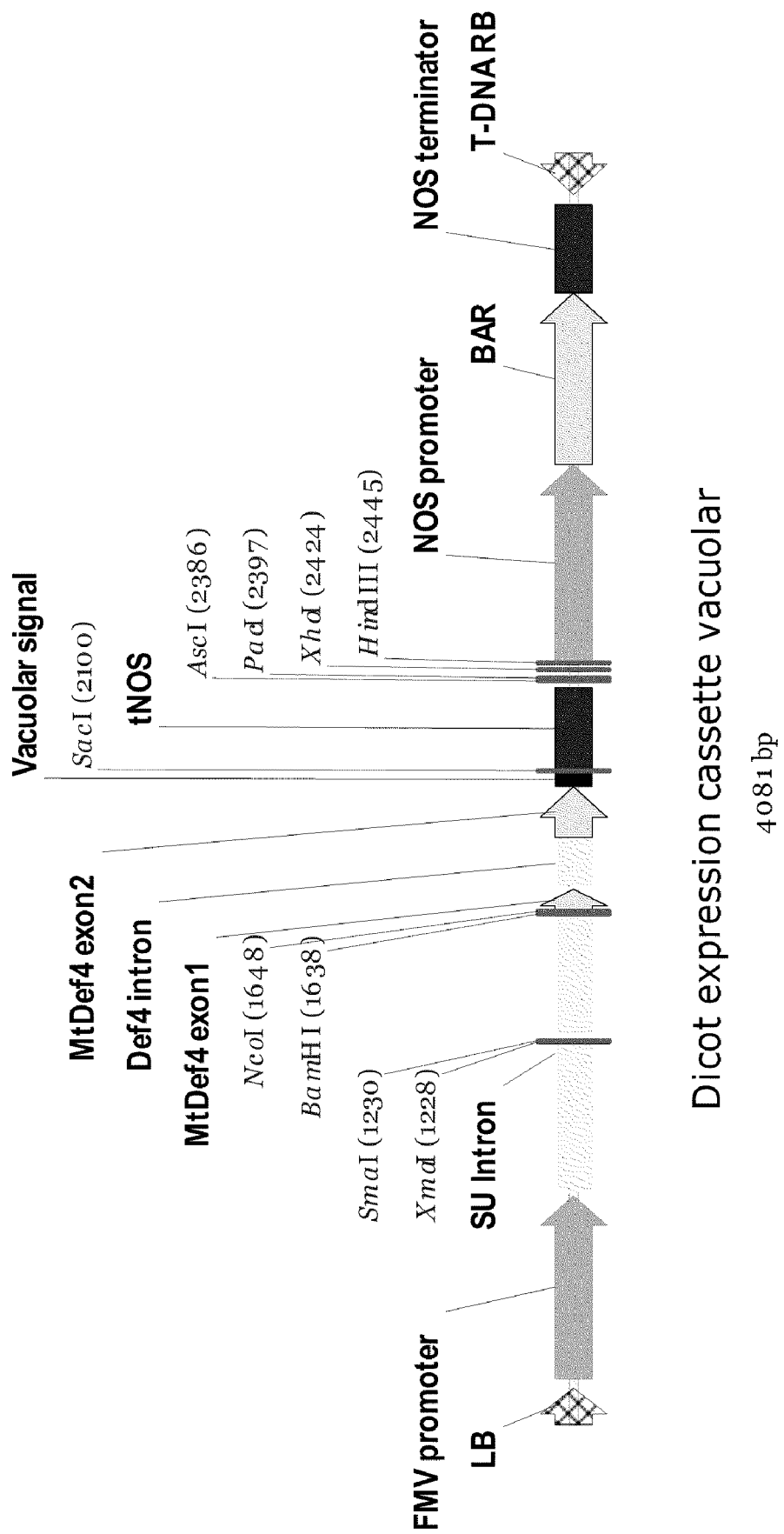
Figure 10:
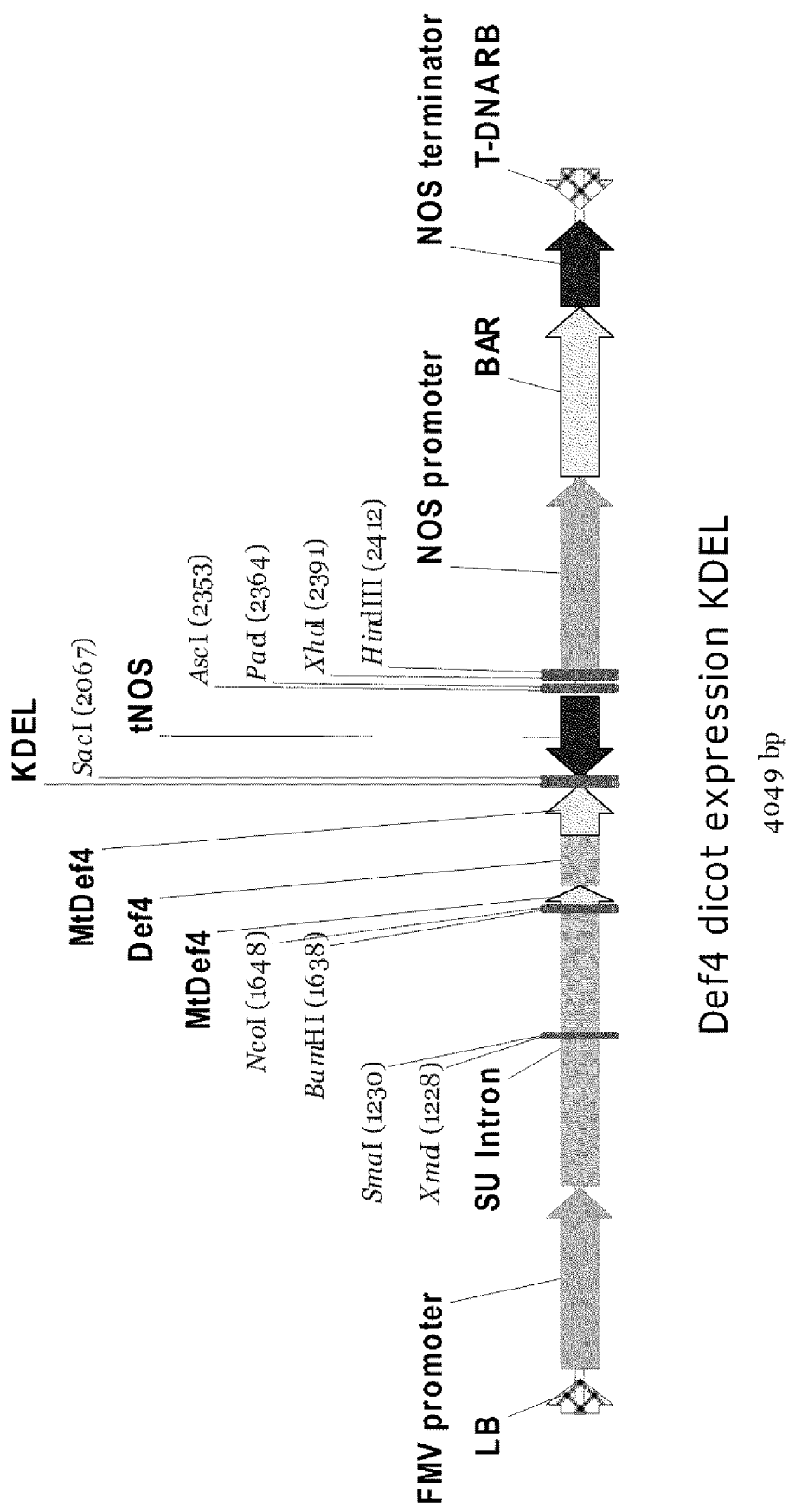

In other embodiments of the invention, sequences encoding peptides that provide for the localization of an MtDef4 in subcellular organelles can be operably linked to the sequences that encode the MtDef4 polypeptide. MtDef4 polypeptides that are operably linked to a signal peptide are expected to enter the secretion pathway and can be retained by organelles such as the endoplasmic reticulum (ER) or targeted to the vacuole by operably linking the appropriate retention or targeting peptides to the C-terminus of the MtDef4 polypeptide. Examples of vacuolar targeting peptides include, but are not limited to a CTPP vacuolar targeting signal from the barley lectin gene. An exemplary expression vector for vacuolar targeting of an MtDef4 peptide is shown in FIG. 9 and SEQ ID NO:76. Examples of ER targeting peptides include, but are not limited to a peptide comprising a KDEL amino acid sequence. An exemplary expression vector for ER retention of an MtDef4 peptide is shown in FIG. 10 and SEQ ID NO:150. Without seeking to be limited by theory, localization of MtDef4 polypeptides in either the endoplasmic reticulum or the vacuole can provide for desirable properties such as increased expression in transgenic plants and/or increased efficacy in inhibiting fungal growth in transgenic plants.

As noted above, the sequence of interest may also be operably linked to a 3' non-translated region containing a polyadenylation signal. This polyadenylation signal provides for the addition of a polyadenylate sequence to the 3' end of the RNA. The *Agrobacterium* tumor-inducing (Ti) plasmid nopaline synthase (NOS) gene 3' and the pea ssRUBISCO E9 gene 3' un-translated regions contain polyadenylate signals and represent non-limiting examples of such 3' untranslated regions that can be used in the practice of this invention. It is understood that this group of exemplary polyadenylation regions is non-limiting and that one skilled in the art could employ other polyadenylation regions that are not explicitly cited here in the practice of this invention.

The DNA constructs that comprise the plant expression cassettes described above are typically maintained in various vectors. Vectors contain sequences that provide for the replication of the vector and covalently linked sequences in a host cell. For example, bacterial vectors will contain origins of replication that permit replication of the vector in one or more bacterial hosts. *Agrobacterium*-mediated plant transformation vectors typically comprise sequences that permit replication in both *E. coli* and *Agrobacterium* as well as one or more "border" sequences positioned so as to permit integration of the expression cassette into the plant chromosome. Such *Agrobacterium* vectors can be adapted for use in either *Agrobacterium tumefaciens* or *Agrobacterium rhizogenes*. Selectable markers encoding genes that confer resistance to antibiotics are also typically included in the vectors to provide for their maintenance in bacterial hosts.

Methods for Obtaining Antifungal Plants

Methods of obtaining a transgenic plant capable of inhibiting growth of a plant pathogenic fungus are also provided by this invention. First, expression vectors suitable for expression of the MtDef4 protein in various dicot and monocot plants are introduced into a plant, a plant cell or a plant tissue using transformation techniques as described herein. Next a transgenic plant containing or comprising the MtDef4 expression vector is obtained by regenerating that transgenic plant from the plant, plant cell or plant tissue that received the expression vector. The final step is to obtain a transgenic plant that expresses a plant pathogenic fungus inhibitory amount of said mature MtDef4 polypeptide, where an "plant pathogenic fungus inhibitory amount" is a level of MtDef4 protein sufficient to provide any measurable decrease in fungal growth in the transgenic plant and/or any measurable decrease in the adverse effects caused by fungal growth in the transgenic plant.

Any of the MtDef4 expression vectors can be introduced into the chromosomes of a host plant via methods such as *Agrobacterium*-mediated transformation, *Rhizobium*-mediated transformation, *Sinorhizobium*-mediated transformation, particle-mediated transformation, DNA transfection, DNA electroporation, or "whiskers"-mediated transformation. Aforementioned methods of introducing transgenes are well known to those skilled in the art and are described in U.S. Patent Application No. 20050289673 (*Agrobacterium*-mediated transformation of corn), U.S. Pat. No. 7,002,058 (*Agrobacterium*-mediated transformation of soybean), U.S. Pat. No. 6,365,807 (particle mediated transformation of rice), and U.S. Pat. No. 5,004,863 (*Agrobacterium*-mediated transformation of cotton), each of which are incorporated herein by reference in their entirety. Methods of using bacteria such as *Rhizobium* or *Sinorhizobium* to transform plants are described in Broothaerts, et al., Nature. 2005, 10; 433(7026): 629-33. It is further understood that the MtDef4 expression vector can comprise cis-acting site-specific recombination sites recognized by site-specific recombinases, including Cre, Flp, Gin, Pin, Sre, pinD, Int-B13, and R. Methods of integrating DNA molecules at specific locations in the genomes of transgenic plants through use of site-specific recombinases can then be used (U.S. Pat. No. 7,102,055). Those skilled in the art will further appreciate that any of these gene transfer techniques can be used to introduce the expression vector into the chromosome of a plant cell, a plant tissue or a plant.

Methods of introducing plant minichromosomes comprising plant centromeres that provide for the maintenance of the recombinant minichromosome in a transgenic plant can also be used in practicing this invention (U.S. Pat. No. 6,972,197). In these embodiments of the invention, the transgenic plants harbor the minichromosomes as extrachromosomal elements that are not integrated into the chromosomes of the host plant.

Transgenic plants are typically obtained by linking the gene of interest (i.e., in this case an MtDef4 expression vectors) to a selectable marker gene, introducing the linked transgenes into a plant cell, a plant tissue or a plant by any one of the methods described above, and regenerating or otherwise recovering the transgenic plant under conditions requiring expression of said selectable marker gene for plant growth. The selectable marker gene can be a gene encoding a neomycin phosphotransferase protein, a phosphinothricin acetyltransferase protein, a glyphosate resistant 5-enol-pyruvylshikimate-3-phosphate synthase (EPSPS) protein, a hygromycin phosphotransferase protein, a dihydropteroate synthase protein, a sulfonylurea insensitive acetolactate synthase protein, an atrazine insensitive Q protein, a nitrilase protein capable of degrading bromoxynil, a dehalogenase protein capable of degrading dalapon, a 2,4-dichlorophenoxyacetate monoxygenase protein, a methotrexate insensitive dihydrofolate reductase protein, and an aminoethylcysteine insensitive octopine synthase protein. The corresponding selective agents used in conjunction with each gene can be: neomycin (for neomycin phosphotransferase protein selection), phosphinotricin (for phosphinothricin acetyltransferase protein selection), glyphosate (for glyphosate resistant 5-enol-pyruvylshikimate-3-phosphate synthase (EPSPS) protein selection), hygromycin (for hygromycin phosphotransferase protein selection), sulfadiazine (for a dihydropteroate synthase protein selection), chlorsulfuron (for a sulfonylurea insensitive acetolactate synthase protein selection), atrazine (for an atrazine insensitive Q protein selection), bromoxinyl (for a nitrilase protein selection), dalapon (for a dehalogenase protein selection), 2,4-dichlorophenoxyacetic acid (for a 2,4-dichlorophenoxyacetate monoxygenase protein selection), methotrexate (for a methotrexate insensitive dihydrofolate reductase protein selection), or aminoethylcysteine (for an aminoethylcysteine insensitive octopine synthase protein selection).

Transgenic plants can also be obtained by linking a gene of interest (i.e., in this case an MtDef4 expression vector) to a scoreable marker gene, introducing the linked transgenes into a plant cell by any one of the methods described above, and regenerating the transgenic plants from transformed plant cells that test positive for expression of the scoreable marker gene. The scoreable marker gene can be a gene encoding a beta-glucuronidase protein, a green fluorescent protein, a yellow fluorescent protein, a beta-galactosidase protein, a luciferase protein derived from a luc gene, a luciferase protein derived from a lux gene, a sialidase protein, streptomycin phosphotransferase protein, a nopaline synthase protein, an octopine synthase protein or a chloramphenicol acetyl transferase protein.

When the expression vector is introduced into a plant cell or plant tissue, the transformed cells or tissues are typically regenerated into whole plants by culturing these cells or tissues under conditions that promote the formation of a whole plant (i.e. the process of regenerating leaves, stems, roots, and, in certain plants, reproductive tissues). The development or regeneration of transgenic plants from either single plant protoplasts or various explants is well known in the art (Horsch, R. B. et al. 1985). This regeneration and growth process typically includes the steps of selection of transformed cells and culturing selected cells under conditions that will yield rooted plantlets. The resulting transgenic rooted shoots are thereafter planted in an appropriate plant growth medium such as soil. Alternatively, transgenes can also be introduced into isolated plant shoot meristems and plants regenerated without going through callus stage tissue culture (U.S. Pat. No. 7,002,058). When the transgene is introduced directly into a plant, or more specifically into the meristematic tissue of a plant, seed can be harvested from the plant and selected or scored for presence of the transgene. In the case of transgenic plant species that reproduce sexually, seeds can be collected from plants that have been "selfed" (self-pollinated) or out-crossed (i.e. used as a pollen donor or recipient) to establish and maintain the transgenic plant line. Transgenic plants that do not sexually reproduce can be vegetatively propagated to establish and maintain the transgenic plant line. As used here, transgenic plant line refers to transgenic plants derived from a transformation event where the transgene has inserted into one or more locations in the plant genome. In a related aspect, the present invention also encompasses a seed produced by the transformed plant, a progeny from such seed, and a seed produced by the progeny of the original transgenic plant, produced in accordance with the above process. Such progeny and seeds will have an MtDef4 protein-encoding transgene stably incorporated into their genome, and such progeny plants will inherit the traits afforded by the introduction of a stable transgene in Mendelian fashion. All such transgenic plants having incorporated into their genome transgenic DNA segments encoding one or more MtDef4 proteins or polypeptides are aspects of this invention. It is further recognized that transgenic plants containing the DNA constructs described herein, and materials derived therefrom, may be identified through use of PCR or other methods that can specifically detect the sequences in the DNA constructs.

Once a transgenic plant is regenerated or recovered, a variety of methods can be used to identify or obtain a transgenic plant that expresses a plant pathogenic fungus inhibitory amount of MtDef4. One general set of methods is to perform assays that measure the amount of MtDef4 that is produced. For example, various antibody-based detection methods employing antibodies that recognize MtDef4 can be used to quantitate the amount of MtDef4 produced. Examples of such antibody based assays include but are not limited to ELISAs, RIAs, or other methods wherein an MtDef4-recognizing antibody is detectably labelled with an enzyme, an isotope, a fluorophore, a lanthanide, and the like. By using purified or isolated MtDef4 protein as a reference standard in such assays (i.e. providing known amounts of MtDef4), the amount of MtDef4 present in the plant tissue in a mole per gram of plant material or mass per gram of plant material can be determined. The MtDef4 protein will typically be expressed in the transgenic plant at the level of "parts per million" or "PPM" where microgram levels of MtDef4 protein are present in gram amounts of fresh weight plant tissue. In this case, 1 microgram of MtDef4 protein per 1 gram of fresh weight plant tissue would represent a MtDef4 concentration of 1 PPM. A plant pathogenic fungus inhibitory amount of MtDef4 protein is at least 0.05 PPM (i.e. 0.05 µg MtDef4 protein per gram fresh weight plant tissue). In preferred embodiments, a plant pathogenic fungus inhibitory amount of MtDef4 protein is at least 0.5 PPM. In more preferred embodiments, the amount of MtDef4 is at least 1.0 PPM. In the most preferred embodiments, the amount of MtDef4 protein is at least 2.0 PPM.

Alternatively, the amount of MtDef4-encoding mRNA produced by the transgenic plant can be determined to identify plants that express plant pathogenic fungus inhibitory amounts of MtDef4 protein. Techniques for relating the amount of protein produced to the amount of RNA produced are well known to those skilled in the art and include methods such as constructing a standard curve that relates specific RNA levels (i.e. MtDef4 mRNA) to levels of the MtDef4 protein (determined by immunologic or other methods). Methods of quantitating MtDef4 mRNA typically involve specific hybridization of a polynucleotide to either the MtDef4 mRNA or to a cDNA (complementary DNA) or PCR product derived from the MtDef4 RNA. Such polynucleotide probes can be derived from either the sense and/or antisense strand nucleotide sequences of the MtDef4 protein-encoding transgene. Hybridization of a polynucleotide probe to the MtDef4 mRNA or cDNA can be detected by methods including, but not limited to, use of probes labelled with an isotope, a fluorophore, a lanthanide, or a hapten such as biotin or digoxigenin. Hybridization of the labelled probe may be detected when the MtDef4 RNA is in solution or immobilized on a solid support such as a membrane. When quantitating MtDef4 RNA by use of a quantitative reverse-transcriptase Polymerase Chain Reaction (qRT-PCR), the MtDef4-derived PCR product can be detected by use of any of the aforementioned labelled polynucleotide probes, by use of an intercalating dye such as ethidium bromide or SYBR green, or use of a hybridization probe containing a fluorophore and a quencher such that emission from the fluorophore is only detected when the fluorophore is released by the 5' nuclease activity of the polymerase used in the PCR reaction (i.e. a TaqMan™ reaction; Applied Biosystems, Foster City, Calif.) or when the fluorophore and quencher are displaced by polymerase mediated synthesis of the complementary strand (i.e. Scorpion™ or Molecular Beacon™ probes). Various methods for conducting qRT-PCR analysis to quantitate mRNA levels are well characterized (Bustin, S. A.; 2002). Fluorescent probes that are activated by the action of enzymes that recognize mismatched nucleic acid complexes (i.e. Invader™, Third Wave Technologies, Madison, Wis.) can also be used to quantitate RNA. Those skilled in the art will also understand that RNA quantitation techniques such as Quantitative Nucleic Acid Sequence Based Amplification (Q-NASBA™) can be used to quantitate MtDef4 protein-encoding mRNA and identify expressing plants.

Transgenic plants that express plant pathogenic fungus inhibitory amounts of MtDef4 can also be identified by directly assaying such plants for inhibition of the growth of a plant pathogenic fungus. Such assays can be used either independently or in conjunction with MtDef4-expression assays to identify the resistant transgenic plants. Infection of certain plants with certain plant pathogen fungi can result in distinctive effects on plant growth that are readily observed. Consequently, one can distinguish MtDef4-expressing transgenic plants by simply challenging such plants transformed with MtDef4-encoding transgenes with pathogenic plant fungi and observing reduction of the symptoms normally associated with such infections. Such observations are facilitated by co-infecting control plants that do not contain an MtDef4 encoding transgene with the same type and dose of plant pathogenic fungi used to infect the transgenic plants that contain an MtDef4-encoding transgene. Identification of transgenic plants that control or combat fungal infection can be based on observation of decreased disease symptoms, measurement of the decreased fungal growth in the infected plant (i.e., by determining the numbers of colony forming units per gram of infected tissue) and/or by measurement of the amount of mycotoxins present in infected plant tissue. The use of fungal disease severity assays and colony formation assays in conjunction with expression assays to identify transgenic MsDef1-expressing potato plants that are resistant to *Verticillium dahliae* has been described (U.S. Pat. No. 6,916,970 and Gao et al, 2000). It is similarly anticipated that a variety of MtDef4-expressing transgenic plants that combat or control fungal pathogens can be identified by scoring transgenic plants for resistance to fungal pathogens that infect those plants. Examples of MtDef4 transgene-conferred fungal resistance that can be assayed by observing reductions in disease symptoms or reductions in fungal growth include, but are not limited to, resistance of transgenic corn to *Fusarium verticillioides, Fusarium moniliforme, Stenocarpella maydis*, and/or *Cercospora zeae-maydis*; resistance of transgenic wheat to head blight (*Fusarium graminearum*), powdery mildew (*Erysiphe graminis* f. sp. *tritici*) or leaf rust (*Puccinia recondita* f. sp. *tritici*); resistance of transgenic cotton to *Fusarium oxysporum*; resistance of transgenic rice to *Magnaporthe grisea* and *Rhizoctonia solani*, and resistance of transgenic soybean to Asian Soybean rust (*Phakopsora pachyrhizi*), *Phytophthora* Root Rot (*Phytophthora* sp.), White Mold (*Sclerotinia* sp.), Sudden Death Syndrome (*Fusarium solani*) and/or Brown Stem Rot (*Phialophora gregata*).

Transgenic plants that express plant pathogenic fungus inhibitory amounts of MtDef4 can also be identified by measuring decreases in the adverse effects cause by fungal growth in a plant. Such decreases can be ascertained by comparing the extent of the adverse effect in an MtDef4 expressing transgenic plant relative to a control plant that does not express MtDef4. Adverse effects of fungal growth in a plant that can be measured include any type of plant tissue damage or necrosis, any type of plant yield reduction, any reduction in the value of the crop plant product, and/or production of undesirable fungal metabolites or fungal growth by-products including but not limited to mycotoxins. Mycotoxins comprise a number of toxic molecules produced by fungal species, including but not limited to polyketides (including aflatoxins, demethylsterigmatocystin, O-methylsterigmatocystin etc.), fumonisins, alperisins (e.g., $A_1$, $A_2$, $B_1$, $B_2$), sphingofungins (A, B, C and D), trichothecenes, fumifungins, and the like. Methods of quantitating mycotoxin levels are widely documented. Moreover, commercial kits for measurement of the mycotoxins such as aflatoxin, fumonisin, deoxynivalenol, and zearalenone are also available (VICAM, Watertown, Mass., USA).

A wide variety of plants can be transformed with MtDef4 expressing vectors to obtain transgenic plants that combat or control fungal infections. Transgenic monocot plants obtainable by the expression vectors and methods described herein include but are not limited to barley, corn, flax, oat, rice, rye, sorghum, turf grass, sugarcane, and wheat. Transgenic dicot plants obtainable by the expression vectors and methods described herein include but are not limited to alfalfa, *Arabidopsis*, barrel medic, banana, broccoli, bean, cabbage, canola, carrot, cassava, cauliflower, celery, citrus, cotton, cucurbits, eucalyptus, garlic, grape, onion, lettuce, pea, peanut, pepper, potato, poplar, pine, sunflower, safflower, soybean, strawberry, sugar beet, sweet potato, tobacco, and tomato.

Other proteins conferring certain advantages may likewise be co-expressed with the DNAs encoding the polypeptides of the present invention; including: (1) DNAs encoding enzymes such as glucose oxidase (which converts glucose to gluconic acid, concomitantly producing hydrogen peroxide which confers broad spectrum resistance to plant pathogens); pyruvate oxidase; oxalate oxidase; cholesterol oxidase; amino acid oxidases; and other oxidases that use molecular oxygen as a primary or secondary substrates to produce peroxides, including hydrogen peroxide; (2) pathogenesis-related proteins such as SAR8.2a and SAR8.2b proteins; the acidic and basic forms of tobacco PR-1a, PR-1b, PR-1c, PR-1', PR-2, PR-3, PR-4, PR-5, PR-N, PR-O, PR-O', PR-P, PR-Q, PR-S, and PR-R proteins; chitinases such as tobacco basic chitinase and cucumber chitinase/lysozyme; peroxidases such as cucumber basic peroxidase; glucanases such as tobacco basic glucanase; osmotin-like proteins; (3) viral capsid proteins and replicases of plant viruses; (4) plant R-genes (resistance genes) and homologs thereof, including but not limited to *Arabidopsis* RPS2 (Bent et al., 1994), *Arabidopsis* RPM1 (Grant et al., 1995), tobacco N-gene and N'-gene, tomato Cf-9, flax L6, and rice Xa21; (5) pathogen Avr genes, such as *Cladosporium fulvum* Avr9, that can be expressed using pathogen- or chemical-inducible promoters; (6) genes that are involved in the biosynthesis of salicylic acid, such as benzoic acid 2-hydroxylase; and (7) other defensin proteins with antifungal modes-of-action distinct from the mode-of-action of MtDef4, including but not limited to, MsDef1, MtDef2, Rs-AFP1 and Rs-AFP2.

Yeast Expression Vectors and Transformation Systems

Expression of MtDef4 proteins in yeast is specifically contemplated herein. The construction of expression vectors for production of heterologous proteins in various yeast genera is well established. In general, such expression vectors typically comprise a promoter that is operably linked to a sequence of interest which is operably linked to a polyadenylation or terminator region. Examples of yeast genera that have been used to successfully express heterologous genes include *Candida, Kluveromyces, Hansuela, Pichia, Saccharomyces, Schizosaccharomyces*, and *Yarrowia*. A general description of expression vectors and transformation systems for *Saccharomyces* is found in Kingsman et al (1985). Expression vectors and transformation systems useful for yeasts other than *Saccharomyces* are described in Reiser et al (1990).

In general, the promoter and polyadenylation region are selected based on their operability in the desired yeast host. For example, the AOX1 or AOX2 promoters of *Pichia* can be used in conjunction with the AOX1, AOX2, p40 or p76 polyadenylation sequences of *Pichia* to express a heterologous protein such as an MtDef4 protein. Both the AOX1 and AOX2 promoters are particularly useful in *Pichia* as both promoters provide for abundant expression of the linked heterologous gene when induced by addition of methanol to the growth media. The use of these *Pichia* promoters and polyadenylation sequences is described in U.S. Pat. No. 4,855,231, which is expressly incorporated herein by reference in its entirety.

Similarly, the Hansuela MOX, DHAS, or FMDH promoters can be used to express heterologous proteins such as MtDef4 in *Hansuela*. The MOX, DHAS, or FMDH promoters are particularly useful in *Hansuela* as these promoters provide for abundant expression of the linked heterologous gene when induced by addition of methanol to the growth media. The use of the MOX and DHAS promoters in *Hansuela* is described in U.S. Pat. No. 5,741,672 while the use of the FMDH promoter in *Hansuela* is described in U.S. Pat. No. 5,389,525, each of which is expressly incorporated herein by reference in their entireties.

For *Kluveromyces*, a Lactase promoter and polyadenylation sequence can be used to express heterologous genes such as MtDef4. Expression of heterologous genes that are operably linked to the Lactase promoter and polyadenylation sequence is achieved by growing *Kluveromyces* in the presence of galactose. The use of the Lactase promoter and polyadenylation sequences in *Kluveromyces* is described in U.S. Pat. No. 6,602,682, which is expressly incorporated herein by reference in its' entirety.

Yeast expression vectors that provide for secretion of heterologous proteins such as MtDef4 into the growth media by transformed yeast are also contemplated. Secretion of the mature MtDef4 protein is typically achieved by operable linkage of a signal peptide sequence or a signal peptide and propeptide sequence to the mature MtDef4 peptide encoding sequence. Examples of useful signal peptides for secretion of heterologous proteins in yeast include but are not limited to an α-factor signal peptide, an invertase signal peptide, and a PHO1 signal peptide, all of which are derived from yeast. The α-factor signal peptide is typically derived from *Saccharomyces*, *Kluveromyces* or *Candida*, while the PHO1 signal peptide is derived from *Pichia*.

A particularly useful signal peptide sequence or signal peptide and propeptide sequence for secretion of proteins in yeast is derived from the *S. cerevisiae* α-factor and is described in U.S. Pat. Nos. 4,546,082, 4,588,684, 4,870,008, and 5,602,034. The *S. cerevisiae* α-factor signal peptide and propeptide sequence consist of amino acids 1-83 of the primary, unprocessed translation product of the *S. cerevisiae* alpha mating factor gene (GenBank Accession Number: P01149). In certain embodiments, the signal peptide sequence of the alpha-mating factor comprising amino acids 1 to about 19 to 23 of the alpha-mating factor proprotein can be directly linked to the N-terminus of the mature MtDef4 protein to provide for secretion of mature MtDef4 protein. In this case, the signal peptide is cleaved from the mature MtDef4 protein in the course of the secretion process. Alternatively, the signal peptide and propeptide of the alpha mating factor can be operably linked to the mature MtDef4 encoding sequence via a spacer sequence. This spacer sequence can comprise a variety of sequences that provide for proteolytic processing of the leader sequence and gene of interest. In the native *S. cerevisiae* alpha mating factor gene the spacer sequence corresponds to amino acid residues 84-89 and is represented by the sequence Lys84-Arg85-Glu86-Ala87-Glu88-Ala 89. The sequence Lys-Arg corresponds to a KEX2 protease recognition site while the Glu-Ala-Glu-Ala sequence corresponds to a duplicated dipeptidylaminopeptidase or STE13 recognition site. In certain embodiments, a DNA fragment encoding the 89 amino acid *S. cerevisiae* alpha factor signal, propeptide coding region, and entire native spacer coding region (i.e., the N-terminal 89 amino acid residues of the alpha mating factor precursor protein containing both the Lys-Arg KEX2 protease cleavage site at residues 84 and 85 as well as the Glu-Ala-Glu-Ala dipeptidylaminopeptidase or STE13 recognition site at residues 86-89 is operably linked to the sequence encoding the mature MtDef4 protein. When the N-terminal 89 amino acids of the alpha mating factor precursor protein are fused to the N-terminus of a heterologous protein such as MtDef4, the propeptide sequence is typically dissociated from the heterologous protein via the cleavage by endogenous yeast proteases at either the KEX2 or STE13 recognition sites. In other embodiments, a DNA fragment encoding the smaller 85 amino acid *Saccharomyces cerevisiae* alpha factor signal peptide, propeptide and KEX2 spacer element (i.e., the N-terminal 85 amino acid residues of the alpha mating factor precursor protein containing just the Lys-Arg KEX2 protease cleavage site at residues 84 and 85) is operably linked to the sequence encoding the mature MtDef4 protein. When the N-terminal 85 amino acids of the alpha mating factor precursor protein are fused to the N-terminus of a heterologous protein such as MtDef4, the propeptide sequence is typically dissociated from the heterologous protein via cleavage by endogenous yeast proteases at the KEX2 recognition site. The MtDef4 protein can thus be expressed without the glu-ala repeats.

To obtain transformed yeast that express MtDef4, the yeast MtDef4 expression cassettes (i.e. yeast promoter, yeast signal peptide encoding sequence, MtDef4 mature sequence, and polyadenylation sequence) are typically combined with other sequences that provide for selection of transformed yeast. Examples of useful selectable marker genes include but are not limited to genes encoding a ADE protein, a HIS5 protein, a HIS4 protein, a LEU2 protein, a URA3 protein, ARG4 protein, a TRP1 protein, a LYS2 protein, a protein conferring resistance to a bleomycin or phleomycin antibiotic, a protein conferring resistance to chloramphenicol, a protein conferring resistance to G418 or geneticin, a protein conferring resistance to hygromycin, a protein conferring resistance to methotrexate, an a ARO4-OFP protein, and a FZF1-4 protein.

DNA molecules comprising the yeast MtDef4 expression cassettes and selectable marker genes are introduced into yeast cells by techniques such as transfection into yeast spheroplasts or electroporation. In certain embodiments of the invention, the DNA molecules comprising the yeast MtDef4 expression cassettes and selectable marker genes are introduced as linear DNA fragments that are integrated into the genome of the transformed yeast host cell. Integration may occur either at random sites in the yeast host cell genome or at specific sites in the yeast host cell genome. Integration at specific sites in the yeast host cell genome is typically accomplished by homologous recombination between sequences contained in the expression vector and sequences in the yeast host cell genome. Homologous recombination is typically accomplished by linearizing the expression vector within the homologous sequence (i.e. for example, within the AOX1 promoter sequence of a *Pichia* expression vector when integrating the expression vector into the endogenous AOX1 gene in the *Pichia* host cell). In other embodiments of the invention, the yeast expression cassettes may also comprise additional sequences such as autonomous replication sequences (ARS) that provide for the replication of DNA containing the expression cassette as an extrachromosomal (i.e. non-integrated) element. Such extra-chromosomal elements are typically maintained in yeast cells by continuous selection for the presence of the linked selectable marker gene. Yeast artificial chromosomes (YACs) containing sequences that provide for replication and mitotic transmission are another type of vector that can be used to maintain the DNA construct in a yeast host.

Methods of Producing MtDef4 Protein in Yeast

Yeast cells transformed with the yeast MtDef4 expression cassettes can also be used to produce the MtDef4 protein. This MtDef4 protein can be used directly as an antifungal agent, as an immunogen to raise antibodies that recognize the MtDef4 protein, or as a reference standard in kits for measuring concentrations of MtDef4 protein in various samples. The methods of producing MtDef4 protein typically first comprise the step of culturing yeast cells transformed with MtDef4 expression cassettes under conditions wherein said yeast cell expresses a mature MtDef4 polypeptide. In general, the conditions where the yeast cell expresses the mature MtDef4 polypeptide are conditions that allow for or specifically induce expression of the yeast promoter that is operably linked to the MtDef4 gene in the yeast expression cassette. When the yeast is *Pichia* and the signal-peptide/MtDef4 gene is under the control of an AOX1 or AOX2 promoter, addition of methanol to the growth media will provide for expression of mature MtDef4 protein. Similarly, when the yeast is *Hansuela* and the signal-peptide/MtDef4 gene is under the control of an MOX, DHAS, or FMDH promoter, addition of methanol to the growth media will provide for expression of mature MtDef4 protein. Alternatively, when the yeast is *Kluveromyces* and the signal-peptide/MtDef4 gene is under the control of an Lactase promoter, addition of galactose to the growth media will provide for expression of mature MtDef4 protein.

Once the transformed yeast culture has been incubated in the culture conditions that provide for expression of mature MtDef4 for a sufficient period of time, the mature MtDef4 protein can be isolated from the culture. A sufficient period of time can be determined by periodically harvesting portions or aliquots of the culture and assaying for the presence of mature MtDef4. Analytical assays such as SDS-PAGE with protein staining, Western blot analysis, or any immunodetection method (i.e. such as an ELISA) can be used to monitor MtDef4 production. For example, incubation in the presence of methanol for between 1 to 8 days is sufficient to provide for expression of mature MtDef4 from the AOX1 promoter in *Pichia*.

Isolation of the MtDef4 protein from the culture can be partial or complete. For MtDef4 expression vectors where a yeast signal peptide is operably linked to the sequence encoding the mature MtDef4 protein, the mature MtDef4 protein can be recovered from the yeast cell culture media. Yeast cell culture media that contains the mature MtDef4 protein can be separated from the yeast cells by centrifugation or filtration, thus effecting isolation of mature MtDef4 protein. Yeast cell culture media that contains the mature MtDef4 protein can be further processed by any combination of dialysis and/or concentration techniques (i.e. precipitation, lyophilization, filtration) to produce a composition containing the MtDef4 protein. Production of MtDef4 protein can also comprise additional purification steps that result in either a partially or completely pure preparation of the MtDef4 protein. To effect such purification, filtration size-exclusion membranes can be used. Alternatively, various types of chromatographic techniques such as size exclusion chromatography, ion-exchange chromatography, or affinity chromatography can be used to produce a partially or completely pure preparation of the MtDef4 protein.

Combinations of various isolation techniques can also be employed to produce the mature MtDef4 protein. For example, the cell culture medium can be separated from the cells by centrifugation and dialyzed or adjusted. A preferred buffer for dialysis or adjustment is a 25 mM sodium acetate buffer at about pH4.5-pH6.0. This diazylate is then subjected to ion-exchange chromatography. For example, a cation-exchange resin such as CM-Sephadex C-25 equilibrated with a 25 mM sodium acetate buffer at about pH6.0 can be used. MtDef4 protein bound to the cation exchange resin is washed and then eluted. For example, the aforementioned column is washed with 25 mM sodium acetate buffer at about pH6.0 and subsequently eluted in 1M NaCl, 50 mM Tris, pH7.6. Fractions containing the defensin protein are identified by an assay or by UV absorbance and then concentrated by a size-cut-off filtration membrane. The concentrated MtDef4 protein is then dialyzed to obtain an essentially pure MtDef4 protein in a desirable buffer. Desirable buffers include, but are not limited to, buffers such as 10 mM Tris, pH 7.6.

Peptides, Polypeptides, and Proteins Containing Conservative Amino Acid Changes in the MtDef4 Polypeptide Sequence Peptides, polypeptides, and proteins biologically functionally equivalent to MtDef4 include, but are not limited to, amino acid sequences containing conservative amino acid substitutions in the mature MtDef4 protein sequences. Examples of mature MtDef4 proteins that can be substituted to obtain biological equivalents include, but are not limited to, the MtDef4 consensus sequence (SEQ ID NO: 71), amino acids 30-76 of AL386553 (SEQ ID NO:105), MtDef4.1 (SEQ ID NO:112), MtDef4.2 (SEQ ID NO:114), MtDef4.3 (SEQ ID NO:116), MtDef4.1 (H33R) (SEQ ID NO:125), MtDef4.1 (H33R, C3S, C47S) (SEQ ID NO:135), MtDef4.1 (H33R, C14S, C34S) (SEQ ID NO:136), MtDef4.1 (H33R, C20S, C41S) (SEQ ID NO:137), and MtDef4.1 (H33R, C24S, C43S) (SEQ ID NO:138). Peptides, polypeptides, and proteins biologically functionally equivalent to MtDef4 also include, but are not limited to, amino acid sequences containing conservative amino acid substitutions in the MtDef4 proprotein sequences. Examples of MtDef4 proproteins that can be substituted to obtain biological equivalents include, but are not limited to a MtDef4 proprotein consensus sequence (SEQ ID NO: 99), a MtDef4 proprotein sequence AL385796 (SEQ ID NO:77), AW573770 (SEQ ID NO:78), AL386553 (SEQ ID NO:80), AL386552 (SEQ ID NO:81), BE999096 (SEQ ID NO:87), a MtDef4.1 proprotein sequence (SEQ ID NO:111), a MtDef4.2 proprotein sequence (SEQ ID NO:113), and a MtDef4.3 proprotein sequence (SEQ ID NO:115). In such amino acid sequences, one or more amino acids in the sequence is (are) substituted with another amino acid(s), the charge and polarity of which is similar to that of the native amino acid, i.e., a conservative amino acid substitution, resulting in a silent change.

Substitutes for an amino acid within the MtDef4 polypeptide sequence can be selected from other members of the class to which the naturally occurring amino acid belongs. Amino acids can be divided into the following four groups: (1) acidic amino acids; (2) basic amino acids; (3) neutral polar amino acids; and (4) neutral non-polar amino acids. Representative amino acids within these various groups include, but are not limited to: (1) acidic (negatively charged) amino acids such as aspartic acid and glutamic acid; (2) basic (positively charged) amino acids such as arginine, histidine, and lysine; (3) neutral polar amino acids such as glycine, serine, threonine, cysteine, cystine, tyrosine, asparagine, and glutamine; (4) neutral non-polar (hydrophobic) amino acids such as alanine, leucine, isoleucine, valine, proline, phenylalanine, tryptophan, and methionine.

Conservative amino acid changes within the MtDef4 polypeptide sequence can be made by substituting one amino acid within one of these groups with another amino acid within the same group. Biologically functional equivalents of MtDef4 can have 10 or fewer conservative amino acid changes, more preferably seven or fewer conservative amino acid changes, and most preferably five or fewer conservative amino acid changes. The encoding nucleotide sequence (gene, plasmid DNA, cDNA, or synthetic DNA) will thus have corresponding base substitutions, permitting it to encode biologically functional equivalent forms of MtDef4.

The biologically functional equivalent peptides, polypeptides, and proteins contemplated herein should possess about 70% or greater sequence identity, preferably about 85% or greater sequence identity, and most preferably about 90% to 95% or greater sequence identity, to the sequence of, or corresponding moiety within, the MtDef4 polypeptide sequence. In certain embodiments of the invention, biologically functional equivalent peptides, polypeptides, and proteins possessing about 80% or greater sequence identity, preferably about 85% or greater sequence identity, and most preferably about 90% to 95% or greater sequence identity, to the sequence of MtDef4.1 (SEQ ID NO:112).

As indicated, modification and changes may be made in the structure of the peptides of the present invention and DNA segments which encode them and still obtain a functional molecule that encodes a protein or peptide with desirable characteristics. The following is a discussion based upon changing the amino acids of a protein to create an equivalent, or even an improved, second-generation molecule. In particular embodiments of the invention, mutated MtDef4 proteins are contemplated to be useful for increasing the antifungal activity of the protein, and consequently increasing the antifungal activity and/or expression of the recombinant transgene in a plant cell. The amino acid changes may be achieved by changing the codons of the DNA sequence, according to the codons given in Table 2.

TABLE 2

| Amino Acids | Amino Acid Codes | Codons |
|---|---|---|
| Alanine | Ala (A) | GCA GCC GCG GCU |
| Cysteine | Cys (C) | UGC UGU |
| Aspartic acid | Asp (D) | GAC GAU |
| Glutamic acid | Glu (E) | GAA GAG |
| Phenylalanine | Phe (F) | UUC UUU |
| Glycine | Gly (G) | GGA GGC GGG GGU |
| Histidine | His (H) | CAC CAU |
| Isoleucine | Ile (I) | AUA AUC AUU |
| Lysine | Lys (K) | AAA AAG |
| Leucine | Leu (L) | UUA UUG CUA CUC CUG CUU |
| Methionine | Met (M) | AUG |
| Asparagine | Asn (N) | AAC AAU |
| Proline | Pro (P) | CCA CCC CCG CCU |
| Glutamine | Gln (Q) | CAA CAG |
| Arginine | Arg (R) | AGA AGG CGA CGC CGG CGU |
| Serine | Ser (S) | AGC AGU UCA UCC UCG UCU |
| Threonine | Thr (T) | ACA ACC ACG ACU |
| Valine | Val (V) | GUA GUC GUG GUU |
| Tryptophan | Trp (W) | UGG |
| Tyrosine | Tyr (Y) | UAC UAU |

For example, certain amino acids may be substituted for other amino acids in a protein structure without appreciable loss of biochemical or biological activity. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated by the inventors that various changes may be made in the peptide sequences of the disclosed compositions, or corresponding DNA sequences which encode said peptides without appreciable loss of their biological utility or activity.

In making such changes, the hydropathic index of amino acids may be considered. The importance of the hydropathic amino acid index in conferring interactive biologic function on a protein is generally understood in the art (Kyte and Doolittle, 1982, incorporated herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of its hydrophobicity and charge characteristics (Kyte and Doolittle, 1982). These are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within .±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0.±0.1); glutamate (+3.0.±0.1); serine (+0.3); asparagine (+0.2); glutamine (+0.2); glycine (0); threonine (−0.4); proline (−0.5.±0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

Non-Conservative Substitutions in the MtDef4 Polypeptides

It is further recognized that non-conservative substitutions in MtDef4 polypeptide sequences can be made to obtain MtDef4 polypeptides that are the functional biological equivalents of the MtDef4 polypeptides disclosed herein. In these instances, the non-conservative substitutions can simply be tested for inhibition of fungal growth to identify non-conservative substitutions that provide for functional biological equivalents of a given MtDef4 polypeptide. Examples of non-conservative substitutions in an MtDef4 polypeptide that provide for functional biological equivalents include, but are not limited to, substitutions of a serine residue for a cysteine residue in the MtDef4.1 (H33R) polypeptide to yield the biologically active functional equivalents MtDef4.1 (H33R, C3S, C47S) (SEQ ID NO:135), MtDef4.1 (H33R, C14S, C34S) (SEQ ID NO:136), MtDef4.1 (H33R, C20S, C41S) (SEQ ID NO:137), and MtDef4.1 (H33R, C24S, C43S) (SEQ ID NO:138).

Fragments and Variants of MtDef4:

While the antifungal polypeptide of the present invention preferably comprises a mature MtDef4 protein sequence, fragments and variants of this sequence possessing the same or similar antifungal activity as that of this antifungal protein are also encompassed by the present invention. Thus contiguous sequences of at least 8 or more amino acids in an MtDef4 mature protein with antifungal activity are anticipated by this invention. Fragments or variants of MtDef4 with antifungal activity that are anticipated by this invention can also comprise amino acid substitutions, deletions, insertions or additions in an MtDef4 protein sequence.

The antifungal polypeptide of the present invention preferably comprises the mature MtDef4.1 protein sequence (SEQ ID NO:112), fragments and variants of this sequence possessing the same or similar antifungal activity as that of this particular MtDef4 protein are also encompassed by the present invention are anticipated by this invention. Thus contiguous sequences of at least 8 or more amino acids in SEQ ID NO:112 with antifungal activity are anticipated by this invention. The fragments or variants with antifungal activity that are anticipated by this invention can also comprise amino acid substitutions, deletions, insertions or additions of the sequence shown in SEQ ID NO:112.

Fragments of the mature MtDef4 protein can be truncated forms wherein one or more amino acids are deleted from the N-terminal end, C-terminal end, the middle of the protein, or combinations thereof with antifungal activity are also anticipated by this invention. These fragments can be naturally occurring or synthetic mutants of MtDef4, and retain the antifungal activity of MtDef4. A preferred MtDef4 protein that can be used to obtain truncated derivatives with antifungal activity is the MtDef4.1 protein of SEQ ID NO:112.

Variants of MtDef4 include forms wherein one or more amino acids has/have been inserted into the natural sequence. These variants can also be naturally occurring or synthetic mutants of MtDef4, and should retain the antifungal activity of MtDef4.

Combinations of the foregoing, i.e., forms of the antifungal polypeptide containing both amino acid deletions and additions, are also encompassed by the present invention. Amino acid substitutions can also be present therein as well.

The fragments and variants of MtDef4 encompassed by the present invention should preferably possess about 70-75% or greater sequence identity, more preferably about 80%, 85%, 88% or greater sequence identity, and most preferably about 90% to 95% or greater amino acid sequence identity, to the corresponding regions of the mature MtDef4 protein having the corresponding amino acid sequences shown in SEQ ID NO:112.

Use of Defensin Structure Function Relationships to Design MtDef4 Variants

The MtDef4 proteins are members of the Defensin gene family and are thus anticipated to possess certain structural and biochemical properties shared by Defensins. In particular, the MtDef4 proteins are anticipated to possess a cysteine-stabilized α/β motif, composed of three antiparallel β-strands and one α-helix, that are typically observed in Defensin proteins (Almeida et al, J. Mol. Biol. (2002) 315, 749-757; Thomma et al, Planta (2002) 216: 193-202). Without being limited by theory, the structural homology between MtDef4 and other defensins can be used to identify variants that possess similar or even increased antifungal activity.

Alternatively, the conserved structural features of the MtDef4 defensins can also be used to engineer variant MtDef4 derivatives with other desirable properties. For example, the 8 canonical cysteine residues of MtDef4 that typically form disulfide linkages in Defensin proteins would typically be conserved or maintained in any MtDef4 variants. The predicted pairing of disulfide bonds in MtDef4 is between cysteine residues 3 and 47, 14 and 34, 20 and 41, and 24 and 43. Thus, Cys-pair 1 is predicted to be formed by a Cys3-Cys47 disulfide bond, Cys-pair 2 is predicted to be formed by a Cys14-Cys34 disulfide bond, Cys-pair 3 is predicted to be formed by a Cys20-Cys41 disulfide bond, and Cys-pair 4 is predicted to be formed by a Cys24-Cys43 disulfide bond. While not being limited by theory, it is believed that MtDef4 cysteine variants that lack one or more disulfide linkages may be desirable for use in transgenic plants that are ultimately used as animal feed or as food for human consumption as such variants are predicted to be more readily digested by animal or humans that consume the transgenic plant products. MtDef4 variant proteins that have shorter half-lives in the digestive tracts of animals or humans are in theory anticipated to have less potential to become food allergens. It would thus be desirable to design MtDef4 defensin derivatives that have fewer disulfide bonds yet retain antifungal activity. The MtDef4 cysteine variants MtDef4.1 (H33R, C3S, C47S(SEQ ID NO:135), MtDef4.1 (H33R, C14S, C34S) (SEQ ID NO:136), MtDef4.1 (H33R, C20S, C41S) (SEQ ID NO:137), and MtDef4.1 (H33R, C24S, C43S) (SEQ ID NO:138) all lack predicted disulfide linkages yet retain antifungal activity. Consequently, each of these variants is predicted to be more readily digested when consumed by humans or animals.

Other Biologically Functional Equivalent Forms of MtDef4

Other biologically functional equivalent forms of MtDef4 useful in the present invention include conjugates of the polypeptides, or biologically functional equivalents thereof as described above, with other peptides, polypeptides, or proteins, forming fusion products therewith exhibiting the same, similar, or greater antifungal activity as compared with that of MtDef4 having the amino acid sequence shown in SEQ ID NO:112.

Simultaneous co-expression of multiple antifungal and/or other anti-pathogen proteins in plants is advantageous in that it exploits more than one mode of control of plant pathogens. This may, where two or more antifungal proteins are expressed, minimize the possibility of developing resistant fungal species, broaden the scope of resistance and potentially result in a synergistic antifungal effect, thereby enhancing the level of resistance.

Site-Specific Mutagenesis

Site-specific mutagenesis is a technique useful in the preparation of individual peptides, or biologically functional equivalent proteins or peptides, through specific mutagenesis of the DNA encoding the protein. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

In general, the technique of site-specific mutagenesis is well known in the art, as exemplified by various publications. As will be appreciated, the technique typically employs a phage vector which exists in both a single-stranded and double-stranded form. Typical vectors useful in site-directed mutagenesis include vectors such as the M13 phage. These phage vectors are readily commercially available and their use is generally well known to those skilled in the art. Double-stranded plasmids are also routinely employed in site directed mutagenesis which eliminates the step of transferring the gene of interest from a plasmid to a phage. Commercially available kits for performing mutagenesis are also available and can be used. Exemplary kits include the QuikChange® sited directed mutagenesis kits (Stratagene, La Jolla, Calif., USA).

In general, site-directed mutagenesis in accordance herewith is performed by first obtaining a single-stranded vector or melting apart of two strands of a double-stranded vector which includes within its sequence a DNA sequence which encodes the desired peptide. An oligonucleotide primer bearing the desired mutated sequence is prepared, generally synthetically. This primer is then annealed with the single-stranded vector, and subjected to DNA polymerizing enzymes such as $E.$ $coli$ polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as $E.$ $coli$ cells, and clones are selected which include recombinant vectors bearing the mutated sequence arrangement.

The preparation of sequence variants of the selected peptide-encoding DNA segments using site-directed mutagenesis is provided as a means of producing potentially useful species and is not meant to be limiting as there are other ways in which sequence variants of peptides and the DNA sequences encoding them may be obtained. For example, recombinant vectors encoding the desired peptide sequence may be treated with mutagenic agents, such as hydroxylamine, to obtain sequence variants.

MtDef4 Antibody Compositions and Methods of Making Antibodies

In particular embodiments, the inventors contemplate the use of antibodies, either monoclonal or polyclonal which bind to the MtDef4 proteins disclosed herein. Means for preparing and characterizing antibodies are well known in the art (See, e.g., Using Antibodies: A Laboratory Manual, Cold Spring Harbor Laboratory, 1999; incorporated herein by reference). The methods for generating monoclonal antibodies (mAbs) generally begin along the same lines as those for preparing polyclonal antibodies. Briefly, a polyclonal antibody is prepared by immunizing an animal with an immunogenic composition in accordance with the present invention and collecting antisera from that immunized animal. A wide range of animal species can be used for the production of antisera. Typically the animal used for production of antisera is a rabbit, a mouse, a rat, a hamster, a guinea pig or a goat. Because of the relatively large blood volume of rabbits, a rabbit is a preferred choice for production of polyclonal antibodies.

As is well known in the art, a given composition may vary in its immunogenicity. It is often necessary therefore to boost the host immune system, as may be achieved by coupling a peptide or protein immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a peptide, polypeptide, or protein to a carrier protein are well known in the art and include using glutaraldehyde, m-maleimidobencoyl-N-hydroxysuccinimide ester, carbodiimide and bis-biazotized benzidine.

As is also well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed $Mycobacterium$ $tuberculosis$), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster, injection may also be given. The process of boosting and titering is repeated until a suitable titer is achieved. When a desired level of immunogenicity is obtained, the immunized animal can be bled and the serum isolated and stored, and/or the animal can be used to generate mAbs.

Monoclonal antibodies (mAbs) may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified antifungal protein, polypeptide or peptide. The immunizing composition is administered in a manner effective to stimulate antibody producing cells. Rodents such as mice and rats are preferred animals, however, the use of rabbit, sheep, or frog cells is also possible. The use of rats may provide certain advantages but mice are preferred, with the BALB/c mouse being most preferred as this is most routinely used and generally gives a higher percentage of stable fusions.

MtDef4 Protein Screening and Detection Kits

The present invention contemplates methods and kits for screening samples suspected of containing MtDef4 proteins or MtDef4 protein-related polypeptides, or cells producing such polypeptides. In the particular embodiments contemplated herein, the methods and kits detect the MtDef4 protein. A kit may contain one or more antibodies of the present invention, and may also contain reagent(s) for detecting an interaction between a sample and an antibody of the present invention. The provided reagent(s) can be radio-, fluorescently- or enzymatically-labeled. The kit can contain a known radiolabeled agent capable of binding or interacting with a nucleic acid or antibody of the present invention.

The reagent(s) of the kit may be provided as a liquid solution, attached to a solid support or as a dried powder. Preferably, when the reagent(s) are provided in a liquid solution, the liquid solution is an aqueous solution. Preferably, when the reagent(s) provided are attached to a solid support, the solid support can be chromatograph media, a test plate having a plurality of wells, or a microscope slide. When the reagent(s) provided are a dry powder, the powder can be reconstituted by the addition of a suitable solvent, which may be provided.

In still further embodiments, the present invention concerns immunodetection methods and associated kits. It is proposed that the MtDef4 proteins or peptides of the present invention may be employed to detect antibodies having reactivity therewith, or, alternatively, antibodies prepared in accordance with the present invention, may be employed to detect MtDef4 proteins or MtDef4 protein-related epitope-containing peptides. In general, these methods will include first obtaining a sample suspected of containing such a protein, peptide or antibody, contacting the sample with an antibody or peptide in accordance with the present invention, as the case may be, under conditions effective to allow the formation of an immunocomplex, and then detecting the presence of the immunocomplex.

In general, the detection of immunocomplex formation is quite well known in the art and may be achieved through the application of numerous approaches. For example, the present invention contemplates the application of ELISA, RIA, immunoblot (e.g., dot blot), indirect immunofluorescence techniques and the like. Generally, immunocomplex formation will be detected through the use of a label, such as a radiolabel or an enzyme tag (such as alkaline phosphatase, horseradish peroxidase, or the like). Of course, one may find additional advantages through the use of a secondary binding ligand such as a second antibody or a biotin/avidin ligand binding arrangement, as is known in the art.

For assaying purposes, it is proposed that virtually any sample suspected of comprising either an MtDef4 protein or peptide or an MtDef4 protein-related peptide or antibody sought to be detected, as the case may be, may be employed. It is contemplated that such embodiments may have application in the titering of antigen or antibody samples, in the selection of hybridomas, and the like. In related embodiments, the present invention contemplates the preparation of kits that may be employed to detect the presence of MtDef4 proteins or related peptides and/or antibodies in a sample. Samples may include cells, cell supernatants, cell suspensions, cell extracts, enzyme fractions, protein extracts, or other cell-free compositions suspected of containing MtDef4 proteins or peptides. Generally speaking, kits in accordance with the present invention will include a suitable MtDef4 protein, peptide or an antibody directed against such a protein or peptide, together with an immunodetection reagent for detecting antibody/antigen complexes, instructions for the use of these materials, and a means for containing the antibody or antigen and reagent. The immunodetection reagent will typically comprise a label associated with the antibody or antigen, or associated with a secondary binding ligand. Exemplary ligands might include a secondary antibody directed against the first antibody or antigen or a biotin or avidin (or streptavidin) ligand having an associated label. Of course, as noted above, a number of exemplary labels are known in the art and all such labels may be employed in connection with the present invention.

The container will generally include a vial into which the antibody, antigen or detection reagent may be placed, and preferably suitably aliquotted. The kits of the present invention will also typically include a means for containing the antibody, antigen, and reagent containers in close confinement for commercial sale. Such containers may include injection or blow-molded plastic containers into which the desired vials are retained.

Compositions Comprising Epitopic Core Sequences

The present invention is also directed to protein or peptide compositions, free from total cells and other peptides, which comprise a purified protein or peptide which incorporates an epitope that is immunologically cross-reactive with one or more anti-MtDef4 protein antibodies. In particular, the invention concerns epitopic core sequences derived from MtDef4 proteins or peptides.

As used herein, the term "incorporating an epitope(s) that is immunologically cross-reactive with one or more anti-MtDef4 protein antibodies" is intended to refer to a peptide or protein antigen which includes a primary, secondary or tertiary structure similar to an epitope located within a MtDef4 protein or polypeptide. The level of similarity will generally be to such a degree that monoclonal or polyclonal antibodies directed against the MtDef4 protein or polypeptide will also bind to, react with, or otherwise recognize, the cross-reactive peptide or protein antigen. Various immunoassay methods may be employed in conjunction with such antibodies, such as, for example, Western blotting, ELISA, RIA, and the like, all of which are known to those of skill in the art.

The identification of MtDef4 protein immunodominant epitopes, and/or their functional equivalents, suitable for use in vaccines is a relatively straightforward matter. For example, one may employ the methods of Hopp, as taught in U.S. Pat. No. 4,554,101, incorporated herein by reference, which teaches the identification and preparation of epitopes from amino acid sequences on the basis of hydrophilicity. The methods described in several other papers, and software programs based thereon, can also be used to identify epitopic core sequences (see, for example, U.S. Pat. No. 4,554,101). The amino acid sequence of these "epitopic core sequences" may then be readily incorporated into peptides, either through the application of peptide synthesis or recombinant technology.

Preferred peptides for use in accordance with the present invention will generally be on the order of about 8 to about 20 amino acids in length, and more preferably about 8 to about 15 amino acids in length. It is proposed that shorter antigenic MtDef4 protein-derived peptides will provide advantages in certain circumstances, for example, in the preparation of immunologic detection assays. Exemplary advantages include the ease of preparation and purification, the relatively low cost and improved reproducibility of production, and advantageous biodistribution.

It is proposed that particular advantages of the present invention may be realized through the preparation of synthetic peptides which include modified and/or extended epitopic/immunogenic core sequences which result in a "universal" epitopic peptide directed to MtDef4 proteins, and in particular to MtDef4-related sequences. These epitopic core sequences are identified herein in particular aspects as hydrophilic regions of the particular polypeptide antigen. It is proposed that these regions represent those which are most likely to promote T-cell or B-cell stimulation, and, hence, elicit specific antibody production.

An epitopic core sequence, as used herein, is a relatively short stretch of amino acids that is "complementary" to, and therefore will bind, antigen binding sites on the MtDef4 protein-directed antibodies disclosed herein. Additionally or alternatively, an epitopic core sequence is one that will elicit antibodies that are cross-reactive with antibodies directed against the peptide compositions of the present invention. Thus, certain epitope core sequences of the present invention may be operationally defined in terms of their ability to compete with or perhaps displace the binding of the desired protein antigen with the corresponding protein-directed antisera.

In general, the size of the polypeptide antigen is not believed to be particularly crucial, so long as it is at least large enough to carry the identified core sequence or sequences. The smallest useful core sequence anticipated by the present disclosure would generally be on the order of about 8 amino acids in length, with sequences on the order of 10 to 20 being more preferred. Thus, this size will generally correspond to the smallest peptide antigens prepared in accordance with the invention. However, the size of the antigen may be larger where desired, so long as it contains a basic epitopic core sequence.

Antifungal Protein Compositions

An antifungal composition, comprising an antifungal plant pathogenic fungus inhibitory amount of one or more of the isolated antifungal polypeptides of the present invention are contemplated. Preferred compositions comprise the amino acid sequence shown in SEQ ID NO:112, and an acceptable carrier. The antifungal composition may be used for inhibiting the growth of, or killing, pathogenic fungi. The compositions can be formulated by conventional methods such as those described in, for example, Winnacker-Kuchler (1986); van Falkenberg (1972-1973); and K. Martens (1979). Necessary formulation aids, such as carriers, inert materials, surfactants, solvents, and other additives are also well known in the art, and are described, for example, in Winnacker-Kuchler (1986). Using these formulations, it is also possible to prepare mixtures of the present antifungal polypeptide with other antifungal active substances, fertilizers and/or growth regulators, etc., in the form of finished formulations or tank mixes.

Antifungal compositions contemplated herein also include those in the form of host cells, such as bacterial and fungal cells, capable of the producing the present antifungal polypeptide, and which can colonize roots and/or leaves of plants. Examples of bacterial cells that can be used in this manner include strains of *Agrobacterium, Arthrobacter, Azospyrillum, Clavibacter, Escherichia, Pseudomonas, Rhizobacterium*, and the like.

Numerous conventional fungal antibiotics and chemical fungicides with which the present antifungal polypeptide can be combined are known in the art and are described in Worthington and Walker (1983). These include, for example, polyoxines, nikkomycines, carboxyamides, aromatic carbohydrates, carboxines, morpholines, inhibitors of sterol biosynthesis, and organophosphorus compounds. Other active ingredients which can be formulated in combination with the present antifungal polypeptide include, for example, insecticides, attractants, sterilizing agents, acaricides, nematicides, and herbicides. U.S. Pat. No. 5,421,839 contains a comprehensive summary of the many active agents with which substances such as the present antifungal polypeptide can be formulated.

Whether alone or in combination with other active agents, the antifungal polypeptides of the present invention should be applied at a concentration in the range of from about 0.1 mg/ml to about 100 mg/ml, preferably between about 5 mg/ml and about 50 mg/ml, at a pH in the range of from about 3 to about 9. Such compositions may be buffered using, for example, phosphate buffers between about 1 mM and 1 M, preferably between about 10 mM and 100 mM, more preferably between about 15 mM and 50 mM.

MtDef4 proteins and biologically functional equivalents are therefore expected to be useful in controlling fungi in a wide variety of plants, exemplified by those in the following genera and species: *Alternaria (Alternaria brassicola; Alternaria solani); Ascochyta (Ascochyta pisi); Botrytis (Botrytis cinerea); Cercospora (Cercospora kikuchii; Cercospora zeae-maydis); Colletotrichum (Colletotrichum lindemuthianum); Diplodia (Diplodia maydis); Erysiphe (Erysiphe graminis* f.sp. *graminis; Erysiphe graminis* f.sp. *hordei); Fusarium (Fusarium nivale; Fusarium oxysporum; Fusarium graminearum; Fusarium culmorum; Fusarium solani; Fusarium moniliforme; Fusarium roseum); Gaeumanomyces (Gaeumanomyces graminis* f.sp. *tritici); Helminthosporium (Helminthosporium turcicum; Helminthosporium carbonum; Helminthosporium maydis); Macrophomina (Macrophomina phaseolina; Maganaporthe grisea); Nectria (Nectria heamatococca); Peronospora (Peronospora manshurica; Peronospora tabacina); Phakopsora (Phakopsora pachyrhizi); Phoma (Phoma betae); Phymatotrichum (Phymatotrichum omnivorum); Phytophthora (Phytophthora cinnamomi; Phytophthora cactorum; Phytophthora phaseoli; Phytophthora parasitica; Phytophthora citrophthora; Phytophthora megasperma* f.sp. *sojae; Phytophthora infestans); Plasmopara (Plasmopara viticola); Podosphaera (Podosphaera leucotricha); Puccinia (Puccinia sorghi; Puccinia struiformis; Puccinia graminis* f.sp. *tritici; Puccinia asparagi; Puccinia recondita; Puccinia arachidis); Pythium (Pythium aphanidermatum); Pyrenophora (Pyrenophora tritici-repentens); Pyricularia (Pyricularia oryzae); Pythium (Pythium ultimum); Rhizoctonia (Rhizoctonia solani; Rhizoctonia cerealis); Scerotium (Scerotium rolfsii); Sclerotinia (Sclerotinia sclerotiorum); Septoria (Septoria lycopersici; Septoria glycines; Septoria nodorum; Septoria tritici); Thielaviopsis (Thielaviopsis basicola); Uncinula (Uncinula necator); Venturia (Venturia inaequalis); Verticillium (Verticillium dahliae; Verticillium alboatrum).*

EXAMPLES

The disclosed embodiments are merely representative of the invention, which may be embodied in various forms. Thus, specific structural and functional details disclosed herein are not to be interpreted as limiting.

Example 1

The Identification of the MtDef4 Defensin Gene Family

Using the nucleotide sequences of MtDef1.1 and MtDef2.1 as query sequences, a screen of The Institute of Genomic Research (TIGR) *Medicago truncatula* GeneIndex (MtGI release 7.0) containing 189,919 ESTs originating from 43 cDNA libraries was performed with successive rounds of searching using the BLASTN and TBLASTX computer programs. (BLASTN compares a nucleotide query sequence against a nucleotide sequence database, while TBLASTN compares a protein query sequence against a nucleotide sequence database that has been translated into all six potential reading frames). This screen led to a discovery of 18 putative defensin genes represented by 10 tentative consensus (TC) sequences and eight singletons (unique non-overlapping sequences). Careful nucleotide alignments revealed that some of the original singletons might indeed be members of already established TCs, and the family has been currently sized to 16 consisting of 10 TCs and 6 singletons. Hanks et al., 2005 disclose a summary of ESTs for the *M. truncatula* TCs and singletons.

The tentative consensus TC85327 sequence revealed only 54.4% nucleotide identity to the MsDef1 gene and 41% amino acid identity to the MsDef1 protein (Gao et al., 2000). Since it was remotely related to the MsDef1 (or MtDef1), MtDef2 and MtDef3 sequences, it was named MtDef4. TC85327 consists of sixty-two ESTs from thirteen different libraries.

Later analyses of the *M. truncatula* employing updated EST sequence database entries provide a similar consensus sequence for the MtDef4 protein. This tentative consensus sequence, designated as TC94214, was assembled from a group of sixty nine (69) ESTs that includes seven (7) sequences additional to the sixty-two (62) ESTs used to assemble the original TC85327 consensus sequence. FIG. 1 shows the TC94214 MtDef4 consensus sequence with exemplary MtDef4 family member amino acid sequences.

A subset of 22 full length, high quality ESTs (i.e. ESTs encompassing the entire MtDef4 coding region) were selected from the TC94214 and aligned to derive a second MtDef4 consensus sequence that includes both the entire MtDef4 proprotein consensus sequence containing both the signal peptide and mature protein (SEQ ID NO: 99). These full length ESTS are shown in Table 3. This analysis indicates that only one of the 22 full length, high quality MtDef4 ESTs encoded a distinct amino acid within the mature MtDef4 peptide sequence. The AL386553 (SEQ ID NO:80) EST encodes a phenylalanine (F) residue rather than a serine (S) residue at residue 59 in the consensus sequence (SEQ ID NO: 99). All other encoded amino acid sequence variants occurred in the signal peptide sequence. The putative signal peptide sequences are underlined and shown in lowercase in Table 3. The underlined Genbank Accession number (i.e. the two letter code immediately followed by the six digit number, such as "AL385796") of corresponding EST nucleotide sequence is shown for each of the deduced amino acid sequences.

TABLE 3

Full length, High Quality MtDef4 EST Deduced Amino Acid Sequence Alignment and Consensus AL385796
marsvflvstifvfllvlvatgpsmvaeaRTCESQSHKFKGPCASDHNCASVCQTERFSGGHCRGFRRRCFCTTHC-
SEQ ID NO: 77

AW573770
marsvslvftifvflllvvatgpsmvaeaRTCESQSHKFKGPCASDHNCASVCQTERFSGGHCRGFRRRCFCTTHC-
SEQ ID NO: 78

BI310743
mqsfssfqftifvfllllvatgpsmvaeaRTCESQSHKFKGPCASDHNCASVCQTERFSGGHCRGFRRRCFCTTHC-
SEQ ID NO: 79

AL386553
marsvplvstifvfllllvatgpsmvaeaRTCESQSHKFKGPCASDHNCASVCQTERFFGGHCRGFRRRCFCTTHC-
SEQ ID NO: 80

AL386552
marsvplvstifvfllllvatgpsmvaeaRTCESQSHKFKGPCASDHNCASVCQTERFSGGHCRGFRRRCFCTTHC-
SEQ ID NO: 81

AL387540
marsvplvstifvfllllvatgpsmvaeaRTCESQSHKFKGPCASDHNCASVCQTERFSGGHCRGFRRRCFCTTHC-
SEQ ID NO: 82

AL387541
marsvplvstifvfllllvatgpsmvaeaRTCESQSHKFKGPCASDHNCASVCQTERFSGGHCRGFRRRCFCTTHC-
SEQ ID NO: 83

AW287924
marsvplvstifvfllllvatgpsmvaeaRTCESQSHKFKGPCASDHNCASVCQTERFSGGHCRGFRRRCFCTTHC-
SEQ ID NO: 84

BE941578
marsvplvstifvfllllvatgpsmvaeaRTCESQSHKFKGPCASDHNCASVCQTERFSGGHCRGFRRRCFCTTHC-
SEQ ID NO: 85

BF636345
marsvplvstifvfllllvatgpsmvaeaRTCESQSHKFKGPCASDHNCASVCQTERFSGGHCRGFRRRCFCTTHC-
SEQ ID NO: 86

BE999096
marsvplvstifvfllllvatgpsmvgeaRTCESQSHKFKGPCASDHNCASVCQTERFSGGHCRGFRRRCFCTTHC-
SEQ ID NO: 87

BI263014
marsvplvstifvfllllvatgpsmvaeaRTCESQSHKFKGPCASDHNCASVCQTERFSGGHCRGFRRRCFCTTHC-
SEQ ID NO: 88

BI270683
marsvplvstifvfllllvatgpsmvaeaRTCESQSHKFKGPCASDHNCASVCQTERFSGGHCRGFRRRCFCTTHC-
SEQ ID NO: 89

BI310744
marsvplvstifvfllllvatgpsmvaeaRTCESQSHKFKGPCASDHNCASVCQTERFSGGHCRGFRRRCFCTTHC-
SEQ ID NO: 90

BQ144133
marsvplvstifvfllllvatgpsmvaeaRTCESQSHKFKGPCASDHNCASVCQTERFSGGHCRGFRRRCFCTTHC-
SEQ ID NO: 91

TABLE 3-continued

Full length, High Quality MtDef4 EST Deduced Amino Acid Sequence Alignment and Consensus BQ145044
marsvplvstifvfllllvatgpsmvaeaRTCESQSHKFKGPCASDHNCASVCQTERFSGGHCRGFRRRCFCTTHC-
SEQ ID NO: 92

BQ153111
marsvplvstifvfllllvatgpsmvaeaRTCESQSHKFKGPCASDHNCASVCQTERFSGGHCRGFRRRCFCTTHC-
SEQ ID NO: 93

BQ154835
marsvplvstifvfllllvatgpsmvaeaRTCESQSHKFKGPCASDHNCASVCQTERFSGGHCRGFRRRCFCTTHC-
SEQ ID NO: 94

BQ157484
marsvplvstifvfllllvatgpsmvaeaRTCESQSHKFKGPCASDHNCASVCQTERFSGGHCRGFRRRCFCTTHC-
SEQ ID NO: 95

BQ157772
marsvplvstifvfllllvatgpsmvaeaRTCESQSHKFKGPCASDHNCASVCQTERFSGGHCRGFRRRCFCTTHC-
SEQ ID NO: 96

BQ159085
marsvplvstifvfllllvatgpsmvaeaRTCESQSHKFKGPCASDHNCASVCQTERFSGGHCRGFRRRCFCTTHC-
SEQ ID NO: 97

CX535058
marsvplvstifvfllllvatgpsmvaeaRTCESQSHKFKGPCASDHNCASVCQTERFSGGHCRGFRRRCFCTTHC-
SEQ ID NO: 98

Consensus
marsvplvstifvfllllvatgpsmvaeaRTCESQSHKFKGPCASDHNCASVCQTERFSGGHCRGFRRRCFCTTHC-
SEQ ID NO: 99

Analysis of the 22 high quality MtDef4 ESTs led to the identification of five (5) unique ESTs that are shown in Table 4. In this table the unique residues are underlined and signal peptide sequences are indicated in the lower case. The underlined GenBank Accession number (i.e. the two letter code immediately followed by the six digit number, such as "AL385796") of corresponding EST nucleotide sequence is shown for each of the deduced amino acid sequences. The nucleotide sequences for each of the unique ESTs are also provided as follows: AL386552 is SEQ ID NO:100, AL385796 is SEQ ID NO:101, AL386553 is SEQ ID NO:102, AW573770 is SEQ ID NO:103, and BE999096 is SEQ ID NO:104.

TABLE 4

Unique MtDef4 EST-encoded polypeptides

Consensus
marsvplvstifvfllllvatgpsmvaeaRTCESQSHKFKGPCASDHNCASVCQTERFSGGHCRGFRRRCFCTTHC
SEQ ID NO: 99

AL386552
marsvplvstifvfllllvatgpsmvaeaRTCESQSHKFKGPCASDHNCASVCQTERFSGGHCRGFRRRCFCTTHC
SEQ ID NO: 81

AL385796 (1)
marsvflvstifvfllvlvatgpsmvaeaRTCESQSHKFKGPCASDHNCASVCQTERFSGGHCRGFRRRCFCTTHC
SEQ ID NO: 77

AL386553 (1)
marsvplvstifvfllllvatgpsmvaeaRTCESQSHKFKGPCASDHNCASVCQTERFFGGHCRGFRRRCFCTTHC
SEQ ID NO: 80

AL386553 (Mature Peptide)
RTCESQSHKFKGPCASDHNCASVCQTERFFGGHCRGFRRRCFCTTHC
SEQ ID NO: 105

AW573770
marsvslvftifvflllvvatgpsmvaeaRTCESQSHKFKGPCASDHNCASVCQTERFSGGHCRGFRRRCFCTTHC
SEQ ID NO: 78

TABLE 4-continued

Unique MtDef4 EST-encoded polypeptides

BE999096
marsvplvstifvfllllvatgpsmvgeaRTCESQSHKFKGPCASDHNCASVCQTERFSGGHCRGFRRRCFCTTHC
SEQ ID NO: 87

Example 2

Cloning of an MtDef4 Gene Family Member and Expression in *Pichia*

Genomic DNA isolated from *M. truncatula* was used as a template for PCR amplification of the MtDef4 gene(s). The forward primer, 5'-ATGGTGGCAGAAGCAAGAA-3' (SEQ ID NO:106) and the reverse primer, 5'-CAAAAGATCTACG-GACGG-3' (SEQ ID NO:107) were used for PCR amplification. The PCR conditions were 30 cycles with a 90 second 94° C. denaturation step, a 30 sec 45° C. annealing step and a 60 second 74° C. extension step. Four PCR products of 302 bp, 402 bp, 475 bp, and 506 bp were observed on an agarose gel and were cloned into the pCR2.1-TOPO™ vector (Invitrogen, Carlsbad, Calif., USA) and sequenced using the Big Dye® Terminator Mix on an ABI Prism 377 automated DNA sequencer. Only three of these genomic PCR products were found to encode defensin proteins and were named MtDef4.1 (SEQ ID NO:108), MtDef4.2 (SEQ ID NO:109) and MtDef4.3 (SEQ ID NO:110). Comparison of these sequences with the MtDef4 EST sequences of TC94214 revealed that the PCR-derived genomic clones contained an intron sequence. The peptides encoded by each of the MtDef4.1, MtDef4.2 and MtDef4.3 genomic PCR clones were deduced on the computer by removing the intron sequence and translating the corresponding deduced cDNA sequence. The deduced cDNA sequences include those for MtDef4.1 (SEQ ID NO:126), MtDef4.2 (SEQ ID NO:124), and MtDef4.3 (SEQ ID NO:143). MtDef4.1 (SEQ ID NO:108) encodes a proprotein (SEQ ID NO:111) that contains a signal peptide of 29 amino acids (SEQ ID NO:118) and a mature defensin peptide of 47 amino acids (SEQ ID NO:112). The MtDef4.2 and MtDef4.3 protein sequences were more closely related to each other than to MtDef4.1. Conceptual splicing and translation of the MtDef4.1, MtDef4.2, and MtDef4.3 nucleotide sequences using the Vector NTI computer program (Invitrogen, Carlsbad, Calif., USA) showed that the percentage of amino acid sequence identity was higher than that of nucleotide sequence identity.

TABLE 5

Deduced Amino Acid Sequences of MtDef4.1, MtDef4.2, MtDef4.3

MtDef4.1
marsvplvstifvfllllvat--gpsmvaeaRTCESQSHKFKGPCASDHNCASVCQTERFSGGHCRGFRRRCFCTTHC-
SEQ ID NO: 111

MtDef4.1 (H33) (Mature Peptide)
RTCESQSHKFKGPCASDHNCASVCQTERFSGGHCRGFRRRCFCTTHC
SEQ ID NO: 112

MtDef4.2
marsvplvstifvfflllivatemgpsmva-aRTCETPSNSFKGACFSDTNCASVCQTEGFPGGHCEGFRQRCFCTTHC-
SEQ ID NO: 113

MtDef4.2 (Mature Peptide)
RTCETPSNSFKGACFSDTNCASVCQTEGFPGGHCEGFRQRCFCTTHC
SEQ ID NO: 114

MtDef4.3
marsvplvstifvfflllvatemgpimvaeaRTCETPSNNFKGLCVSDTNCASVCQTEGFPGGHCEGFRQRCFCTTHC-
SEQ ID NO: 115

MtDef4.3 (Mature Peptide)
RTCETPSNNFKGLCVSDTNCASVCQTEGFPGGHCEGFRQRCFCTTHC
SEQ ID NO: 116

For large scale isolation of MtDef4 proteins, the MtDef4.1 gene and a variant thereof were expressed in *Pichia pastoris*. The gene was cloned into the pPIC9 vector (Invitrogen, Carlsbad, Calif.) which allows methanol-inducible expression and secretion of the protein in the growth medium of *P. pastoris*. The DNA sequence encoding mature MtDef4.1 protein was cloned in frame with the initiation codon of the yeast α-factor signal sequence and propeptide at the XhoI restriction site of pPIC9. More specifically, an XhoI site was introduced at the 5' end of the MtDef4.1 mature coding region such that the N-terminal Arg (R) of mature MtDef4.1 protein was fused to the KEX2 protease cleavage site located at the C-terminus of the yeast α-factor signal sequence and propeptide. The MtDef4.1 defensin sequence used in the *Pichia* vector was obtained by performing PCR on the MtDef4.1 genomic clone sequence (SEQ ID NO:108) using primers RS21 (5-AGAAAAGAAGAACTTGTGAGTCA-CAAAGTCACAAATTC-3', SEQ ID NO:139) and RS22 (5-GATTACGAATTCTTAACAATGTGTAGTG-CAAAAGCATCTACGACG; SEQ ID NO:140).

The resulting vector contained the coding region of the mature MtDef4.1 defensin sequence (SEQ ID NO:112) fused in frame with the α-factor signal sequence downstream of the P. pastoris alcohol oxidase promoter as well as a HIS4 selectable marker gene (FIG. 2). The sequence of the MtDef4.1 Pichia expression cassette comprising the operably linked AOX1 promoter, the α-factor signal sequence, the mature MtDef4.1 defensin sequence, and the AOX1 polyadenylation sequence are provided in SEQ ID NO:157).

Another MtDef4.1 clone obtained from the PCR reactions with the RS21 and RS22 primers encoded a mature MtDef4.1 peptide sequence that differed from the mature MtDef4.1 sequence (SEQ ID NO:112) at one amino acid residue. More specifically, the MtDef4.1 (H33R) clone encodes histidine (His) to arginine (Arg) substitution at position 33 (SEQ ID NO:125). This clone is therefore designated MtDef4.1 (H33R). The mature MtDef4.1 (H33R) coding sequence is provided in SEQ ID NO:144. The sequence of the MtDef4.1 Pichia expression cassette comprising the operably linked AOX1 promoter, the α-factor signal sequence, the mature MtDef4.1 (H33R) defensin sequence, and the AOX1 polyadenylation sequence are provided in SEQ ID NO: 73.

Both of the MtDef4 yeast vectors were linearized by digestion with SalI and introduced into histidine auxotroph strain GS115 by electroporation. Transformants where the MtDef4.1 Pichia expression cassette and the HIS4 selectable marker gene had integrated into the genome of the P. pastoris (i.e. His+ transformants) were selected by plating on minimal dextrose plates that lacked histidine.

The individual transformants were grown in buffered glycerol media and the expression of the MtDef4.1 or MtDef4.1 (H33R) protein was induced by addition of methanol to the culture. In brief, overnight cultures of the transformed Pichia lines were induced with methanol every 24 hours for a total of 7 days at a temperature of 29° C. This procedure is essentially as per the directions of the supplier (Invitrogen, Carlsbad, Calif.).

MtDef4.1 or MtDef4.1 (H33R) protein was purified from the growth medium by first removing the cells by centrifugation (4,000 g for 5 minutes), adjusting the cell-free media to 25 mM sodium acetate, pH 6.0, and then passing the media through CM-Sephadex C-25 cation-exchange resin (Amersham Biosciences, Piscataway, N.J.) equilibrated with 25 mM sodium acetate, pH 6.0. Resin was extensively washed with binding buffer (25 mM sodium acetate, pH 6.0), and the bound protein was then eluted in 1 M NaCl, 50 mM Tris, pH 7.6. Fractions containing the protein were manually collected and analyzed by SDS-PAGE for the presence of MtDef4.1 or MtDef4.1 (H33R). Fractions containing the defensin protein were concentrated using an Amicon Stirred-Cell II™ ultrafiltration system (Millipore, Bedford, Mass.) with a 3-kD cutoff membrane and dialyzed against 10 mM Tris, pH 7.6. The identities of MtDef4.1 and MtDef4.1 (H33R) were confirmed by mass spectrometry. In brief, the purified protein was subjected to analysis on a Quadrupole-Time-of-Flight (QTOF) mass spectrometer (Applied Biosystems, Foster City, Calif.). The MW molecular weight of MtDef4.1 was determined to be 5315.77 and the molecular weight of MtDef4.1 (H33R) was determined to be 5334.98. These masses are within 0.5 daltons of the predicted mass of the MtDef4.1 and MtDef4.1 (H33R) folded, cysteine-bridged mature defensin peptides.

Example 3

Antifungal Activity of MtDef4.1 (H33R)

Figure 3:
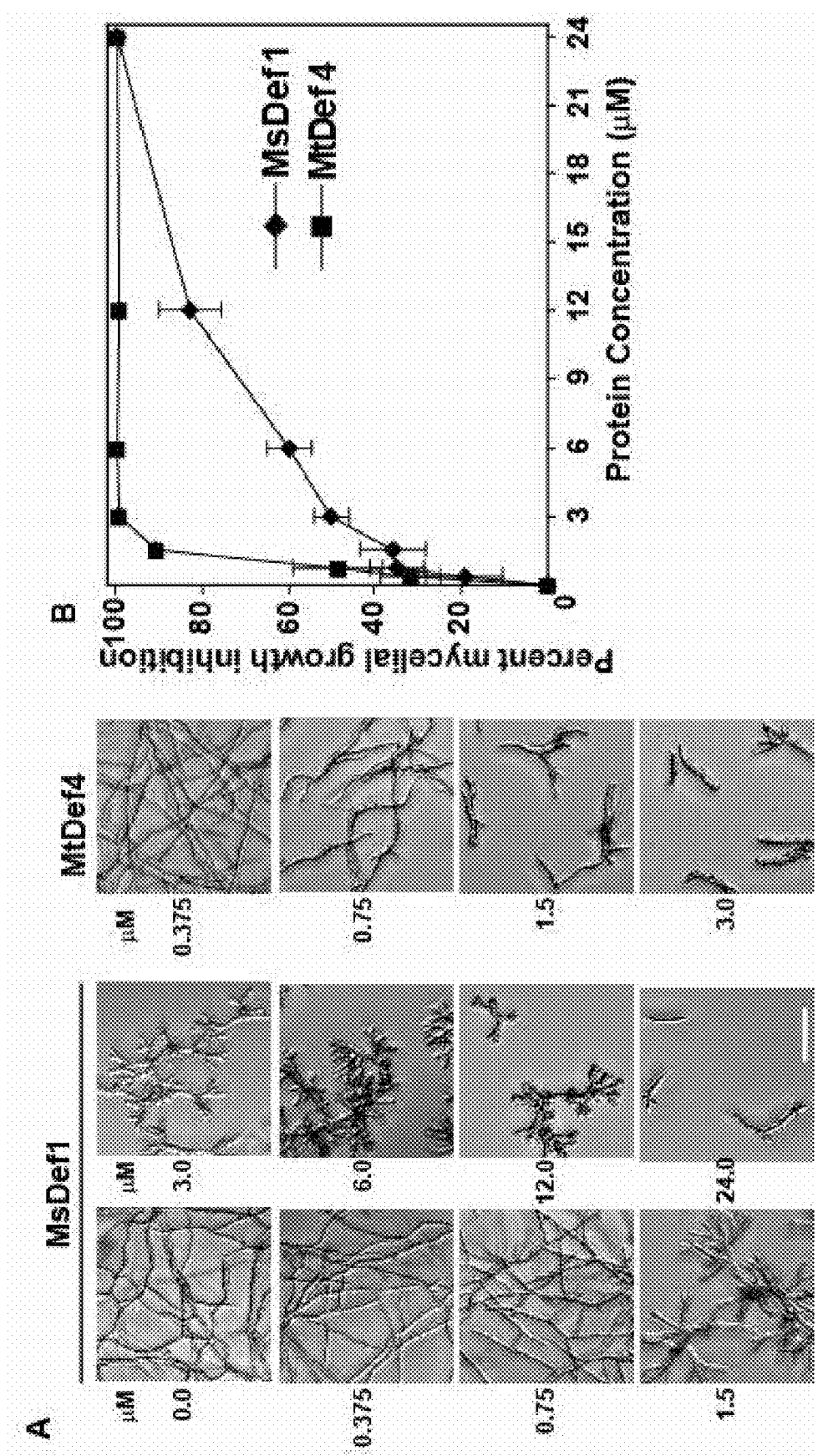
FIG. 3 shows the potent antifungal activity of the MsDef1 (AlfAFP) and MtDef4.1 (H33R) proteins against *F. graminearum* PH-1. The mature MtDef4.1 (H33R) protein

Medicago defensins differ substantially in their in vitro antifungal activity against F. graminareum and F. verticillioides. The antifungal activity of MtDef4.1 (H33R) was determined by measuring the inhibition of fungal hyphal growth in an in vitro assay using 96-well microtiter plates and compared with that of MsDef1 (FIG. 3). Spore suspensions of F. graminearum and F. verticillioides were prepared in 2× synthetic low-salt fungal medium (Liang et al., 2001) at a concentration of 40,000 spores per ml. Fifty microliter of spore suspension and 50 µl of different concentrations of each defensin were added to each well of a microtiter plate. The antifungal assay plates were incubated at room temperature (22-24° C.) in the dark for 16 hours. MsDef1 inhibits the growth of F. verticillioides with an IC$_{50}$ of 2 µM, whereas MtDef4.1 (H33R) inhibits the growth of this fungus with an IC$_{50}$ of 0.5 µm. (Table 6). MsDef1 inhibits the growth of F. graminearum with an IC$_{50}$ of 2 µM, whereas MtDef4.1 (H33R) inhibits the growth of this fungus with an IC$_{50}$ of 0.75 µm. Furthermore, MsDef1 induces strong hyperbranching of the fungal hyphae, whereas MtDef4.1 (H33R) does not. Thus, MtDef4.1 (H33R) is a more potent antifungal defensin against both F. graminareum and F. verticillioides than MsDef1, and likely inhibits these fungi with a different mode of action.

TABLE 6

In vitro antifungal activity of defensins

| Proteins | F. graminearum | | | F. verticillioides | | |
|---|---|---|---|---|---|---|
| | MIC (µm) | IC$_{50}$ (µm) | IC (µm) | MIC (µm) | IC$_{50}$ (µm) | IC (µm) |
| MsDef1 | 0.375 | 2 | >24 | 0.5-1.0 | 2 | >24 |
| MtDef4.1 (H33R) | 0.25 | 0.75 | 6 | 0.25 | 0.5 | 1.5 |

MIC = minimum inhibitory concentration
IC$_{50}$ = concentration at which 50% of the growth is inhibited
IC = complete inhibitory concentration for spore germination Example 4

Comparison of Biological Activity of Mt Def4.1 (SEQ ID NO:112) and MtDef4.1 (H33R) (SEQ ID NO:125)

To compare the biological activity of Mt Def4.1 (SEQ ID NO:112) and MtDef4.1 (H33R) (SEQ ID NO:125), the mature proteins were first obtained by culturing Pichia transformed with the respective Pichia expression vectors (SEQ ID NO:145 and SEQ ID NO:73). Production of mature MtDef4 protein was effected by inducing the transformed Pichia with methanol, harvesting the culture media, and isolating the mature MtDef4 proteins essentially as previously described in Example 3. The purified MtDef4 proteins were then assayed for inhibition of F. graminearum essentially as previously described in Example 3.

Figure 4:
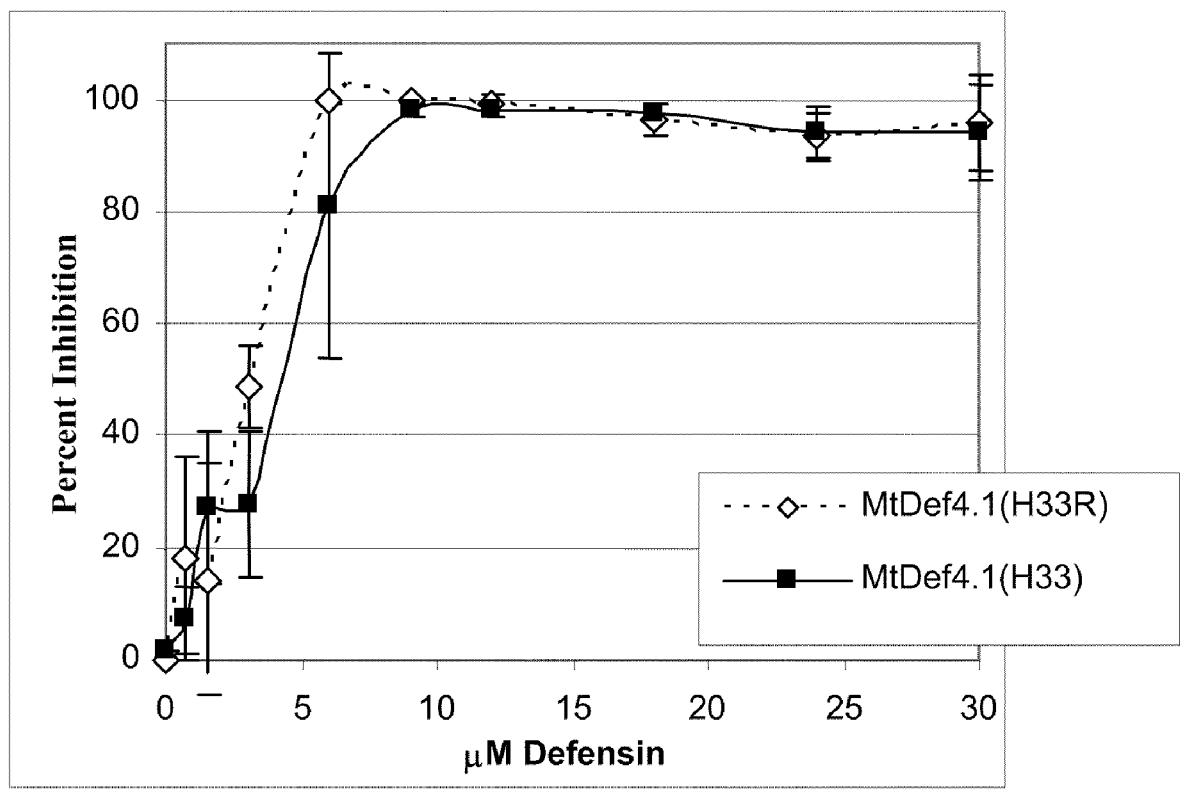

As shown in FIG. 4, the MtDef4.1 and MtDef4.1 (H33R) proteins exhibited a similar biological activity when assayed for inhibition of F. graminearum.

Example 5

Demonstration of a Distinct Mode of Action for MtDef4.1 (H33R) and MsDef1

Two cysteine-rich antifungal defensins, MsDef1 and MtDef4.1 (H33R) from *Medicago* sp., share 41% amino acid sequence identity and both defensins inhibit the growth of the fungal pathogen *Fusarium graminearum* at micromolar concentrations. To compare the mode of action of MsDef1 to the mode of action of an MtDef4 protein, several insertional mutants of *F. graminearum* that exhibit hypersensitivity to MsDef1 were assayed for sensitivity to MsDef1 and MtDef4.1 (H33R).

MsDef1 and MtDef4.1 (H33R) were expressed in the yeast *Pichia pastoris* and purified from the growth medium as described previously in Spelbrink et al., 2004 and Example 2. MtDef4.1 (H33R) protein sharing 41% identity with MsDef1 was also expressed in *P. pastoris* and purified from the growth medium in a similar manner. The identity of each defensin was confirmed by MALDI-MS in the positive ion mode using the matrices α-cyano-4-hydroxycinnamic acid (reflector mode) and sinapic acid (linear mode). All defensins were found to be pure and have the predicted mass-to-charge ratio.

In vitro antifungal assays using two-fold serial dilution of each defensin were carried out as described (Liang et al., 2001; Spelbrink et al., 2004). Bright field images were made using the transmitted light channel in a Zeiss LSM 510 META confocal microscope. Fungal growth inhibition was also quantitated spectrophotometrically 36 hr after the addition of each defensin (Broekaert et al., 1990). The concentration required for 50% growth inhibition was determined as the $IC_{50}$ value.

About 4,800 random insertional mutants generated using the restriction enzyme-mediated integration (REMI) approach (Seong et al., 2005) were used to obtain the fungal mutants with hypersensitivity to MsDef1. *F. graminearum* wild-type PH-1 and mutants generated from PH-1 were routinely cultured in complete medium (CM) (Correll et al., 1987) or V8 juice agar medium (Correll et al., 1987). For conidiation assays, fungal cultures were grown in the carboxymethyl cellulose (CMC) medium (Cappelini and Peterson, 1965). These REMI transformants were successfully used previously to isolate eleven pathogenicity mutants (Seong et al., 2005). In order to identify mutants exhibiting hypersensitivity or resistance to MsDef1 and/or MtDef4.1 (H33R) with certainty, $IC_{50}$ values (effective concentration for 50% growth inhibition) of these defensins against *F. graminearum* wild-type PH-1 were ascertained based on growth inhibition observed microscopically and by measuring absorbance of the culture at A595 using a microplate reader (Broekaert et al., 1990). Two different concentrations of MsDef1 at 1.5 M and 3 µM were used to screen 4,800 REMI transformants for altered sensitivity to MsDef1. These transformants were concomitantly screened for altered sensitivity to MtDef4.1 (H33R) at two different concentrations of 0.75 and 1.5 µM. *F. graminearum* mutants (REMI mutants) were examined for either hypersensitivity or resistance to MsDef1 and/or MtDef4.1 (H33R). At the concentrations tested, none of the 4,800 REMI transformants showed resistance to either MsDef1 or MtDef4.1 (H33R). However, several mutants were identified that exhibited hypersensitivity to MsDef1, but not to MtDef4.1 (H33R) Two mutants, esd1 and esd2, (for enhanced sensitivity to defensin) were chosen for further analysis.

Figure 5:
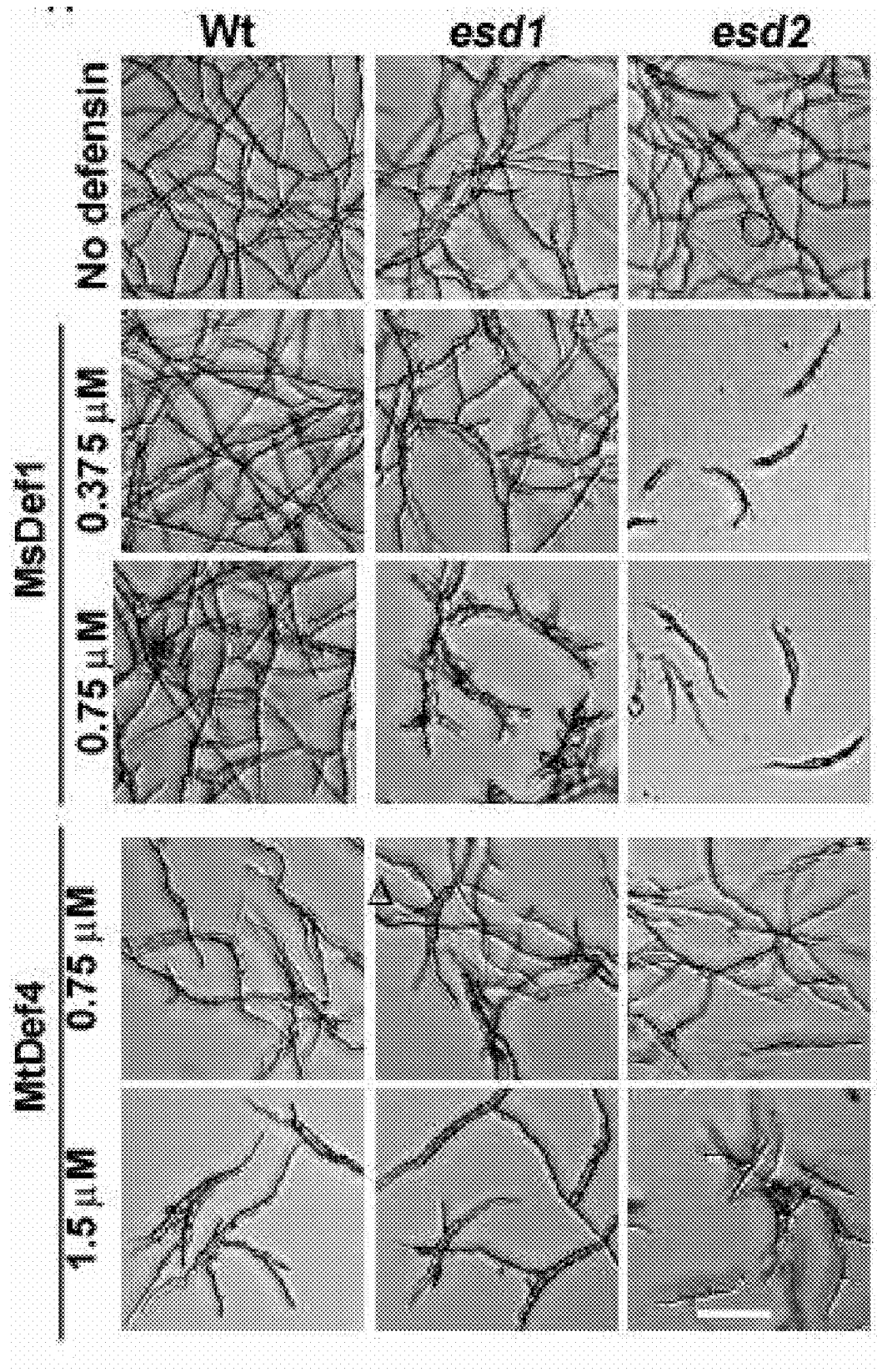

Both of the esd mutants, esd1 and esd2, were more sensitive to MsDef1 than the wildtype PH-1 strain. The esd1 mutant was completely inhibited at 1.5 µM MsDef1 (FIG. 5). At concentrations of 6 and 12 µM, it exhibited spore bulging which was not observed at lower concentrations (data not shown). The mutant esd2 showed much greater sensitivity to MsDef1 than esd1. At 0.375 µM, MsDef1 inhibited germination of esd2 conidia without causing any distortion in their size or shape (FIG. 5), but at 2 µM MsDef1, spores became bulged and individual cells in the spores (6-celled spore) were visible clearly indicating hypersensitivity to MsDef1 (data not shown). In contrast, the wild type PH-1 strain, the esd1 mutant and esd2 mutant were are equally sensitive to MtDef4.1 (H33R). The existence of these two distinct mutants that display selective hypersensitivity to MsDef1 but not MtDef4 indicates that these two defensin proteins have distinct modes of action.

Example 6

Generation of Transgenic Wheat Containing the MtDef4.1 (H33R) Gene

Figure 7:
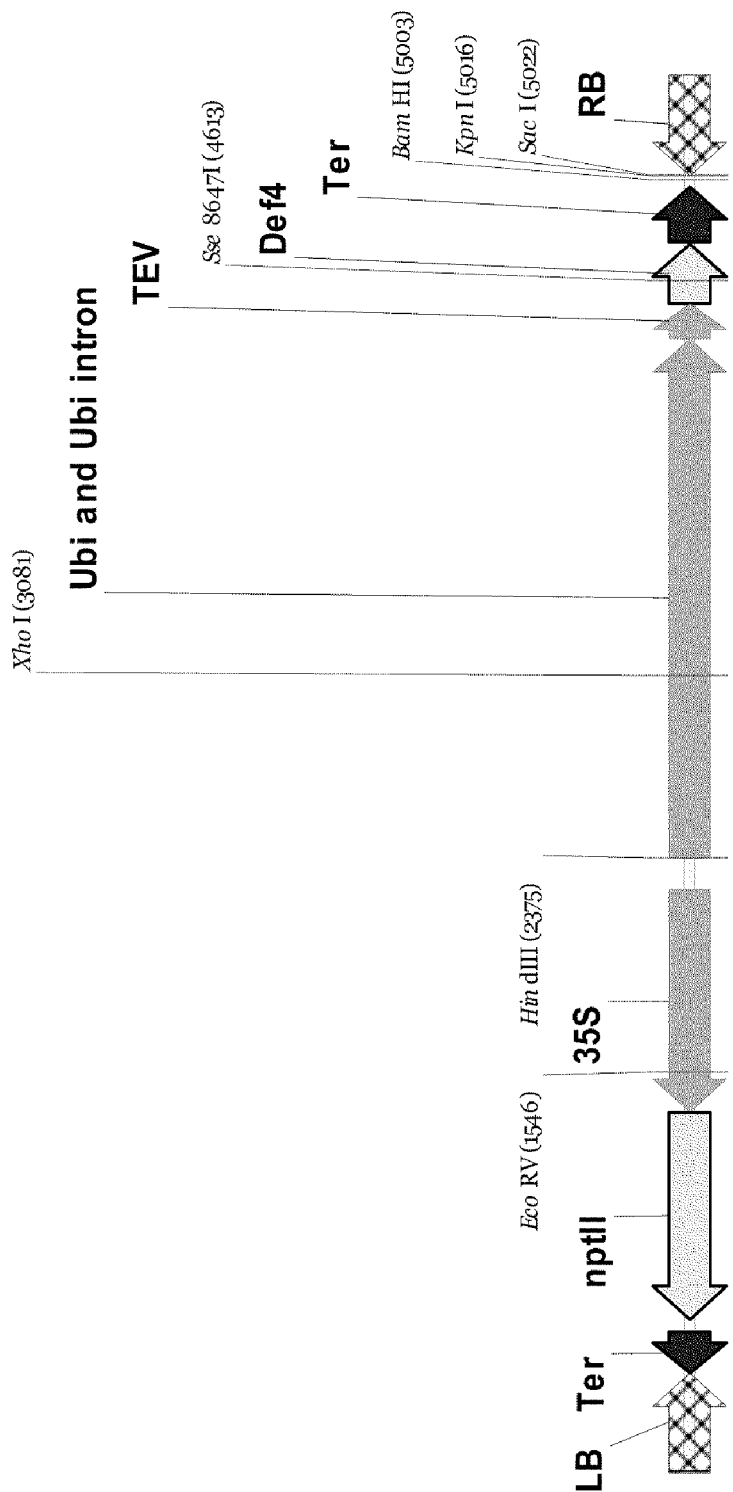

For expression of the MtDef4.1 (H33R) in wheat, a MtDef4 gene was synthesized based on monocot preferred codons such that the amino acid sequence of the MtDef4.1 (H33R) signal peptide and mature protein remained unchanged (FIG. 6; SEQ ID NOS:72 and 151). The 239 bp synthetic MtDef4 gene (SEQ ID NO:72) was obtained from the GenScript Corporation (Piscataway, N.J., USA). The synthetic MtDef4.1 (H33R) gene was placed between the maize ubiquitin (Ubi1) promoter/intron and CaMV 35S polyadenylation signal sequence and cloned between the T-DNA borders of the binary plant expression vector pZP211 (Hajdukiewicz et al., 1994) as shown in FIG. 7. The sequence of the MtDef4.1 (H33R) plant expression cassette comprising the operably linked maize ubiquitin (Ubi1) promoter/intron, the TEV 5-prime enhancer, the MtDef4.1 (H33R) defensin sequence encoding the signal peptide and mature protein, and the CaMV 35S polyadenylation sequence are provided in SEQ ID NO:74.

The pZP212 vector containing the synthetic MtDef4.1 (H33R) gene and a neomycin phosphotransferase selectable marker gene (nptII) was introduced into head scab disease susceptible "Bobwhite" and partially resistant XC wheat cultivars.

Transgenic Bobwhite and XC wheat cultivars that comprise a DNA construct for expression of MtDef4 in plants have been obtained. The transgenic wheat have been obtained as described in this example or by use of substantially equivalent MtDef4 plant expression vectors and transformation techniques. Transgenic plants that are homozygous for the MtDef4 DNA construct insertion have been obtained. Transgenic wheat plants in the T2 generation have also been obtained.

Example 7

Identification of Transgenic Wheat that Inhibit Growth of Plant Pathogenic Fungi At least twenty seeds from each homozygous line as well as seeds from control plants (i.e. the Bobwhite or XC cultivars lacking the MtDef4 transgene) will be sown. Three spikes (heads) from each plant will be inoculated with *Fusarium graminearum* (strain PH-1) spore suspension ($5 \times 10^4$ spores/ml). About three (3) single spikelet/spike(s) on each of the MtDef4 and control wheat plants will be inoculated using a single-floret inoculation method. The number of scabby/infected spikelets on the inoculated spikes will be visually counted on 5, 9, 13, 17, 21 and 25 days post inoculation (dpi), respectively. The infected spikelets (%)=average of 60 spikes from 20 plants/wheat line will be calculated. Statistical significance analysis will be done using Student t-test and ANOVA. A significant decrease in the percentage of infected spikes will be observed in the MtDef4 transgenic wheat plants relative to the control plants that do not express MtDef4.

Example 8

Generation of Transgenic Corn Containing the Chimeric MtDef4 Gene

The monocot optimized MtDef4.1 (H33R) construct (SEQ ID: 72) in the pZP212 vector was also used to transform maize inbred H99 using the method in Sidorov et al 2006. This MtDef4.1 (H33R) plant expression cassette comprising the operably linked maize ubiquitin (Ubi1) promoter/intron, the TEV 5-prime enhancer, the MtDef4.1 (H33R) defensin sequence encoding the signal peptide and mature protein, and the CaMV35S polyadenylation sequence (SEQ ID NO: 74) was also subcloned into the pTF101 vector and used for *Agrobacterium*-mediated transformation of maize HiII immature embryos using the method in Frame et al., 2002. Transgenic plants have been received and evaluated by PCR for presence of the MtDef4.1H33R cassette. Transgenic maize plants that are positive for the desired MtDef4 DNA construct have been obtained. These transgenic plants were selfed or crossed into the B73 background to obtain T1 (progeny from selfing) and F1 (progeny outcrossing) seed.

Example 9

Evaluation of Transgenic Maize for Inhibition of Fungal Growth

Transgenic maize plants that are positive for the desired MtDef4 DNA construct will be selfed or crossed into the B73 background to obtain T1 (progeny from selfing) and F1 (progeny outcrossing) seed. T1 and F1 seeds will be produced for numerous independent transgenic events.

Transgenic maize plants in the T1 generation will be assayed for expression of MtDef4 protein through use of an MtDef4 antibody. Transgenic maize plants in the T3 generation will be assayed for fungal disease resistance in the greenhouse by measuring the amount of mycotoxins produced when the plants are infected with mycotoxin producing *Fusarium* sp.

Example 10

Generation of the MtDef4 Cysteine Variants

The processed and properly folded MtDef4 protein is predicted to contain 4 disulfide bridges, based on of the homology to other defensins whose structures have been solved (Thomma et al., 2002; Lay and Andersen, 2005). While not being limited by theory, it is believed that MtDef4 cysteine variants that lack one or more disulfide linkages may be desirable for use in transgenic plants that are ultimately used as animal feed or as food for human consumption as such variants are predicted to be more readily digested by animals or humans that consume the transgenic plant products. MtDef4 variant proteins that have shorter half-lives in the digestive tracts of animals or humans are in theory anticipated to have less potential to become food allergens.

The predicted pairing of disulfide bonds in MtDef4 is between cysteine residues 3 and 47, 14 and 34, 20 and 41, and 24 and 43. Thus, Cys-pair 1 is predicted to be formed by a Cys3-Cys47 disulfide bond, Cys-pair 2 is predicted to be formed by a Cys14-Cys34 disulfide bond, Cys-pair 3 is predicted to be formed by a Cys20-Cys41 disulfide bond, and Cys-pair 4 is predicted to be formed by a Cys24-Cys43 disulfide bond. Based on this prediction, paired cysteines were changed to serine residues using the Stratagene QuikChange Multi Site-Directed Mutagenesis Kit (Stratagene, La Jolla, Calif.) according to manufacturer's directions and the primers in Table 9.

TABLE 9

Primers Used to Obtain MtDef4 Cys Variants

| Cys pair | Primer | Primer Sequence | Cys number | Residue number |
|---|---|---|---|---|
| 1 | AKS0038-C1S (SEQ ID NO: 127) | CTCGAGAAAAGAAGAACTTCTGAGTCACAAAGTCACAAATTC | Cys1 | Cys3Ser |
| 2 | AKS0040-C2S (SEQ ID NO: 128) | TTCAAAGGGCCATCTGCTAGTGATCACAACTG | Cys2 | Cys14Ser |
| 3 | AKS0042-C3S (SEQ ID NO: 129) | GCTAGTGATCACAACTCTGCTTCTGTGTGCCAAAC | Cys3 | Cys20Ser |
| 4 | AKS0044-C4S (SEQ ID NO: 130) | CAACTGTGCTTCTGTGTCCCAAACAGAACG | Cys4 | Cys24Ser |
| 1 | AKS0039-C8S (SEQ ID NO: 131) | TGCTTTTGCACTACACATTCTTAAGAATTCCCCTAGGGC | Cys8 | Cys47Ser |
| 2 | AKS0041-C5S (SEQ ID NO: 132) | CTGGAGGACGCTCCCGTGGATTCCG | Cys5 | Cys34Ser |
| 3 | AKS0043-C6S (SEQ ID NO: 133) | GGATTCCGTCGTAGATCCTTTTGCACTACACATTG | Cys6 | Cys41Ser |

TABLE 9-continued

Primers Used to Obtain MtDef4 Cys Variants

| Cys pair | Primer | Primer Sequence | Cys number | Residue number |
|---|---|---|---|---|
| 4 | AKS0045-C7S (SEQ ID NO: 134) | CCGTCGTAGATGCTTTTCCACTACACATTGTTAAG | Cys7 | Cys43Ser |

The pPIC9-MtDef4.1 (H33R) construct for *Pichia* expression described previously was used as template in the mutagenesis reactions as this construct was known to express well in *Pichia* (see FIG. 2). In this construct, the MtDef4.1 (H33R) mature coding region is fused to the yeast α-factor signal sequence and propeptide such that the N-terminal Arg (R) of mature MtDef4.1 (H33R) protein was fused to the KEX2 protease cleavage site located at the C-terminus of the yeast α-factor signal sequence and propeptide. The four constructs were sequenced and transformed into *P. pastoris* strain GS115. Transformed *Pichia* were grown and induced with methanol. The cysteine variant MtDef4.1 (H33R) proteins were purified as in Spelbrink et al. 2004. Purified proteins are added to the in vitro antifungal microplate assay as described in Spelbrink et al. 2004. Unless otherwise noted, all transformation, growth, induction, purification, and antifungal assay steps were as described in Spelbrink et al. 2004 and Example 2.

The MtDef4 cysteine variants all inhibit growth of *Neurospora crassa*. However, inhibition of *Neurospora* by the MtDef4 cysteine variants is greatly diminished compared to MtDef4.1 (H33R) as complete inhibition of *Neurospora* growth is not observed at concentrations as high as 20 M. Two MtDef4 variants (MtDef4.1H33R, C3S, C47S) and MtDef4.1 (H33R, C24S, C43S) do inhibit growth of *Fusarium graminearum*, with complete inhibition at a concentration of 6 μM. The MtDef4-25 and MtDef4-36 variants are less active than the other MtDef4 cysteine variants against *F. graminearum*, but do provide complete inhibition of *F. graminearum* at concentrations above 30 μM.

Example 11

Dicot Plant Expression Vectors

To express the MtDef4.1 (H33) protein in dicot plants, three *Agrobacterium*-mediated plant transformation vectors can be constructed. All vectors, shown here in FIGS. 8, 9, and 10, contain *Agrobacterium* right and left border sequences and a selectable marker gene comprising a NOS promoter and NOS terminator that is operably linked to a BAR gene encoding a phosphinothricin acetyltransferase that confers resistance to the herbicide glufosinate. The vectors also use an MtDef4.1 genomic clone (SEQ ID NO:108) that encodes the MtDef4.1 protein (SEQ ID NO:112). The first vector would contain an MtDef4.1 expression cassette comprising an FMV promoter, a "Super Ubiquitin" intron, a genomic sequence encoding the MtDef4 exon 1, the MtDef4 intron, and the MtDef4 exon 2, and a NOS polyadenylation sequence, wherein all expression elements are operably linked as shown in SEQ ID NO:75. The second vector would contain an MtDef4 expression cassette comprising an FMV promoter, a "Super Ubiquitin" intron, a genomic sequence encoding the MtDef4 exon 1, the MtDef4 intron, and the MtDef4 exon 2 with an in-frame C-terminal fusion to a vacuolar targeting sequence, and a NOS polyadenylation sequence, wherein all expression elements are operably linked as shown in SEQ ID NO:76. The particular vacuolar targeting sequence used in this vector is the C-terminal CTPP vacuolar targeting signal from the barley lectin gene. The third vector would contain an MtDef4 expression cassette comprising an FMV promoter, a

TABLE 10

MtDef4 Cysteine Variants and Biological Activity

| | Antifungal Activity | |
|---|---|---|
| Table 10 MtDef4.1 (H33R) Cys/Ser Mutants | Fusarium graminearum | Neurospora crassa |
| MtDef4.1 (H33R, C3S, C47S)<br>RTSESQSHKFKGPCASDHNCASVCQTERFSGGRCRGFRRRCFCTTHS<br>SEQ ID NO: 135 | ++++ | + |
| MtDef4.1 (H33R, C14S, C34S)<br>RTCESQSHKFKGPSASDHNCASVCQTERFSGGRSRGFRRRCFCTTHC<br>SEQ ID NO: 136 | +++ | + |
| MtDef4.1 (H33R, C20S, C41S)<br>RTCESQSHKFKGPCASDHNSASVCQTERFSGGRCRGFRRRSFCTTHC<br>SEQ ID NO: 137 | +++ | + |
| MtDef4.1 (H33R, C24S, C43S)<br>RTCESQSHKFKGPCASDHNCASVSQTERFSGGRCRGFRRRCFSTTHC<br>SEQ ID NO: 138 | ++++ | + |
| MtDef4.1 (H33R)<br>SEQ ID NO: 125 | +++++ | ++++ |

"Super Ubiquitin" intron, a genomic sequence encoding the MtDef4 exon 1, the MtDef4 intron, and the MtDef4 exon 2 with an in-frame ER retention signal sequence, and a NOS polyadenylation sequence, wherein all expression elements are operably linked as shown in SEQ ID NO:150.

This dicot vector can be introduced into a suitable *Agrobacterium* strain and used to transform dicot plants such as alfalfa, *Arabidopsis*, barrel medic, banana, broccoli, bean, cabbage, canola, carrot, cassava, cauliflower, celery, citrus, cotton, a cucurbit, eucalyptus, garlic, grape, onion, lettuce, pea, peanut, pepper, potato, poplar, pine, sunflower, safflower, soybean, strawberry, sugar beet, sweet potato, tobacco, and tomato. Glufosinate resistant dicot plants can then be selected and assayed for expression of the MtDef4 transgene. Dicot plants expressing the MtDef4 transgene are then assayed for resistance to fungal pathogens. When the dicot plant is a potato plant containing any of the MtDef4 dicot expression vectors described in this example, transgenic potato plants will be obtained and assayed for resistance to *Verticillium* Wilt by employing the procedures essentially as described in U.S. Pat. No. 6,916,970.

Example 12

Control of Fungal Infection in Transgenic *Arabidopsis*

It is well-documented that *A. thaliana* is susceptible to *F. graminearum* (Chen et al. Molecular Plant Pathology 7: 391-403, 2006; Skadsen and Hohn, Physiol. Mol. Plant. Pathol. 64: 45-53, 2004; Urban et al. Plant J 32: 961-973, 2002). To test the antifungal defensins MsDef1 and MtDef4 for their ability to confer resistance to *F. graminearum*, a foliar *Fusarium-Arabidopsis* pathosystem was used (Chen et al., Ibid; Makandar et al. Mol Plant Microbe Interact 19: 123-129, 2006; Skadsen and Hohn, Ibid).

Figure 11:
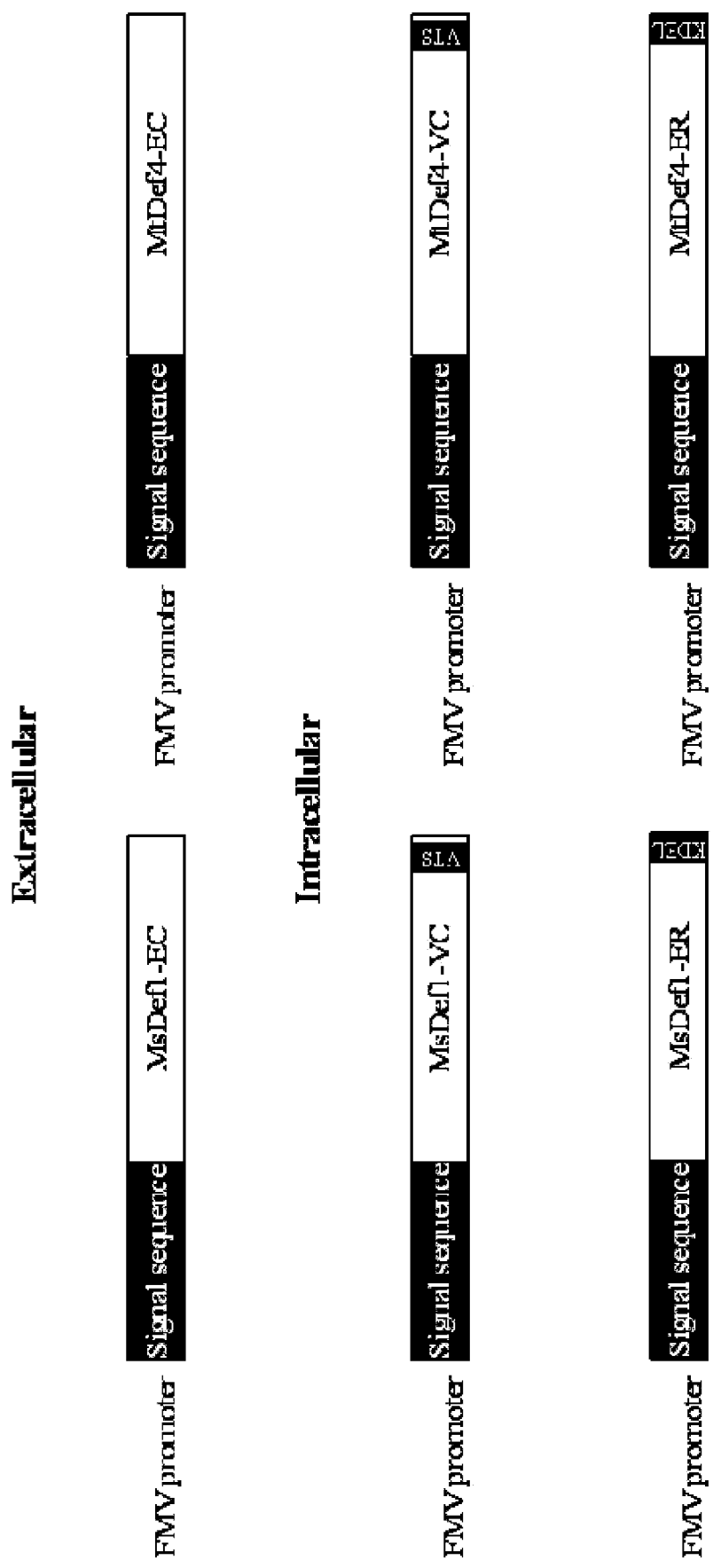

In wheat, *F. graminearum* displays a biotrophic phase during the first 48 to 72 hr of infection and then switches to a necrotrophic phase at approximately 72 hr after inoculation (Bushnell et al. Histology and physiology of *Fusarium* head blight. In *Fusarium* Head Blight of Wheat and Barley. Leonard, K. J. and Bushnell, W. R. (eds.) St Paul, Minn.: American Phytopathological Society Press, pp. 44-83, 2003). In *Arabidopsis*, this pathogen colonizes the wound-inoculated leaf tissue by both inter- and intracellular growth and extensive cell death is observed ahead of the advancing hyphae (Chen et al., Ibid). Without being limited by theory, it is believed that antifungal defensins when co-expressed both extra- and intracellularly, will confer much higher level of resistance to FHB in transgenic "Bobwhite" wheat and *A. thaliana* than defensins expressed only extracellularly. In order to test this hypothesis, chimeric defensin gene constructs were generated that result in over-expression of MsDef1 or MtDef4 either extracellularly or intracellularly (i.e., vacuole or endoplasmic reticulum) in transgenic *A. thaliana* ecotype Columbia. The MtDef4 vectors use an MtDef4.1 genomic clone (SEQ ID NO:108) that encodes the MtDef4.1 protein (SEQ ID NO:112). For vacuolar targeting, a translational fusion of each defensin to the C-terminal barley lectin vacuolar sorting signal was made. For endoplasmic reticulum (ER) targeting, a C-terminal translational fusion of each defensin to the KDEL sequence was made. Thus, six constructs for extracellular (EC), vacuolar (VC) and ER targeting of MsDef1 and MtDef4 (FIG. 11) were made and were compared for their ability to confer resistance to *F. graminearum*. For each construct, several independent transgenic events were generated. Transgenic events containing a single copy of the chimeric gene cassette were analyzed for expression of each defensin by sandwich ELISA. Expression of the protein was heritable through each generation tested. The 4-week old progeny (T3 generation) of two independent events expressing the protein were tested for resistance to *F. graminearum* as described (Makandar et al., Ibid). Four leaves of each plant (10 plants/event) were infiltrated with 100 μl of *F. graminearum* PH-1 conidia ($5 \times 10^5$/ml) using a syringe tip. Disease severity was assessed at 2, 5 and 7 days post-inoculation by visual scoring of symptoms (0=no symptoms, 1=chlorotic lesions covering less than 25% of the leaf area, 2=water-soaked lesions covering 25-50% of the leaf area, 3=chlorotic lesions covering 50-75% of the leaf area and extensive mycelial growth, 4=severe decay and detachment of leaves) and by calculating the disease severity (DS) index (Chen et al., Ibid).

Figure 8:
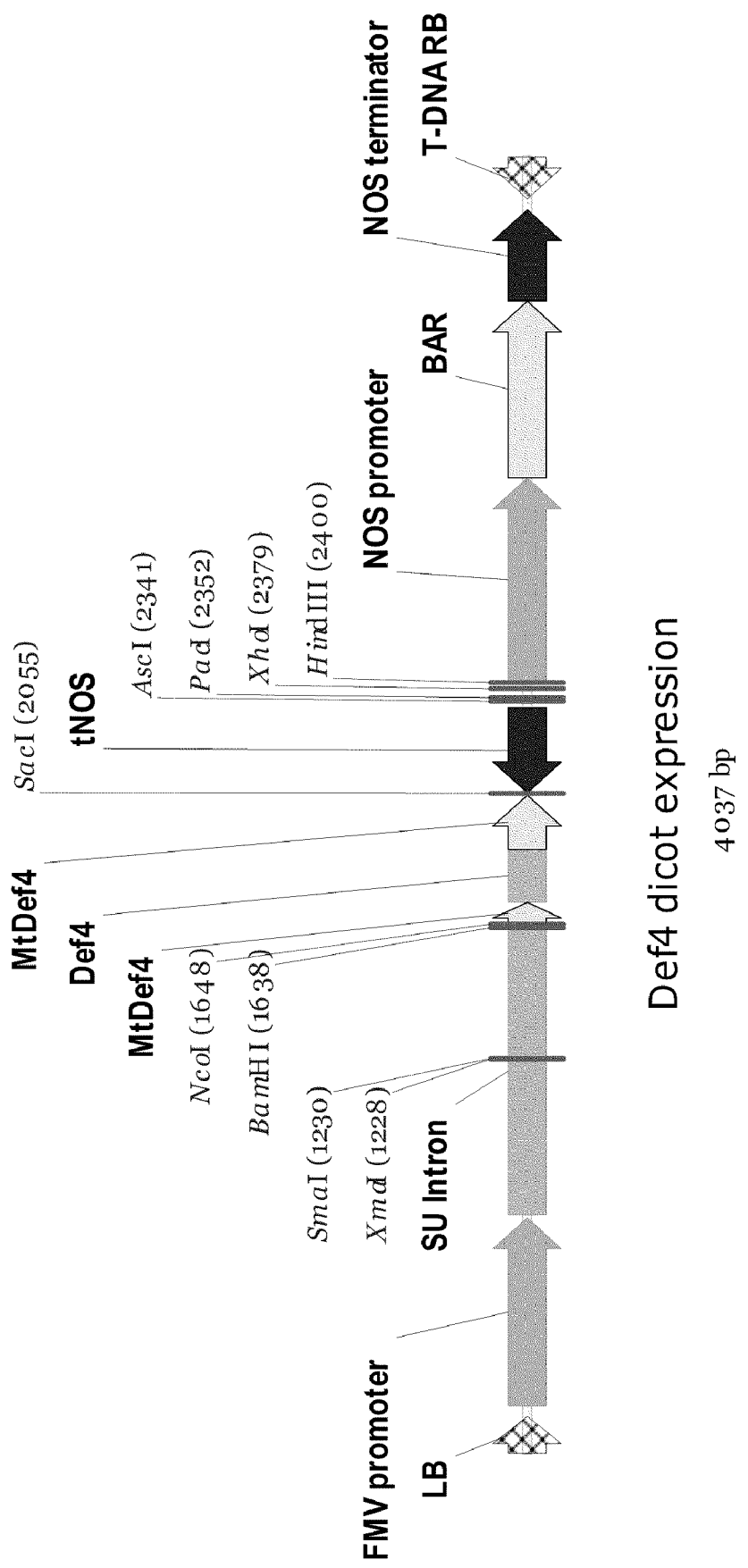
Figure 12:
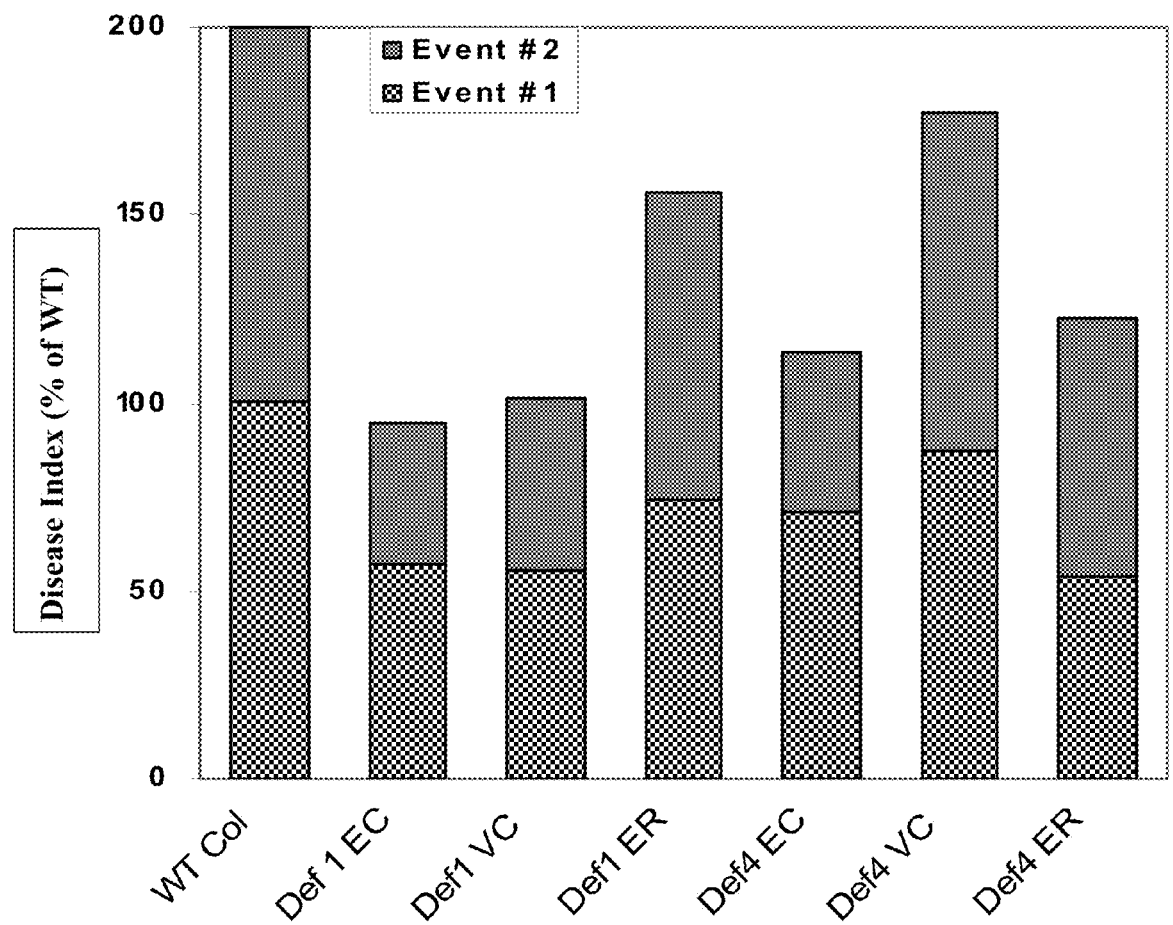

Constitutive over-expression of MsDef1 or MtDef4 can confer strong resistance to *F. graminearum* in transgenic *Arabidopsis* plants as shown in FIG. 12. Certain transgenic plants show as much as a 59-68% reduction in disease severity (DS) index as compared to that of the wild type plants (100%) at 7 days post-inoculation. However, significant differences were noted among different constructs. The MsDef1-EC and MsDef1-VC constructs were more effective than the MsDef1-ER construct in providing resistance to this pathogen. The MsDef1-ER plants showed 65% disease severity index and were more susceptible than either MsDef1-EC or MsDef1-VC plants to this pathogen. Similarly, the MtDef4-EC construct provides strong resistance to the pathogen (only 41% DS), but the MtDef4-VC construct does not (70% DS). In contrast to the ER-targeted MsDef1 (65% DS), ER-targeted MtDef4 provides significantly more protection from the disease (51% DS) (FIG. 8). Similar results were obtained at 5 days post-inoculation (Table 11).

Table 11. Disease severity index of the wild-type and transgenic *A. thaliana* lines expressing various constructs.

TABLE 11

| | *F. graminearum* disease index[a] | | |
|---|---|---|---|
| Construct | 2 dpi | 5 dpi | 7 dpi |
| WT-Col | 100 | 100 | 100 |
| MsDef1-EC | 36 | 32 | 47 |
| MsDef1-VC | 30 | 41 | 51 |
| MsDef1-ER | 63 | 65 | 78 |
| MtDef4-EC | 38 | 41 | 57 |
| MtDef4-VC | 67 | 70 | 88 |
| MtDef4-ER | 67 | 51 | 61 |

[a]Disease index is expressed as percent wild type disease. Data for a representative event for each construct is shown.

Figure 13:
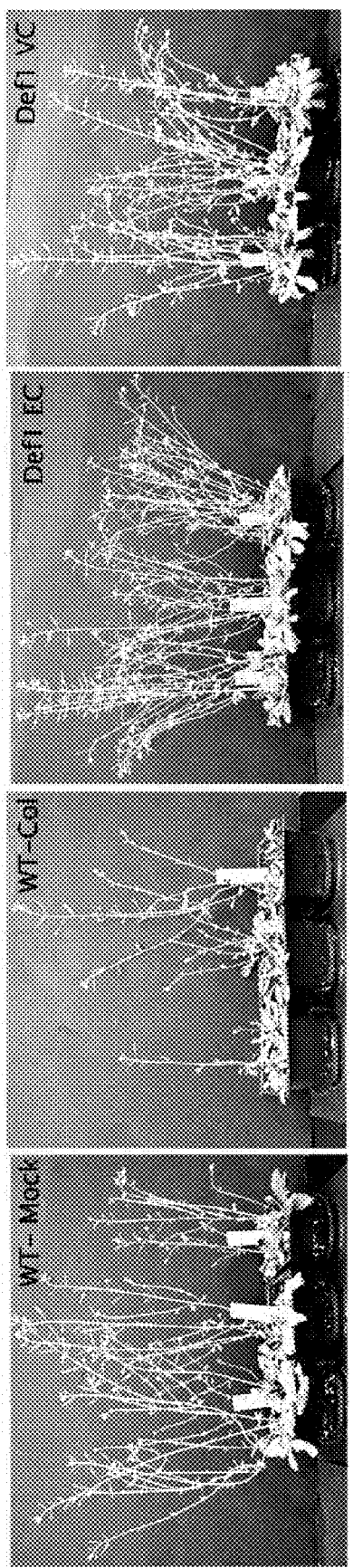

Four weeks post inoculation, 90% of the transgenic plants expressing the MsDef1-EC, MsDef1-VC and MtDef4-EC constructs bolted normally and produced numerous flowers and set viable seeds like the mock-inoculated wild-type plants, in comparison to the pathogen-inoculated wild-type plants, where only 10% bolted normally and set viable seed and the remaining plants showed much delayed bolting and produced very few flowers (FIG. 13, MsDef1 plants shown).

The strong resistance to *F. graminearum* observed in the MsDef1-EC and MsDef1-VC plants was further confirmed by trypan blue staining of fungal hyphae in the infected leaves 2, 5 and 7 days post-inoculation. The growth of the pathogen was markedly reduced in the inoculated leaves of these transgenic lines as compared with that in the wild-type plants.

Example 13

Control of Fungal Infection in Transgenic Wheat

A chimeric MtDef4 gene expression cassette consisting of the maize ubiquitin promoter and intron, the tobacco etch virus (TEV) leader, the monocot-codon-optimized MtDef4.1 (H33R) coding sequence, and the CaMV 35S terminator was made and cloned between the T-DNA borders into the binary vector pZP212 (Hajdukiewicz et al., 1994) as described in Example 6. This vector was used to transform the spring wheat cultivar Bobwhite (BW) and the Chinese wheat cultivar Xin Chun 9 (XC9). Six independent transgenic Bobwhite events and one transgenic XC9 event were generated. Based on the segregation analysis of the seven events, three Bobwhite events and the one XC9 event contained a single copy of the MtDef4 gene. Homozygous plants from all four single-copy events were identified in the T2 generation (Table 12). Homozygous plants from all four events expressed the MtDef4 protein as determined by sandwich ELISA.

Table 12. Total number of wheat transgenic lines produced and the isolated homozygous lines

TABLE 12

| Cultivar | Line | Status[a] | No. of families tested | Homozygous lines isolated[b] |
|---|---|---|---|---|
| BW | 431-1-3-1 (A) | Single | 4 | 1 (#11) |
| BW | 431-5-1-1 (B) | Single | 6 | 1 (#4) |
| BW | 431-5-2-1 (C) | Multiple | 3 | none |
| BW | 445-2-1-1 (D) | Multiple | 3 | none |
| BW | 445-2-2-1 (E) | Multiple | 4 | none |
| BW | 446-1-1-1 (F) | Single | 5 | 3 (#2, #3, #10) |
| XC9 | 426-1-1-1 | Single | 5 | 3 (#103, #104, 426) |

[a]Based on the segregation ratios
[b]Isolated in T2 generation

Two homozygous lines (T3 generation) were tested for resistance to FHB in the greenhouse. Thirty-one and 29 heads of transgenic lines BW.A#11 and XC9.426#103, respectively, were inoculated using a single-floret inoculation method. The FHB-resistant cultivar Alsen and the FHB-susceptible cultivar Norm along with non-transformed BW and XC9 were included as controls in this assay. The inoculated heads were visually scored for FHB symptoms 4, 9, 11, 14 and 21 days after inoculation (DAI) and the severity of symptoms was expressed as percent head blight severity as per Stack and Mullen (1998). Most of the spikes dried out 21 DAI and hence the 21 DAI data were not included in the analyses. The percent FHB severity for the MtDef4 transgenics and controls are shown in Table 13.

Table 13. Percent FHB severity in greenhouse evaluations of two transgenic wheat lines and FHB checks on 14 DAI.

TABLE 13

| Line/Cv. | No. of heads tested | % FHB severity[a] |
|---|---|---|
| BW.A#11 | 31 | 11* |
| Bobwhite | 12 | 23 |
| XC9.426#103 | 20 | 31 |

TABLE 13-continued

| Line/Cv. | No. of heads tested | % FHB severity[a] |
|---|---|---|
| Xin Chun 9 | 16 | 34 |
| Alsen | 24 | 12 |
| Norm | 7 | 31 |

% FHB severity is average of all the heads.
*Significantly different at P = 0.05 compared to Bobwhite and Norm.

Figure 14:
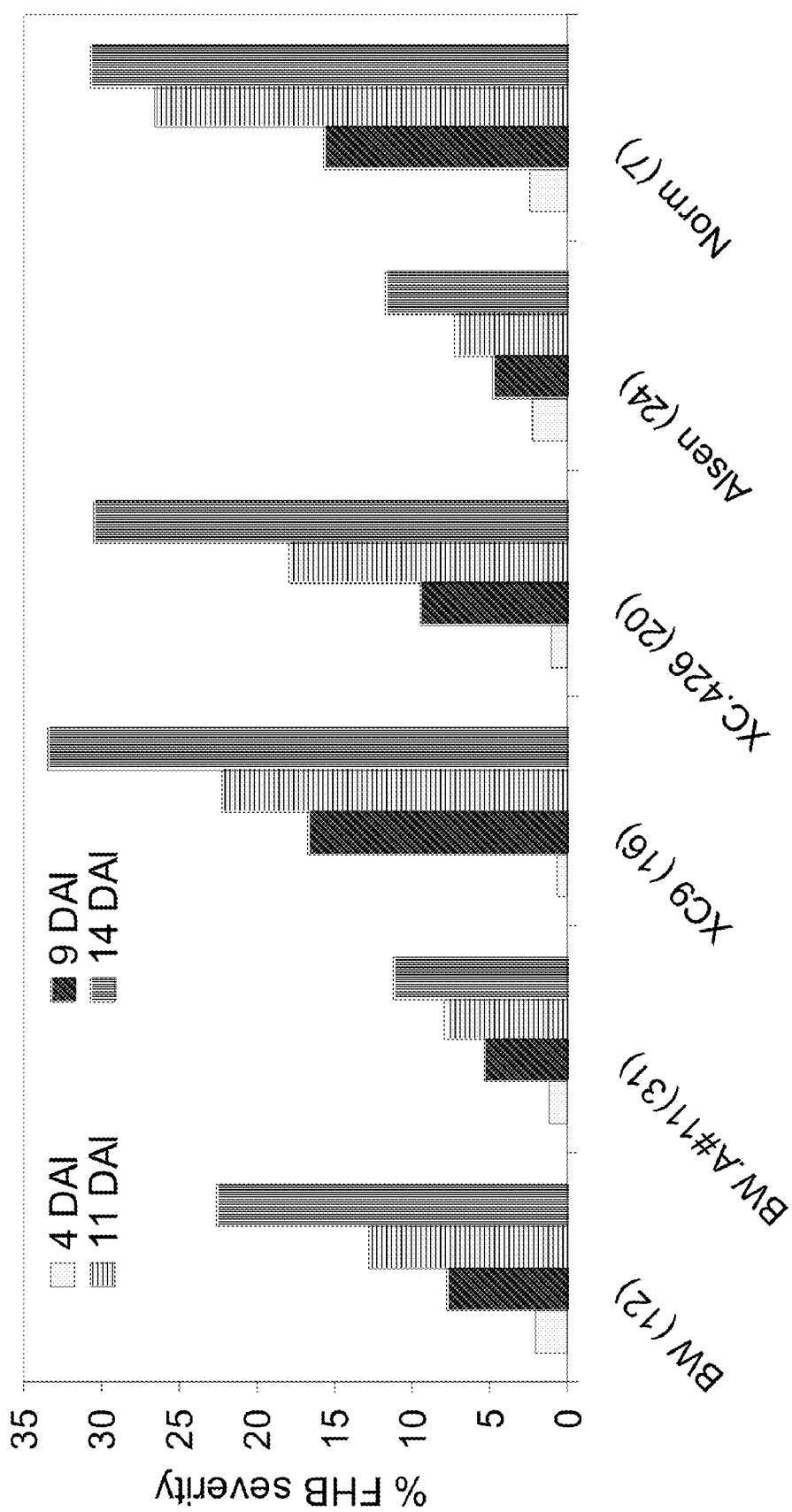
Figure 15:
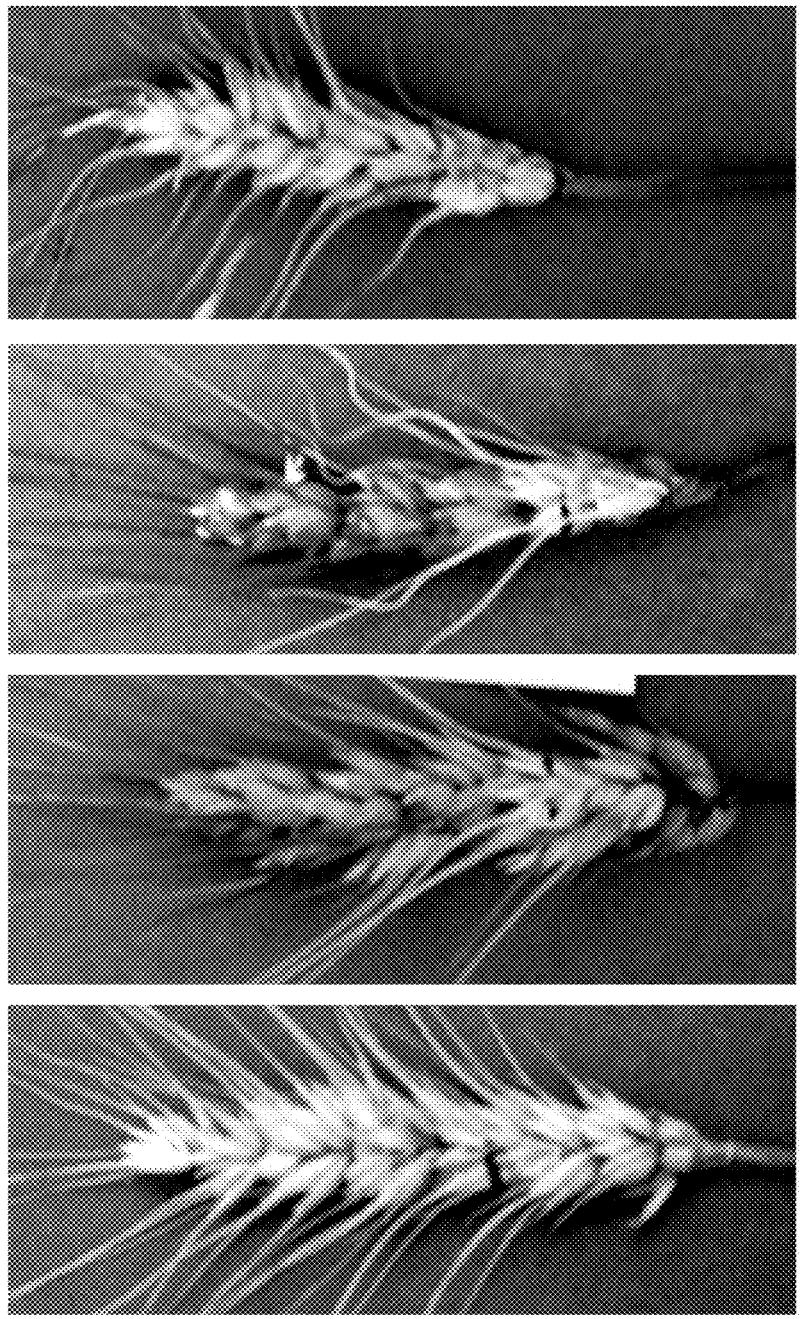

The transgenic line BW.A#11 showed 11% FHB severity, similar to that of the FHB-resistant cultivar Alsen, whereas non-transformed Bobwhite showed 23% FHB severity at 14 DAI. This decrease in FHB severity is significant at P=0.05. On the other hand, the transgenic XC9.426#103 homozygous line did not show any significant resistance when compared to non-transformed FHB-susceptible XC9 cultivar (Table 13). The progression of the FHB severity of transgenic lines and controls is shown in FIG. 14. FIG. 15 shows FHB severity at 14 DAI in representative heads of the transgenic and control lines. These data indicate that the constitutive over-expression of MtDef4 confers resistance to FHB in transgenic Bobwhite wheat.

Figure 16:
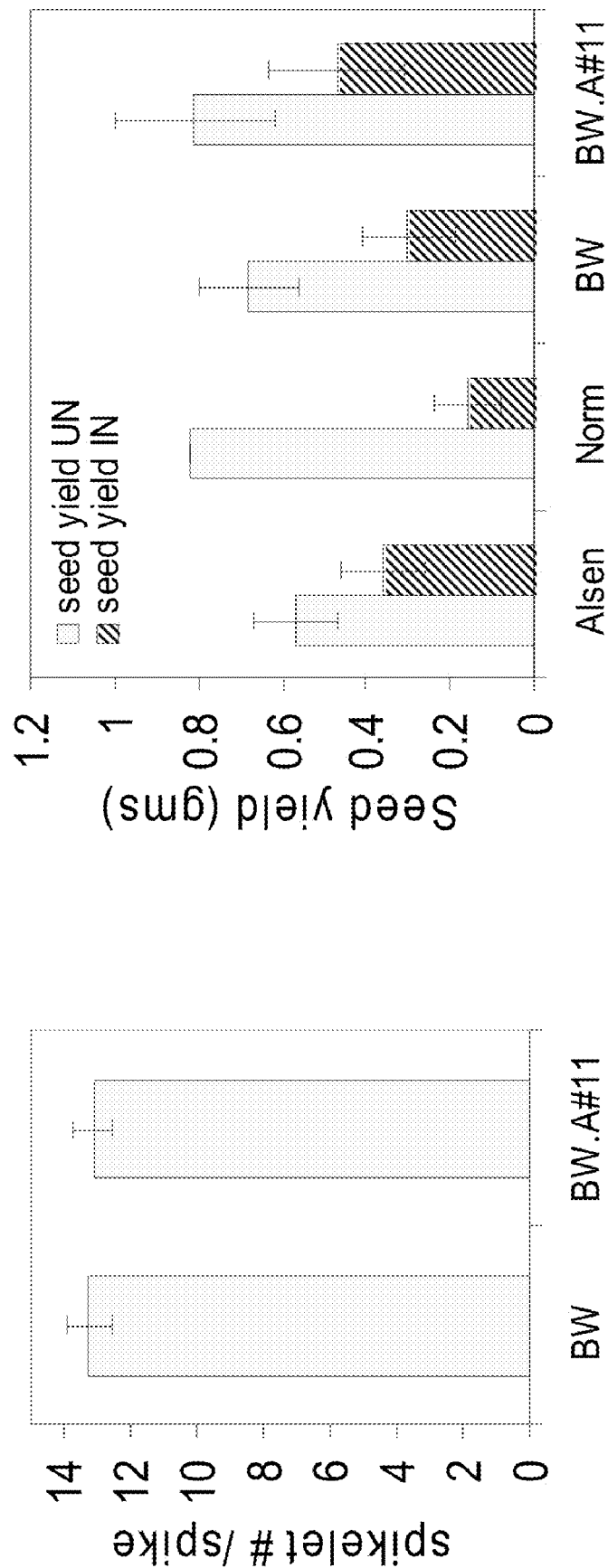
FIG. 16 shows a comparison of yield parameters between nontransgenic and transgenic Bobwhite wheat (BW) along with FHB (Fusarium Head Blight) checks. The left panel shows spikelet number/spike for nontransgenic BW and transgenic BW.A#11. The right panel shows seed yield from uninoculated (UN) and inoculated (IN) in Alsen, Norm, nontransgenic BW and transgenic BW.A#11.

The spikelet number per spike and seed yield are two agronomically important yield parameters (Makandar et al., Mol Plant Microbe Interact 19: 123-129, 2006). The spikelet number per spike was measured as the average number of spikelets per spike from 12 BW and 31 BW.A#11 plants. The spikelet number per spike of transgenic BW.A#11 plants was comparable to that of nontransgenic BW (FIG. 16, Left.). Seed yield from uninoculated (UN) and inoculated (IN) spikes was calculated as average seed yield (g/spike) from variable numbers of individuals per line (FIG. 16, Right.). There was a significant difference in seed yield between UN and IN spikes of Alsen, Norm and non-transgenic BW based on non-paired Student's t at P=0.05. There was no significant difference between UN and IN transgenic BW.A#11 at P=0.001. These results indicate that MtDef4 expression does not have any adverse effects on the yield parameters of transgenic plants.

Example 14

Production of MtDef4 Transgenic Maize

Transgenic maize plants containing extracellularly-targeted MtDef4.1 (H33R) were produced by transformation of the monocot optimized MtDef4.1 (H33R) construct (SEQ ID: 72; FIG. 6) in the pZP212 vector. Maize inbred H99 was transformed using the method in Sidorov et al 2006 as described in Example 8.

The PCR screening results for the MtDef4 T0 plants were as follows:

TABLE 14

Summary of Maize Transformation Experiment with

| Maize Inbred | Lines Produced | Lines Successfully Transplanted | Lines PCR+ for MtDef4.1(H33R) | Percent Positive |
|---|---|---|---|---|
| H99[1] | 39 | 34 | 17 | 50% |

[1]Selected with paromomycin.

Selected transgenic maize lines have proceeded to the T1 screening stage. The 20 T1 plants of each line have been subjected to both PCR and ELISA screens, with results as follows:

TABLE 15

Evaluation of Transgenic Maize Transformed with an MtDef4 Polypeptide Expression Vector

| Maize Inbred | Lines Evaluated | Lines PCR+ for MtDef4 | Lines with Single Inserts[1] | Detection of MtDef4.1 (H33R) Protein[2] | Percent Selected |
|---|---|---|---|---|---|
| H99[2] | 14 | 8 | 8 | 6 | 42.9% |

[1]Single insertion determined by $X^2$ analyses of segregation data.
[2]MtDef4 protein detected by sandwich ELISA Selected T1 lines with stable simple insertions have been crossed to the widely-used public inbred B73 for subsequent testing.

Example 15

Further Characterization of MtDef4 Cysteine Variants

The MtDef4.1 (H33R) protein and cysteine bridge variants of Def4 were expressed in *Pichia pastoris* as per the description in Example 10. Expressed polypeptides were recovered from the *Pichia* culture media following induction. The masses of the various expressed MtDef4 polypeptides were experimentally determined using nano-ESI Quadrupole Time-of-Flight on a QSTAR XL instrument (Applied Biosystems, Foster City, Calif.) in positive electrospray mode. In the initial expression experiments, the expressed variant protein for SEQ ID NOS: 136, 137, and 138 had an observed or experimentally determined molecular weight that was lower than the expected or predicted value that is calculated for the intact variant MtDef4 polypeptides following secretion and removal of the yeast alpha-mating factor signal peptide and propeptide (see Table 16). The biological activity of the control and variant proteins was also determined by determining the $IC_{50}$ value against *Fusarium graminearum*. The full length MtDef4.1 (H33R, C3S, C47S) (SEQ ID NO:135) had an $IC_{50}$ value that was only about 1.5-fold higher than the wild-type control MtDef4.1 (H33R) (SEQ ID NO: SEQ ID NO:125) protein. The truncated MtDef4.1 (H33R, C24S, C43S) (SEQ ID NO:138) protein variant had an $IC_{50}$ value that was only about 1.8-fold higher than the wild-type control MtDef4.1 (H33R) (SEQ ID NO: SEQ ID NO:125) protein. Biological activity of the SEQ ID NO:136 and 137 cysteine variants was reduced relative to the MtDef4.1 (H33R) control protein but not completely eliminated.

TABLE 16

Summary of MtDef4.1(H33R) cysteine variant data

| | $IC_{50}$ | Expected MW[1] | Observed MW |
|---|---|---|---|
| MtDef4.1(H33R) SEQ ID NO: 125 | 3.66 | 5335.01 | 5334.664 |
| MtDef4.1(H33R, C3S, C47S) SEQ ID NO: 135 | 5.58 | 5304.89 | 5305.086 |
| MtDef4.1(H33R, C14S, C34S) SEQ ID NO: 136 | 24.16 | 5304.89 | 4554.916 |
| MtDef4.1(H33R, C20S, C41S) SEQ ID NO: 137 | 21.64 | 5304.89 | 4058.346 |
| MtDef4.1(H33R, C24S, C43S) SEQ ID NO: 138 | 6.65 | 5304.89 | 4058.593 |

[1]Expected Molecular Weight is calculated from complete sequence of the indicated peptide.

Taken together, these data demonstrate that certain cysteine bridges (i.e. disulfide bonds) in MtDef4 polypeptides can be disrupted to obtain a variant MtDef4 polypeptide that retains antifungal activity. MtDef4 polypeptides that lack certain disulfide bonds can be used in applications where an antifungal protein which is more readily digested by humans or animals is desired. The data also indicate that truncated MtDef4 polypeptides retain antifungal activity.

Example 16

Truncated MtDef4 Polypeptides with Antifungal Activity

Computer analysis of both the truncated MtDef4.1 cysteine variant sequence data and the corresponding observed molecular weights from Table 16 (above) was used to predict potential MtDef4 truncations with antifungal activity. More specifically, the MtDef4.1 (H33R, C20S, C41S) variant (SEQ ID NO:137) is predicted to give rise to one or more truncated variant(s) that either: a) lack(s) the last ten (10) C-terminal residues of the mature MtDef4 polypeptide (SEQ ID NO:152); b) lack(s) both the first 6 N-terminal residues as well as the last 5 C-terminal residues of the mature mtDef4 polypeptide (SEQ ID NO:153), and/or lack(s) both the first N-terminal residue as well as the last 9 C-terminal residues of the mature mtDef4 polypeptide (SEQ ID NO:154). The MtDef4.1 (H33R, C24S, C43S) variant (SEQ ID NO:138) is predicted to give rise to a truncated variant that lacks the last ten (10) C-terminal residues of the mature MtDef4 polypeptide (SEQ ID NO:155) and/or a truncated variant that lacks both the first N-terminal residue as well as the last 9 C-terminal residues of the mature mtDef4 polypeptide (SEQ ID NO:156). Each of these sequences is provided in Table 17. Nucleotide sequences encoding the MtDef4 polypeptides that contain cysteine to serine changes can be designed with G+C contents appropriate for plant expression, engineered into plant expression vectors, and introduced in transgenic plants to produce truncated forms of the MtDef4 protein for controlling fungal infections of those plants.

TABLE 17

Comparison of an MtDef4 polypeptide with Truncated MtDef4 peptides with antifungal activity

| SEQ ID NO: | Amino Acid Sequence | Type |
|---|---|---|
| 137 | RTCESQSHKFKGPCASDHNSASVCQTERFSGGRCRGFRRRSFCTTHC | Mature MtDef4 polypeptide |
| 152 | RTCESQSHKFKGPCASDHNSASVCQTERFSGGRCRGF | Truncated MtDef4 polypeptide |
| 153 | SHKFKGPCASDHNSASVCQTERFSGGRCRGFRRRSF | Truncated MtDef4 polypeptide |
| 154 | TCESQSHKFKGPCASDHNSASVCQTERFSGGRCRGFR | Truncated MtDef4 polypeptide |
| 138 | RTCESQSHKFKGPCASDHNCASVSQTERFSGGRCRGFRRRCFSTTHC | Mature MtDef4 polypeptide |
| 155 | RTCESQSHKFKGPCASDHNCASVSQTERFSGGRCRGF | Truncated MtDef4 polypeptide |
| 156 | TCESQSHKFKGPCASDHNCASVSQTERFSGGRCRGFR | Truncated MtDef4 polypeptide |

The use of truncated MtDef4 variant polypeptides to control fungal infections is thus contemplated. As used herein, the phrase "truncated MtDef4 polypeptide" refers to a fragment of the mature MtDef4 protein with antifungal activity wherein one or more amino acids are deleted from the N-terminal end, C-terminal end, the middle of the protein, or combinations thereof. The truncated MtDef4 polypeptides that are useful for fungal control can comprise the polypeptides of SEQ ID NO; 152, 153, 154, 155, or 156 and variants thereof that comprise conservative amino acid substitutions of these sequences. The truncated MtDef4 polypeptides that are useful for fungal control can also comprise deletions of any number of N-terminal residues from 1 to 6 of a mature MtDef4 polypeptide and/or deletions of any number of C terminal residues from 38 to 47 of a mature MtDef4 polypeptide. MtDef4 polypeptides that can be truncated at the N- and/or C-terminus to yield antifungal proteins include, but are not limited to, a MtDef4 consensus sequence (SEQ ID NO: 71), amino acids 30-76 of AL386553 (SEQ ID NO:105), a MtDef4.1 sequence (SEQ ID NO:112), a MtDef4.2 (SEQ ID NO:114) sequence, a MtDef4.3 (SEQ ID NO:116) sequence, a MtDef4.1 (H33R) sequence (SEQ ID NO:125), a MtDef4.1 (H33R, C3S, C47S) sequence (SEQ ID NO:135), a MtDef4.1 (H33R, C14S, C34S) sequence (SEQ ID NO:136), a MtDef4.1 (H33R, C20S, C41S) sequence (SEQ ID NO:137), and a MtDef4.1 (H33R, C24S, C43S) sequence (SEQ ID NO:138).

Other useful embodiments include an isolated DNA construct comprising a heterologous promoter, a sequence that encodes a truncated MtDef4 polypeptide with at least 85% sequence identity to amino acid residues 7 to 37 of SEQ ID NO:112, and a polyadenylation sequence, wherein said promoter, said sequence encoding a truncated MtDef4 polypeptide and said polyadenylation sequence are operably linked. Alternatively, a sequence that encodes a truncated MtDef4 polypeptide with at least 90% or 95% sequence identity to amino acid residues 7 to 37 of SEQ ID NO:112 can be used. The sequence that encodes a truncated MtDef4 polypeptide can also be selected from sequences that encode the truncated MtDef4 polypeptides of SEQ ID NOs:152-156. The sequence that encodes a truncated MtDef4 polypeptides can also comprise a sequence that encodes a truncated MtDef4 polypeptide with deletions of any number of N-terminal residues from 1 to 6 of a mature MtDef4 polypeptide and/or deletions of any number of C terminal residues from 38 to 47 of a mature MtDef4 polypeptide. The DNA constructs that encode truncated MtDef4 polypeptides can further comprise sequences encoding signal peptides and/or other intracellular targeting signals that are operably linked to the sequence encoding the truncated MtDef4 polypeptide.

Still other useful embodiments of the invention include isolated nucleic acids that encode a truncated MtDef4 polypeptide and truncated MtDef4 polypeptides that have been isolated.

Various patent and non-patent publications are cited herein, the disclosures of each of which are incorporated herein by reference in their entireties.

NON-PATENT PUBLICATIONS

Bent A F, Kunkel B N, Dahlbeck D, Brown K L, Schmidt R, Giraudat J, Leung J, Staskawicz B J. (1994) RPS2 of *Arabidopsis thaliana*: a leucine-rich repeat class of plant disease resistance genes. Science 265(5180):1856-60.

Broekaert, W. F., Terras, F. R., Cammue, B. P., and Vanderleyden, J. (1990). An automated quantitative assay for fungal growth inhibition. FEMS Microbiology Letters 69, 55-60.

Broekaert, W. F., Terras, F. R., Cammue, B. P., and Osborn, R. W. (1995). Plant defensins: novel antimicrobial peptides as components of the host defense system. Plant Physiol 108, 1353-1358.

Broekaert, W. F., Cammue, B. P. A., De Bolle, M. F. C., Thevissen, K., De Samblanx, G. W., and Osborn, R. W. (1997). Antimicrobial peptides from plants. Critical Reviews in Plant Sciences 16, 297-323.

Broothaerts W, Mitchell H J, Weir B, Kaines S, Smith L M, Yang W, Mayer J E, Roa-Rodriguez C, Jefferson R A. 2005. Gene transfer to plants by diverse species of bacteria. 2005. Nature. 433(7026):629-33.

Bustin, S. A. Quantification of mRNA using real-time reverse transcription PCR (RT-PCR): trends and problems. Journal of Molecular Endocrinology (2002) 29, 23-39.

Callis, J, Fromm, M, Walbot, V. (1987) Introns increase gene expression in cultured maize cells. Genes Dev. 1987 December; 1(10):1183-200.

Cappelini, R. A., and Peterson, J. L. (1965). Macroconidium formation in submerged cultures by a non-sporulating strain of *Gibberella zeae*. Mycologia 57, 962-966.

Cazzonnelli, C. I. and J. Velten. (2003) Construction and Testing of an Intron-Containing Luciferase Reporter Gene From *Renilla reniformis*. Plant Molecular Biology Reporter 21: 271-280.

Collier, R., B. Fuchs, N. Walter, W. K. Lutke, and C. G. Taylor. (2005) Ex vitro composite plants: an inexpensive, rapid method for root biology. Plant J 43: 449-457.

Correll, J. C., Klittich, C. J. R., and Leslie, J. F. (1987). Nitrate nonutilizing mutants of *Fusarium graminearum* and their use in vegetative compatibility tests. Phytopathology 77, 1640-1646.

da Silva Conceicao, A., and Broekaert, W. F. (1999). Plant Defensins. In Pathogenesis-related proteins in plants, S. Muthukrishnan, ed (New York: CRC Press), pp. 247-260.

Doyle J J, Schuler M A, Godette W D, Zenger V, Beachy R N, Slightom J L. (1986) The glycosylated seed storage proteins of *Glycine max* and *Phaseolus* vulgarism Structural homologies of genes and proteins. J Biol. Chem. 261(20): 9228-38.

Frame, B. R., Shou, H., Chikwamba, R. K., Zhang, Z., Xiang C., Fonger, T. M., Pegg S E, Li B, Nettleton D S, Pei D, and Wang K. (2002) *Agrobacterium tumefaciens*-mediated transformation of maize embryos using a standard binary vector system. Plant Physiol. 129(1):13-22.

Gao, A., Hakimi, S. M., Mittanck, C. A., Wu, Y., Woerner, M. B., Stark, D. M., Shah, D. M., Liang, J., and Rommens, C. M. T. (2000). Fungal pathogen protection in potato by expression of a plant defensin peptide. Nature Biotechnology 18, 1307-1310.

Grant M R, Godiard L, Straube E, Ashfield T, Lewald J, Sattler A, Innes R W, Dangl, J L. (1995) Structure of the *Arabidopsis* RPM1 gene enabling dual specificity disease Resistance Science. 269(5225):843-6.

Hammond-Kosack, K. E., Urban, M., Baldwin, T., Daudi, A., Rudd, J. J., Keon, J., Lucas, J. A., Maguire, K., Kornyukhin, D., Jing, H.-C., Bass, C., and Antoniw, J. (2004). 4th International Crop Science Congress. In New directions for a diverse planet, T. Fischer, Turner, N., Angus, J., McIntyre, L., Robertson, M., Borrell, A., Lloyd, D., ed (Brisbane, Australia: The Regional Institute, Ltd, Gosford, Austraila).

Hanks, J. N., Snyder, A. K., Graham, M. A., Shah, R. K., Blaylock, L. A., Harrison, M. J., and Shah, D. M. (2005). Defensin gene family in *Medicago truncatula*: structure, expression and induction by signal molecules. Plant Mol Biol 58, 385-399.

Horsch, R. B., J. E. Fry, N. Hoffman et al. (1985) A simple and general method for transferring genes into plants. Science. 227: 1229-1231

Kingsman S M, Kingsman A J, Dobson M J, Mellor J, Roberts N A. (1985) Heterologous gene expression in *Saccharomyces cerevisiae*. Biotechnol Genet Eng Rev. 3:377-416.

Koehler S M, and Ho, T H. (1990) Hormonal regulation, processing, and secretion of cysteine proteinases in barley aleurone layers. Plant Cell. (8):769-83.

Lam E, and Chua N H. (1991) Tetramer of a 21-base pair synthetic element confers seed expression and transcriptional enhancement in response to water stress and abscisic acid. J Biol Chem. 1991 Sep. 15; 266(26):17131-5.

Lay, F. T., and Anderson, M. A. (2005). Defensins—components of the innate immune system in plants. Curr Protein Pept Sci 6, 85-101.

Liang, J., Shah, D. M., Wu, Y., Rosenberger, C. A., and Hakimi, S. M. U.S. Pat. No. 6,916,970 for Transgenic plants comprising antifungal polypeptides from alfalfa and methods for controlling plant pathogenic fungi; issued Jul. 12, 2005.

Mankin, S. L, G. C. Allen, and W. F. Thompson. 1997. Introduction of a Plant Intron into the Luciferase Gene of *Photinus Pyralis*. Plant Mol Biol Rep 15(2): 186-196.

McElroy, D, Zhang W, Cao J, Wu R. 1990. Isolation of an efficient actin promoter for use in rice transformation. The Plant Cell, Vol. 2, 163-171

Reiser J, Glumoff V, Kalin M, Ochsner U. (1990) Transfer and expression of heterologous genes in yeasts other than *Saccharomyces cerevisiae*. Adv Biochem Eng Biotechnol.; 43:75-102.

Sambrook, J., and Russell, D. W. (2001). Molecular Cloning: A Laboratory Manual. (Cold Sprong Harbor Laboratory Press, Cold Sprong Harbor, N.Y.).

Seong, K., Hou, Z., Tracy, M., Kistler, H. C., and Xu, J.-R. (2005). Random insertional mutagensis identifies genes associated with virulence in the wheat scab fungus *Fusarium graminearum*. Phytopathology 95, 744-750.

Sidorov, V, Gilbertson, L, Addae, P, and Duncan, D. (2006) *Agrobacterium*-mediated transformation of seedling-derived maize callus. Plant Cell Rep. 2006 April; 25(4):320-8. (Epub 2005 Oct. 27)

Spelbrink, R. G., Dilmac, N., Allen, A., Smith, T. J., Shah, D. M., and Hockerman, G. H. (2004). Differential antifungal and calcium channel-blocking activity among structurally related plant defensins. Plant Physiol 135, 2055-2067.

Terras, F. R., Schoofs, H. M., De Bolle, M. F., Van Leuven, F., Rees, S. B., Vanderleyden, J., Cammue, B. P., and Broekaert, W. F. (1992). Analysis of two novel classes of plant antifungal proteins from radish (*Raphanus sativus* L.) seeds. J Biol Chem 267, 15301-15309.

Thevissen, K., Francois, I. E., Aerts, A. M., and Cammue, B. P. (2005). Fungal sphingolipids as targets for the development of selective antifungal therapeutics. Curr Drug Targets 6, 923-928.

Thevissen, K., Ghazi, A., De Samblanx, G. W., Brownlee, C., Osborn, R. W., and Broekaert, W. F. (1996). Fungal membrane responses induced by plant defensins and thionins. J Biol Chem 271, 15018-15025.

Thevissen, K., Cammue, B. P., Lemaire, K., Winderickx, J., Dickson, R. C., Lester, R. L., Ferket, K. K., Van Even, F., Parret, A. H., and Broekaert, W. F. (2000). A gene encoding a sphingolipid biosynthesis enzyme determines the sensitivity of *Saccharomyces cerevisiae* to an antifungal plant defensin from *dahlia* (*Dahlia merckii*). Proc Natl Acad Sci USA 97, 9531-9536.

Thevissen, K., Warnecke, D. C., Francois, I. E., Leipelt, M., Heinz, E., Ott, C., Zahringer, U., Thomma, B. P., Ferket, K.

K., and Cammue, B. P. (2004). Defensins from insects and plants interact with fungal glucosylceramides. J Biol Chem 279, 3900-3905.

Thomma, B. P., Cammue, B. P., and Thevissen, K. (2003). Mode of action of plant defensins suggests therapeutic potential. Curr Drug Targets Infect Disord 3, 1-8.

Thomma, B. P. H. J., Cammue, B. P. A., and Thevissen, K. (2002). Plant defensins. Planta 216, 193-202.

Using Antibodies: A Laboratory Manual. (1999). Ed. Harlow and Lane. Cold Spring Harbor Laboratory Press.

Vasil V, Clancy M, Ferl R J, Vasil I K, Hannah L C. (1989) Increased Gene Expression by the First Intron of Maize Shrunken-1 Locus in Grass Species. Plant Physiol. 1989 December; 91(4): 1575-1579.

Wesley S V, Helliwell C A, Smith N A, Wang M B, Rouse D T, Liu Q, Gooding P S, Singh S P, Abbott D, Stoutjesdijk P A, Robinson S P, Gleave A P, Green A G, Waterhouse P M. (2001). Construct design for efficient, effective and high-throughput gene silencing in plants. Plant J. 27(6):581-590.

What is claimed is:

1. A transgenic plant comprising a DNA construct that comprises a heterologous promoter, a sequence that encodes a MtDef4 polypeptide with at least 90% sequence identity to SEQ ID NO: 112, and a polyadenylation sequence, wherein said promoter, said sequence encoding a MtDef4 polypeptide and said polyadenylation sequence are operably linked and wherein said promoter and said polyadenylation sequence of said DNA construct provide for expression of operably linked sequences when introduced into a transgenic plant, and wherein said plant expresses a plant pathogenic fungus inhibitory amount of said MtDef4 polypeptide of at least 1.0 PPM.

2. The transgenic plant of claim 1, wherein said transgenic plant is a monocot plant.

3. The transgenic plant of claim 2, wherein said monocot plant is selected from the group consisting of barley, corn, flax, oat, rice, rye, sorghum, turf grass, sugarcane, and wheat.

4. The transgenic plant of claim 1, wherein said DNA construct comprises a polynucleotide sequence selected from the group consisting of SEQ ID NO:74, SEQ ID NO:75, SEQ ID NO:76, and SEQ ID NO:150.

5. The transgenic plant of claim 1, wherein said transgenic plant is a dicot plant.

6. The transgenic plant of claim 5, wherein said dicot plant is selected from the group consisting of alfalfa, *Arabidopsis*, barrel medic, banana, broccoli, bean, cabbage, canola, carrot, cassava, cauliflower, celery, citrus, cotton, a cucurbit, eucalyptus, garlic, grape, onion, lettuce, pea, peanut, pepper, potato, poplar, pine, sunflower, safflower, soybean, strawberry, sugar beet, sweet potato, tobacco, and tomato.

7. The transgenic plant of claim 1, wherein said DNA construct further comprises a sequence encoding a signal peptide and a sequence encoding a targeting peptide that provides for localization of said MtDef4 polypeptide in endoplasmic reticulum (ER), wherein said sequences encoding said signal peptide and said targeting peptide are operably linked to said sequence that encodes a MtDef4 polypeptide.

8. A transgenic plant that inhibits the growth of a plant pathogenic fungus, wherein said transgenic plant is produced by a process comprising the steps of:

a. introducing a DNA construct into a plant, a plant cell, or a plant tissue, that said DNA construct comprising a heterologous promoter, a sequence that encodes a MtDef4 polypeptide with at least 90% sequence identity to SEQ ID NO: 112, and a polyadenylation sequence, wherein said promoter, said sequence encoding a MtDef4 polypeptide and said polyadenylation sequence are operably linked and wherein said promoter and said polyadenylation sequence provide for expression of operably linked sequences when introduced into a transgenic plant; and b. obtaining a transgenic plant comprising said DNA construct, wherein said transgenic plant expresses a plant pathogenic fungus inhibitory amount of said MtDef4 polypeptide of at least 1.0 PPM.

9. The transgenic plant of claim 8, wherein said transgenic plant is a monocot plant.

10. The transgenic plant of claim 8, wherein said transgenic plant is a dicot plant.

11. The transgenic plant of claim 8, wherein said DNA construct is introduced into said plant, a plant cell or a plant tissue in step (a) by a method selected from the group consisting of particle bombardment, DNA transfection, DNA electroporation and T-DNA mediated transformation.

12. The transgenic plant of claim 8 wherein said DNA construct further comprises a sequence encoding a selectable marker and wherein said transgenic plant is obtained in step (b) by growing said plant, plant cell, or plant tissue under conditions requiring expression of said selectable marker.

13. The transgenic plant of claim 8, wherein said DNA construct further comprises a sequence encoding a scoreable marker.

14. The transgenic plant of claim 8, wherein said DNA construct further comprises a sequence encoding a signal peptide and a sequence encoding a targeting peptide that provides for localization of said MtDef4 polypeptide in endoplasmic reticulum (ER), wherein said sequences encoding said signal peptide and said targeting peptide are operably linked to said sequence that encodes a MtDef4 polypeptide.

15. The transgenic plant of claim 8, wherein said plant pathogenic fungus is selected from the group consisting of an *Alternaria* sp., an *Ascochyta* sp., a *Botrytis* sp.; a *Cercospora* sp., a *Colletotrichum* sp., a *Diplodia* sp., an *Erysiphe* sp., a *Fusarium* sp., *Gaeumanomyces* sp., *Helminthosporium* sp., *Magnaporthe grisea*, *Macrophomina* sp., a *Nectria* sp., a *Peronospora* sp., *Phakopsora pachyrhizi*, *Phialophora gregata*, a *Phoma* sp., a *Phymatotrichum* sp., a *Phytophthora* sp., a *Plasmopara* sp., a *Puccinia* sp., a *Podosphaera* sp., a *Pyrenophora* sp., a *Pyricularia* sp, a *Pythium* sp., a *Rhizoctonia* sp., a *Scerotium* sp., a *Sclerotinia* sp., a *Septoria* sp., *Stenocarpella maydis*, a *Thielaviopsis* sp., an *Uncinula* sp, a *Venturia* sp., and a *Verticillium* sp.

16. A method of obtaining a transgenic plant that inhibits the growth of a plant pathogenic fungus, said method comprising the steps of:
   a. introducing a DNA construct into a plant, a plant cell, or a plant tissue, said DNA construct comprising a heterologous promoter, a sequence that encodes a MtDef4 polypeptide with at least 90% sequence identity to SEQ ID NO: 112, and a polyadenylation sequence, wherein said promoter, said sequence encoding a MtDef4 polypeptide, and said polyadenylation sequence are operably linked and wherein said promoter and said polyadenylation sequence provide for expression of operably linked sequences when introduced into a transgenic plant; and
   b. obtaining a transgenic plant comprising said DNA construct that expresses a plant pathogenic fungus inhibitory amount of said MtDef4 polypeptide, thereby obtaining a transgenic plant that inhibits the growth of a plant pathogenic fungus.

17. The method of claim 16, wherein said transgenic plant is a monocot plant.

18. The method of claim 16, wherein said transgenic plant is a dicot plant.

19. The method of claim 16, wherein said DNA construct is introduced into said plant, a plant cell or a plant tissue in step (a) by a method selected from the group consisting of particle bombardment, DNA transfection, DNA electroporation and T-DNA mediated transformation.

20. The method of claim 16, wherein said DNA construct further comprises a sequence encoding a selectable marker and wherein said transgenic plant is obtained in step (b) by growing said plant, plant cell, or plant tissue under conditions requiring expression of said selectable marker.

21. The method of claim 16, wherein said DNA construct further comprises a sequence encoding a scoreable marker.

22. The method of claim 16, wherein said plant pathogenic fungus inhibitory amount of mature MtDef4 polypeptide is at least 1.0 PPM.

23. The method of claim 16, wherein said transgenic plant obtained in step (b) co-expresses another defensin protein.

24. The method of claim 16, wherein said transgenic plant obtained in step (b) co-expresses MsDef1, MtDef2, Rs-AFP1, or Rs-AFP2.

25. The method of claim 16, wherein said DNA construct further comprises a sequence encoding a signal peptide and a sequence encoding a targeting peptide that provides for localization of said MtDef4 polypeptide.

\* \* \* \* \*

UNITED STATES PATENT AND TRADEMARK OFFICE
CERTIFICATE OF CORRECTION

| | | |
|---|---|---|
| PATENT NO. | : 7,825,297 B2 | |
| APPLICATION NO. | : 11/961810 | |
| DATED | : November 2, 2010 | |
| INVENTOR(S) | : Dilip Maganlal Shah and Anita Kay Snyder | |

It is certified that error appears in the above-identified patent and that said Letters Patent is hereby corrected as shown below:

On Page 95, Column 154, Claim 8, Line 44 please delete the word "that" which appears after the "," following the word "tissue" and before the word "said".

On Page 96, Column 156, Claim 25, Line 37 please add after the word "polypeptide" at the end of claim 25 the following: --in endoplasmic reticulum (ER), wherein said sequences encoding said signal peptide and said targeting peptide are operably linked to said sequence that encodes a MtDef4 polypeptide--.

Signed and Sealed this
Eighth Day of February, 2011

David J. Kappos
*Director of the United States Patent and Trademark Office*

SEQUENCE LISTING

```
<160> NUMBER OF SEQ ID NOS: 156

<210> SEQ ID NO 1
<211> LENGTH: 52
<212> TYPE: PRT
<213> ORGANISM: Medicago truncatula

<400> SEQUENCE: 1

Met Val Ala Glu Ala Arg Thr Cys Glu Ser Gln Ser His Lys Phe Lys
1               5                   10                  15

Gly Pro Cys Ala Ser Asp His Asn Cys Ala Ser Val Cys Gln Thr Glu
            20                  25                  30

Arg Phe Ser Gly Gly His Cys Arg Gly Phe Arg Arg Cys Phe Cys
        35                  40                  45

Thr Thr His Cys
    50

<210> SEQ ID NO 2
<211> LENGTH: 75
<212> TYPE: PRT
<213> ORGANISM: Medicago truncatula
<220> FEATURE:
<221> NAME/KEY: misc_feature
<222> LOCATION: (12)..(12)
<223> OTHER INFORMATION: Xaa can be any naturally occurring amino acid

<400> SEQUENCE: 2

Ala Arg Ser Val Pro Leu Val Ser Thr Ile Ser Xaa Phe Leu Leu His
1               5                   10                  15

Leu Val Ala Thr Gly Pro Ser Met Val Ala Glu Ala Arg Thr Cys Glu
            20                  25                  30

Ser Gln Ser His Lys Phe Lys Gly Pro Cys Ala Ser Asp His Asn Cys
        35                  40                  45

Ala Ser Val Cys Gln Thr Glu Arg Phe Ser Gly Gly His Cys Arg Gly
    50                  55                  60

Phe Arg Arg Arg Cys Phe Cys Thr Thr His Cys
65                  70                  75

<210> SEQ ID NO 3
<211> LENGTH: 46
<212> TYPE: PRT
<213> ORGANISM: Medicago truncatula
<220> FEATURE:
<221> NAME/KEY: misc_feature
<222> LOCATION: (38)..(38)
<223> OTHER INFORMATION: Xaa can be any naturally occurring amino acid

<400> SEQUENCE: 3

Thr Cys Glu Ser Gln Ser His Lys Phe Lys Gly Pro Cys Ala Ser Asp
1               5                   10                  15
```

His Asn Cys Ala Ser Val Cys Gln Thr Glu Arg Phe Ser Gly Gly His
            20                  25                  30

Cys Arg Gly Phe Arg Xaa Arg Cys Phe Cys Thr Thr His Cys
            35                  40                  45

<210> SEQ ID NO 4
<211> LENGTH: 54
<212> TYPE: PRT
<213> ORGANISM: Medicago truncatula

<400> SEQUENCE: 4

Pro Ser Met Val Ala Glu Ala Arg Thr Cys Glu Ser Gln Ser His Lys
1               5                   10                  15

Phe Lys Gly Pro Cys Ala Ser Asp His Asn Cys Ala Ser Val Cys Gln
            20                  25                  30

Thr Glu Arg Phe Ser Gly Gly His Cys Arg Gly Phe Arg Arg Arg Cys
            35                  40                  45

Phe Cys Thr Thr His Cys
            50

<210> SEQ ID NO 5
<211> LENGTH: 76
<212> TYPE: PRT
<213> ORGANISM: Medicago truncatula

<400> SEQUENCE: 5

Met Ala Arg Ser Val Phe Leu Val Ser Thr Ile Phe Val Phe Leu Leu
1               5                   10                  15

Val Leu Val Ala Thr Gly Pro Ser Met Val Ala Glu Ala Arg Thr Cys
            20                  25                  30

Glu Ser Gln Ser His Lys Phe Lys Gly Pro Cys Ala Ser Asp His Asn
            35                  40                  45

Cys Ala Ser Val Cys Gln Thr Glu Arg Phe Ser Gly Gly His Cys Arg
        50                  55                  60

Gly Phe Arg Arg Arg Cys Phe Cys Thr Thr His Cys
65                  70                  75

<210> SEQ ID NO 6
<211> LENGTH: 32
<212> TYPE: PRT
<213> ORGANISM: Medicago truncatula

<400> SEQUENCE: 6

Ser Asp His Asn Cys Ala Ser Val Cys Gln Thr Glu Arg Phe Ser Gly
1               5                   10                  15

Gly His Cys Arg Gly Phe Arg Arg Arg Cys Phe Cys Thr Thr His Cys
            20                  25                  30

<210> SEQ ID NO 7
<211> LENGTH: 76
<212> TYPE: PRT
<213> ORGANISM: Medicago truncatula

<400> SEQUENCE: 7

Met Ala Arg Ser Val Ser Leu Val Phe Thr Ile Phe Val Phe Leu Leu
1               5                   10                  15

Leu Val Val Ala Thr Gly Pro Ser Met Val Ala Glu Ala Arg Thr Cys
            20                  25                  30

Glu Ser Gln Ser His Lys Phe Lys Gly Pro Cys Ala Ser Asp His Asn

```
                35                  40                  45
Cys Ala Ser Val Cys Gln Thr Glu Arg Phe Ser Gly Gly His Cys Arg
     50                  55                  60

Gly Phe Arg Arg Arg Cys Phe Cys Thr Thr His Cys
 65                  70                  75

<210> SEQ ID NO 8
<211> LENGTH: 20
<212> TYPE: PRT
<213> ORGANISM: Medicago truncatula

<400> SEQUENCE: 8

Arg Phe Ser Gly Gly His Cys Arg Gly Phe Arg Arg Cys Phe Cys
 1               5                  10                  15

Thr Thr His Cys
             20

<210> SEQ ID NO 9
<211> LENGTH: 68
<212> TYPE: PRT
<213> ORGANISM: Medicago truncatula

<400> SEQUENCE: 9

Ser Thr Ile Phe Val Phe Leu Leu Phe Leu Val Ala Thr Gly Pro Ser
 1               5                  10                  15

Val Val Ala Glu Ala Arg Thr Cys Glu Ser Gln Ser His Lys Phe Lys
                 20                  25                  30

Gly Pro Cys Ala Ser Asp His Asn Cys Ala Ser Val Cys Gln Thr Glu
             35                  40                  45

Arg Phe Ser Gly Gly His Cys Arg Gly Phe Arg Arg Arg Cys Phe Cys
     50                  55                  60

Thr Thr His Cys
 65

<210> SEQ ID NO 10
<211> LENGTH: 29
<212> TYPE: PRT
<213> ORGANISM: Medicago truncatula

<400> SEQUENCE: 10

Asn Cys Ala Ser Val Cys Gln Thr Glu Arg Phe Ser Gly Gly His Cys
 1               5                  10                  15

Arg Gly Phe Arg Arg Cys Phe Cys Thr Thr His Cys
             20                  25

<210> SEQ ID NO 11
<211> LENGTH: 52
<212> TYPE: PRT
<213> ORGANISM: Medicago truncatula

<400> SEQUENCE: 11

Met Val Ala Glu Ala Arg Thr Cys Glu Ser Gln Ser His Lys Phe Lys
 1               5                  10                  15

Gly Pro Cys Ala Asn Asp His Asn Cys Ala Ser Val Cys Gln Thr Glu
             20                  25                  30

Arg Phe Ser Gly Gly His Cys Arg Gly Phe Arg Arg Arg Cys Phe Cys
         35                  40                  45

Thr Thr His Trp
     50
```

```
<210> SEQ ID NO 12
<211> LENGTH: 76
<212> TYPE: PRT
<213> ORGANISM: Medicago truncatula

<400> SEQUENCE: 12

Met Gly Ser Phe Ser Ser Phe Gly Phe Thr Ile Phe Val Phe Leu Leu
1               5                   10                  15

Leu Leu Val Ala Thr Gly Pro Ser Met Val Ala Glu Ala Arg Thr Cys
            20                  25                  30

Glu Ser Gln Ser His Lys Phe Lys Gly Pro Cys Ala Ser Asp His Asn
        35                  40                  45

Cys Ala Ser Val Cys Gln Thr Glu Arg Phe Ser Gly Gly His Cys Arg
    50                  55                  60

Gly Phe Arg Arg Arg Cys Phe Cys Thr Thr His Cys
65                  70                  75

<210> SEQ ID NO 13
<211> LENGTH: 41
<212> TYPE: PRT
<213> ORGANISM: Medicago truncatula

<400> SEQUENCE: 13

Ser His Lys Phe Lys Gly Pro Cys Ala Ser Asp His Asn Cys Ala Ser
1               5                   10                  15

Val Cys Gln Thr Glu Arg Phe Ser Gly Gly His Cys Arg Gly Phe Arg
            20                  25                  30

Arg Arg Cys Phe Cys Thr Thr His Cys
        35                  40

<210> SEQ ID NO 14
<211> LENGTH: 52
<212> TYPE: PRT
<213> ORGANISM: Medicago truncatula

<400> SEQUENCE: 14

Met Val Ala Glu Ala Arg Thr Cys Glu Ser Gln Ser His Lys Phe Lys
1               5                   10                  15

Gly Pro Cys Ala Ser Asp His Asn Cys Ala Ser Val Cys Gln Thr Glu
            20                  25                  30

Arg Phe Ser Gly Gly His Cys Arg Gly Phe Arg Arg Arg Cys Phe Cys
        35                  40                  45

Thr Thr His Cys
    50

<210> SEQ ID NO 15
<211> LENGTH: 64
<212> TYPE: PRT
<213> ORGANISM: Medicago truncatula

<400> SEQUENCE: 15

Val Phe Leu Leu Leu Val Ala Thr Gly Pro Ser Met Val Ala Glu
1               5                   10                  15

Ala Arg Thr Cys Glu Ser Gln Ser His Lys Phe Lys Gly Pro Cys Ala
            20                  25                  30

Ser Asp His Asn Cys Ala Ser Val Cys Gln Thr Glu Arg Phe Ser Gly
        35                  40                  45

Gly His Cys Arg Gly Phe Arg Arg Arg Cys Phe Cys Thr Thr His Cys
    50                  55                  60
```

```
<210> SEQ ID NO 16
<211> LENGTH: 70
<212> TYPE: PRT
<213> ORGANISM: Medicago truncatula

<400> SEQUENCE: 16

Leu Val Ser Thr Ile Phe Val Phe Leu Leu Leu Val Ala Thr Gly
1               5                   10                  15

Pro Ser Met Val Ala Glu Ala Arg Thr Cys Glu Ser Gln Ser His Lys
            20                  25                  30

Phe Lys Gly Pro Cys Ala Ser Asp His Asn Cys Ala Ser Val Cys Gln
        35                  40                  45

Thr Glu Arg Phe Ser Gly Gly His Cys Arg Gly Phe Arg Arg Cys
    50                  55                  60

Phe Cys Thr Thr His Cys
65                  70

<210> SEQ ID NO 17
<211> LENGTH: 72
<212> TYPE: PRT
<213> ORGANISM: Medicago truncatula

<400> SEQUENCE: 17

Thr Ser Leu Val Ser Thr Ile Phe Val Phe Leu Leu Leu Val Ala
1               5                   10                  15

Thr Gly Pro Ser Met Val Ala Glu Ala Arg Thr Cys Glu Ser Gln Ser
            20                  25                  30

His Lys Phe Lys Gly Pro Cys Ala Ser Asp His Asn Cys Ala Ser Val
        35                  40                  45

Cys Gln Thr Glu Arg Phe Ser Gly Gly His Cys Arg Gly Phe Arg Arg
    50                  55                  60

Arg Cys Phe Cys Thr Thr His Cys
65                  70

<210> SEQ ID NO 18
<211> LENGTH: 73
<212> TYPE: PRT
<213> ORGANISM: Medicago truncatula

<400> SEQUENCE: 18

Gly Thr Ser Leu Val Ser Thr Ile Phe Val Phe Leu Leu Leu Val
1               5                   10                  15

Ala Thr Gly Pro Ser Met Val Ala Glu Ala Arg Thr Cys Glu Ser Gln
            20                  25                  30

Ser His Lys Phe Lys Gly Pro Cys Ala Ser Asp His Asn Cys Ala Ser
        35                  40                  45

Val Cys Gln Thr Glu Arg Phe Ser Gly Gly His Cys Arg Gly Phe Arg
    50                  55                  60

Arg Arg Cys Phe Cys Thr Thr His Cys
65                  70

<210> SEQ ID NO 19
<211> LENGTH: 72
<212> TYPE: PRT
<213> ORGANISM: Medicago truncatula

<400> SEQUENCE: 19

Thr Ser Leu Val Ser Thr Ile Phe Val Phe Leu Leu Leu Val Ala
```

```
                1               5                  10                  15
Thr Gly Pro Ser Met Val Ala Glu Ala Arg Thr Cys Glu Ser Gln Ser
                    20                  25                  30

His Lys Phe Lys Gly Pro Cys Ala Ser Asp His Asn Cys Ala Ser Val
            35                  40                  45

Cys Gln Thr Glu Arg Phe Ser Gly Gly His Cys Arg Gly Phe Arg Arg
        50                  55                  60

Arg Cys Phe Cys Thr Thr His Cys
65                  70

<210> SEQ ID NO 20
<211> LENGTH: 71
<212> TYPE: PRT
<213> ORGANISM: Medicago truncatula

<400> SEQUENCE: 20

His Gln Val Ser Thr Ile Phe Val Phe Leu Leu Leu Val Ala Thr
1               5                  10                  15

Gly Pro Ser Met Val Ala Glu Ala Arg Thr Cys Glu Ser Gln Ser His
                    20                  25                  30

Lys Phe Lys Gly Pro Cys Ala Ser Asp His Asn Cys Ala Ser Val Cys
            35                  40                  45

Gln Thr Glu Arg Phe Ser Gly Gly His Cys Arg Gly Phe Arg Arg Arg
        50                  55                  60

Cys Phe Cys Thr Thr His Cys
65                  70

<210> SEQ ID NO 21
<211> LENGTH: 66
<212> TYPE: PRT
<213> ORGANISM: Medicago truncatula

<400> SEQUENCE: 21

Ile Phe Val Phe Leu Leu Leu Val Ala Thr Gly Pro Ser Met Val
1               5                  10                  15

Ala Glu Ala Arg Thr Cys Glu Ser Gln Ser His Lys Phe Lys Gly Pro
                    20                  25                  30

Cys Ala Ser Asp His Asn Cys Ala Ser Val Cys Gln Thr Glu Arg Phe
            35                  40                  45

Ser Gly Gly His Cys Arg Gly Phe Arg Arg Arg Cys Phe Cys Thr Thr
        50                  55                  60

His Cys
65

<210> SEQ ID NO 22
<211> LENGTH: 52
<212> TYPE: PRT
<213> ORGANISM: Medicago truncatula

<400> SEQUENCE: 22

Met Val Ala Glu Ala Arg Thr Cys Glu Ser Gln Ser His Lys Phe Lys
1               5                  10                  15

Gly Pro Cys Ala Ser Asp His Asn Cys Ala Ser Val Cys Gln Thr Glu
                    20                  25                  30

Arg Phe Ser Gly Gly His Cys Arg Gly Phe Arg Arg Arg Cys Phe Cys
            35                  40                  45

Thr Thr His Cys
        50
```

<210> SEQ ID NO 23
<211> LENGTH: 53
<212> TYPE: PRT
<213> ORGANISM: Medicago truncatula

<400> SEQUENCE: 23

Ser Met Val Ala Glu Ala Arg Thr Cys Glu Ser Gln Ser His Lys Phe
1               5                   10                  15

Lys Gly Pro Cys Ala Ser Asp His Asn Cys Ala Ser Val Cys Gln Thr
            20                  25                  30

Glu Arg Phe Ser Gly Gly His Cys Arg Gly Phe Arg Arg Cys Phe
        35                  40                  45

Cys Thr Thr His Cys
    50

<210> SEQ ID NO 24
<211> LENGTH: 52
<212> TYPE: PRT
<213> ORGANISM: Medicago truncatula

<400> SEQUENCE: 24

Met Val Ala Glu Ala Arg Thr Cys Glu Ser Gln Ser His Lys Phe Lys
1               5                   10                  15

Gly Pro Cys Ala Ser Asp His Asn Cys Ala Ser Val Cys Gln Thr Glu
            20                  25                  30

Arg Phe Ser Gly Gly His Cys Arg Gly Phe Arg Arg Cys Phe Cys
        35                  40                  45

Thr Thr His Cys
    50

<210> SEQ ID NO 25
<211> LENGTH: 72
<212> TYPE: PRT
<213> ORGANISM: Medicago truncatula

<400> SEQUENCE: 25

Val Pro Leu Val Ser Thr Ile Phe Val Phe Leu Leu Leu Val Ala
1               5                   10                  15

Thr Gly Pro Ser Met Val Ala Glu Ala Arg Thr Cys Glu Ser Gln Ser
            20                  25                  30

His Lys Phe Lys Gly Pro Cys Ala Ser Asp His Asn Cys Ala Ser Val
        35                  40                  45

Cys Gln Thr Glu Arg Phe Ser Gly Gly His Cys Arg Gly Phe Arg Arg
    50                  55                  60

Arg Cys Phe Cys Thr Thr His Cys
65                  70

<210> SEQ ID NO 26
<211> LENGTH: 74
<212> TYPE: PRT
<213> ORGANISM: Medicago truncatula

<400> SEQUENCE: 26

Gly Ser Val Pro Leu Val Ser Thr Ile Phe Val Phe Leu Leu Leu
1               5                   10                  15

Val Ala Thr Gly Pro Ser Met Val Ala Glu Ala Arg Thr Cys Glu Ser
            20                  25                  30

Gln Ser His Lys Phe Lys Gly Pro Cys Ala Ser Asp His Asn Cys Ala

```
                35                  40                  45
Ser Val Cys Gln Thr Glu Arg Phe Ser Gly Gly His Cys Arg Gly Phe
    50                  55                  60

Arg Arg Arg Cys Phe Cys Thr Thr His Cys
65                  70

<210> SEQ ID NO 27
<211> LENGTH: 22
<212> TYPE: PRT
<213> ORGANISM: Medicago truncatula

<400> SEQUENCE: 27

Met Ala Arg Ser Val Pro Leu Val Ser Thr Ile Phe Val Phe Leu Leu
1               5                   10                  15

Leu Leu Val Ala Thr Gly
            20

<210> SEQ ID NO 28
<211> LENGTH: 55
<212> TYPE: PRT
<213> ORGANISM: Medicago truncatula

<400> SEQUENCE: 28

Gly Pro Ser Met Val Ala Glu Ala Arg Thr Cys Glu Ser Gln Ser His
1               5                   10                  15

Lys Phe Lys Gly Pro Cys Ala Ser Asp His Asn Cys Ala Ser Val Cys
            20                  25                  30

Gln Thr Glu Arg Phe Ser Gly Gly His Cys Arg Gly Phe Arg Arg Arg
        35                  40                  45

Cys Phe Cys Thr Thr His Cys
    50                  55

<210> SEQ ID NO 29
<211> LENGTH: 55
<212> TYPE: PRT
<213> ORGANISM: Medicago truncatula

<400> SEQUENCE: 29

Gly Pro Ser Met Val Ala Glu Ala Arg Thr Cys Glu Ser Gln Ser His
1               5                   10                  15

Lys Phe Lys Gly Pro Cys Ala Ser Asp His Asn Cys Ala Ser Val Cys
            20                  25                  30

Gln Thr Glu Arg Phe Ser Gly Gly His Cys Arg Gly Phe Arg Arg Arg
        35                  40                  45

Cys Phe Cys Thr Thr His Cys
    50                  55

<210> SEQ ID NO 30
<211> LENGTH: 57
<212> TYPE: PRT
<213> ORGANISM: Medicago truncatula

<400> SEQUENCE: 30

Ala Thr Gly Pro Ser Met Val Ala Glu Ala Arg Thr Cys Glu Ser Gln
1               5                   10                  15

Ser His Lys Phe Lys Gly Pro Cys Ala Ser Asp His Asn Cys Ala Ser
            20                  25                  30

Val Cys Gln Thr Glu Arg Phe Ser Gly Gly His Cys Arg Gly Phe Arg
        35                  40                  45
```

```
Arg Arg Cys Phe Cys Thr Thr His Cys
    50                  55
```

<210> SEQ ID NO 31
<211> LENGTH: 64
<212> TYPE: PRT
<213> ORGANISM: Medicago truncatula

<400> SEQUENCE: 31

```
Val Phe Leu Leu Leu Val Ala Thr Gly Pro Ser Met Val Ala Glu
1               5                   10                  15

Ala Arg Thr Cys Glu Ser Gln Ser His Lys Phe Lys Gly Pro Cys Ala
                20                  25                  30

Ser Asp His Asn Cys Ala Ser Val Cys Gln Thr Glu Arg Phe Ser Gly
            35                  40                  45

Gly His Cys Arg Gly Phe Arg Arg Cys Phe Cys Thr Thr His Cys
        50                  55                  60
```

<210> SEQ ID NO 32
<211> LENGTH: 73
<212> TYPE: PRT
<213> ORGANISM: Medicago truncatula

<400> SEQUENCE: 32

```
Ser Val Pro Leu Val Ser Thr Ile Phe Val Phe Leu Leu Leu Val
1               5                   10                  15

Ala Thr Gly Pro Ser Met Val Ala Glu Ala Arg Thr Cys Glu Ser Gln
                20                  25                  30

Ser His Lys Phe Lys Gly Pro Cys Ala Ser Asp His Asn Cys Ala Ser
            35                  40                  45

Val Cys Gln Thr Glu Arg Phe Ser Gly Gly His Cys Arg Gly Phe Arg
        50                  55                  60

Arg Arg Cys Phe Cys Thr Thr His Cys
65                  70
```

<210> SEQ ID NO 33
<211> LENGTH: 76
<212> TYPE: PRT
<213> ORGANISM: Medicago truncatula

<400> SEQUENCE: 33

```
Met Ala Arg Ser Val Pro Leu Val Ser Thr Ile Phe Val Phe Leu Leu
1               5                   10                  15

Leu Leu Val Ala Thr Gly Pro Ser Met Val Ala Glu Ala Arg Thr Cys
                20                  25                  30

Glu Ser Gln Ser His Lys Phe Lys Gly Pro Cys Ala Ser Asp His Asn
            35                  40                  45

Cys Ala Ser Val Cys Gln Thr Glu Arg Phe Phe Gly Gly His Cys Arg
        50                  55                  60

Gly Phe Arg Arg Arg Cys Phe Cys Thr Thr His Cys
65                  70                  75
```

<210> SEQ ID NO 34
<211> LENGTH: 26
<212> TYPE: PRT
<213> ORGANISM: Medicago truncatula
<220> FEATURE:
<221> NAME/KEY: misc_feature
<222> LOCATION: (13)..(13)
<223> OTHER INFORMATION: Xaa can be any naturally occurring amino acid
<220> FEATURE:

```
<221> NAME/KEY: misc_feature
<222> LOCATION: (18)..(19)
<223> OTHER INFORMATION: Xaa can be any naturally occurring amino acid

<400> SEQUENCE: 34

Phe Val Cys Gln Thr Glu Arg Phe Phe Gly Gly His Xaa Arg Gly Phe
1               5                   10                  15

Arg Xaa Xaa Cys Phe Cys Thr Thr His Cys
            20                  25

<210> SEQ ID NO 35
<211> LENGTH: 20
<212> TYPE: PRT
<213> ORGANISM: Medicago truncatula

<400> SEQUENCE: 35

Ala Arg Gly Asp His Asn Cys Ala Ser Val Cys Gln Thr Glu Arg Phe
1               5                   10                  15

Ser Gly Gly His
            20

<210> SEQ ID NO 36
<211> LENGTH: 14
<212> TYPE: PRT
<213> ORGANISM: Medicago truncatula

<400> SEQUENCE: 36

Cys Arg Gly Phe Arg Arg Arg Cys Phe Cys Thr Thr His Cys
1               5                   10

<210> SEQ ID NO 37
<211> LENGTH: 161
<212> TYPE: DNA
<213> ORGANISM: Medicago truncatula

<400> SEQUENCE: 37
acattgttaa atacatgttt aagaaattaa tccctatatg ttaagaaaaa aaagatgatg      60
gatccatcac cttttttttac ttgttcatgt tttggaataa aggctagcta gctatccatt    120
ttattatggg tttctttcaa aaaaaaaaaa aaaaaaaaa a                          161

<210> SEQ ID NO 38
<211> LENGTH: 23
<212> TYPE: PRT
<213> ORGANISM: Medicago truncatula
<220> FEATURE:
<221> NAME/KEY: misc_feature
<222> LOCATION: (16)..(16)
<223> OTHER INFORMATION: Xaa can be any naturally occurring amino acid

<400> SEQUENCE: 38

Gln Thr Glu Arg Phe Phe Gly Gly His Cys Arg Gly Phe Arg Arg Xaa
1               5                   10                  15

Cys Phe Cys Thr Thr His Cys
            20

<210> SEQ ID NO 39
<211> LENGTH: 57
<212> TYPE: PRT
<213> ORGANISM: Medicago truncatula
<220> FEATURE:
<221> NAME/KEY: misc_feature
<222> LOCATION: (9)..(9)
<223> OTHER INFORMATION: Xaa can be any naturally occurring amino acid
<220> FEATURE:
```

```
<221> NAME/KEY: misc_feature
<222> LOCATION: (24)..(25)
<223> OTHER INFORMATION: Xaa can be any naturally occurring amino acid
<220> FEATURE:
<221> NAME/KEY: misc_feature
<222> LOCATION: (30)..(32)
<223> OTHER INFORMATION: Xaa can be any naturally occurring amino acid
<220> FEATURE:
<221> NAME/KEY: misc_feature
<222> LOCATION: (50)..(50)
<223> OTHER INFORMATION: Xaa can be any naturally occurring amino acid

<400> SEQUENCE: 39

Ala Thr Gly Pro Ser Met Val Ala Xaa Ala Arg Thr Cys Glu Ser Gln
1               5                   10                  15

Ser His Lys Phe Lys Gly Pro Xaa Xaa Ser Asp His Asn Xaa Xaa Xaa
            20                  25                  30

Val Cys Gln Thr Glu Arg Phe Phe Gly Gly His Cys Arg Gly Phe Arg
        35                  40                  45

Arg Xaa Cys Phe Cys Thr Thr His Cys
    50                  55

<210> SEQ ID NO 40
<211> LENGTH: 12
<212> TYPE: PRT
<213> ORGANISM: Medicago truncatula

<400> SEQUENCE: 40

Gly Phe Arg Arg Arg Cys Phe Cys Thr Thr His Cys
1               5                   10

<210> SEQ ID NO 41
<211> LENGTH: 59
<212> TYPE: PRT
<213> ORGANISM: Medicago truncatula
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (27)..(27)
<223> OTHER INFORMATION: Xaa can be any naturally occurring amino acid
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (34)..(34)
<223> OTHER INFORMATION: Xaa can be any naturally occurring amino acid
<220> FEATURE:
<221> NAME/KEY: misc_feature
<222> LOCATION: (46)..(46)
<223> OTHER INFORMATION: Xaa can be any naturally occurring amino acid

<400> SEQUENCE: 41

Leu Val Ala Xaa Gly Pro Ser Met Val Ala Glu Ala Arg Thr Cys Glu
1               5                   10                  15

Ser Gln Ser Xaa Lys Phe Lys Gly Pro Cys Xaa Ser Asp Xaa Asn Cys
            20                  25                  30

Ala Xaa Val Cys Gln Thr Glu Arg Phe Phe Gly Gly His Xaa Arg Gly
        35                  40                  45

Phe Arg Arg Arg Cys Phe Cys Thr Thr His Cys
```

```
            50                  55

<210> SEQ ID NO 42
<211> LENGTH: 17
<212> TYPE: PRT
<213> ORGANISM: Medicago truncatula

<400> SEQUENCE: 42

Ile Pro His Glu Gly Gly Phe Arg Arg Cys Phe Cys Thr Thr His
1               5                   10                  15

Cys

<210> SEQ ID NO 43
<211> LENGTH: 59
<212> TYPE: PRT
<213> ORGANISM: Medicago truncatula

<400> SEQUENCE: 43

Ser Ala Arg Gly Ala Arg Ser Val Pro Leu Val Ser Thr Ile Phe Val
1               5                   10                  15

Phe Leu Leu Leu Val Ala Thr Gly Pro Ser Met Val Ala Glu Ala
            20                  25                  30

Arg Thr Cys Glu Ser Gln Ser His Lys Phe Lys Gly Pro Cys Ala Ser
        35                  40                  45

Asp His Asn Cys Ala Ser Val Cys Gln Thr Leu
    50                  55

<210> SEQ ID NO 44
<211> LENGTH: 34
<212> TYPE: PRT
<213> ORGANISM: Medicago truncatula

<400> SEQUENCE: 44

Val Phe Leu Leu Leu Val Ala Thr Gly Pro Ser Met Val Ala Glu
1               5                   10                  15

Ala Arg Thr Cys Glu Ser Gln Ser His Lys Phe Lys Gly Pro Cys Ala
            20                  25                  30

Ser Asp

<210> SEQ ID NO 45
<211> LENGTH: 43
<212> TYPE: PRT
<213> ORGANISM: Medicago truncatula

<400> SEQUENCE: 45

Phe Val Phe Leu Leu Leu Val Ala Thr Gly Pro Ser Met Val Ala
1               5                   10                  15

Glu Ala Arg Thr Cys Glu Ser Gln Ser His Lys Phe Lys Gly Pro Cys
            20                  25                  30

Ala Ser Asp His Asn Cys Ala Ser Val Cys Gln
        35                  40

<210> SEQ ID NO 46
<211> LENGTH: 75
<212> TYPE: PRT
<213> ORGANISM: Medicago truncatula

<400> SEQUENCE: 46

Ala Arg Ser Val Pro Leu Val Ser Thr Ile Phe Val Phe Leu Leu Leu
1               5                   10                  15
```

```
Leu Val Ala Thr Gly Pro Ser Met Val Ala Glu Ala Arg Thr Cys Glu
            20                  25                  30

Ser Gln Ser His Lys Phe Lys Gly Pro Cys Ala Ser Asp His Asn Cys
        35                  40                  45

Ala Ser Val Cys Gln Thr Glu Arg Phe Ser Gly Gly His Cys Arg Gly
    50                  55                  60

Phe Arg Arg Arg Cys Phe Cys Thr Thr His Cys
65                  70                  75

<210> SEQ ID NO 47
<211> LENGTH: 76
<212> TYPE: PRT
<213> ORGANISM: Medicago truncatula

<400> SEQUENCE: 47

Met Ala Arg Ser Val Pro Leu Val Ser Thr Ile Phe Val Phe Leu Leu
1               5                   10                  15

Leu Leu Val Ala Thr Gly Pro Ser Met Val Ala Glu Ala Arg Thr Cys
            20                  25                  30

Glu Ser Gln Ser His Lys Phe Lys Gly Pro Cys Ala Ser Asp His Asn
        35                  40                  45

Cys Ala Ser Val Cys Gln Thr Glu Arg Phe Ser Gly Gly His Cys Arg
    50                  55                  60

Gly Phe Arg Arg Arg Cys Phe Cys Thr Thr His Cys
65                  70                  75

<210> SEQ ID NO 48
<211> LENGTH: 75
<212> TYPE: PRT
<213> ORGANISM: Medicago truncatula

<400> SEQUENCE: 48

Ala Arg Ser Val Pro Leu Val Ser Thr Ile Phe Val Phe Leu Leu Leu
1               5                   10                  15

Leu Val Ala Thr Gly Pro Ser Met Val Ala Glu Ala Arg Thr Cys Glu
            20                  25                  30

Ser Gln Ser His Lys Phe Lys Gly Pro Cys Ala Ser Asp His Asn Cys
        35                  40                  45

Ala Ser Val Cys Gln Thr Glu Arg Phe Ser Gly Gly His Cys Arg Gly
    50                  55                  60

Phe Arg Arg Arg Cys Phe Cys Thr Thr His Cys
65                  70                  75

<210> SEQ ID NO 49
<211> LENGTH: 75
<212> TYPE: PRT
<213> ORGANISM: Medicago truncatula

<400> SEQUENCE: 49

Ala Arg Ser Val Pro Leu Val Ser Thr Ile Phe Val Phe Leu Leu Leu
1               5                   10                  15

Leu Val Ala Thr Gly Pro Ser Met Val Ala Glu Ala Arg Thr Cys Glu
            20                  25                  30

Ser Gln Ser His Lys Phe Lys Gly Pro Cys Ala Ser Asp His Asn Cys
        35                  40                  45

Ala Ser Val Cys Gln Thr Glu Arg Phe Ser Gly Gly His Cys Arg Gly
    50                  55                  60

Phe Arg Arg Arg Cys Phe Cys Thr Thr His Cys
```

65              70              75

<210> SEQ ID NO 50
<211> LENGTH: 75
<212> TYPE: PRT
<213> ORGANISM: Medicago truncatula

<400> SEQUENCE: 50

Ala Arg Ser Val Pro Leu Val Ser Thr Ile Phe Val Phe Leu Leu Leu
1               5                   10                  15

Leu Val Ala Thr Gly Pro Ser Met Val Ala Glu Ala Arg Thr Cys Glu
            20                  25                  30

Ser Gln Ser His Lys Phe Lys Gly Pro Cys Ala Ser Asp His Asn Cys
        35                  40                  45

Ala Ser Val Cys Gln Thr Glu Arg Phe Ser Gly Gly His Cys Arg Gly
    50                  55                  60

Phe Arg Arg Arg Cys Phe Cys Thr Thr His Cys
65              70              75

<210> SEQ ID NO 51
<211> LENGTH: 76
<212> TYPE: PRT
<213> ORGANISM: Medicago truncatula

<400> SEQUENCE: 51

Met Ala Arg Ser Val Pro Leu Val Ser Thr Ile Phe Val Phe Leu Leu
1               5                   10                  15

Leu Leu Val Ala Thr Gly Pro Ser Met Val Ala Glu Ala Arg Thr Cys
            20                  25                  30

Glu Ser Gln Ser His Lys Phe Lys Gly Pro Cys Ala Ser Asp His Asn
        35                  40                  45

Cys Ala Ser Val Cys Gln Thr Glu Arg Phe Ser Gly Gly His Cys Arg
    50                  55                  60

Gly Phe Arg Arg Arg Cys Phe Cys Thr Thr His Cys
65              70              75

<210> SEQ ID NO 52
<211> LENGTH: 76
<212> TYPE: PRT
<213> ORGANISM: Medicago truncatula

<400> SEQUENCE: 52

Met Ala Arg Ser Val Pro Leu Val Ser Thr Ile Phe Val Phe Leu Leu
1               5                   10                  15

Leu Leu Val Ala Thr Gly Pro Ser Met Val Ala Glu Ala Arg Thr Cys
            20                  25                  30

Glu Ser Gln Ser His Lys Phe Lys Gly Pro Cys Ala Ser Asp His Asn
        35                  40                  45

Cys Ala Ser Val Cys Gln Thr Glu Arg Phe Ser Gly Gly His Cys Arg
    50                  55                  60

Gly Phe Arg Arg Arg Cys Phe Cys Thr Thr His Cys
65              70              75

<210> SEQ ID NO 53
<211> LENGTH: 76
<212> TYPE: PRT
<213> ORGANISM: Medicago truncatula

<400> SEQUENCE: 53

```
Met Ala Arg Ser Val Pro Leu Val Ser Thr Ile Phe Val Phe Leu Leu
1               5                   10                  15

Leu Leu Val Ala Thr Gly Pro Ser Met Val Ala Glu Ala Arg Thr Cys
            20                  25                  30

Glu Ser Gln Ser His Lys Phe Lys Gly Pro Cys Ala Ser Asp His Asn
        35                  40                  45

Cys Ala Ser Val Cys Gln Thr Glu Arg Phe Ser Gly Gly His Cys Arg
    50                  55                  60

Gly Phe Arg Arg Arg Cys Phe Cys Thr Thr His Cys
65                  70                  75
```

<210> SEQ ID NO 54
<211> LENGTH: 76
<212> TYPE: PRT
<213> ORGANISM: Medicago truncatula

<400> SEQUENCE: 54

```
Met Ala Arg Ser Val Pro Leu Val Ser Thr Ile Phe Val Phe Leu Leu
1               5                   10                  15

Leu Leu Val Ala Thr Gly Pro Ser Met Val Ala Glu Ala Arg Thr Cys
            20                  25                  30

Glu Ser Gln Ser His Lys Phe Lys Gly Pro Cys Ala Ser Asp His Asn
        35                  40                  45

Cys Ala Ser Val Cys Gln Thr Glu Arg Phe Ser Gly Gly His Cys Arg
    50                  55                  60

Gly Phe Arg Arg Arg Cys Phe Cys Thr Thr His Cys
65                  70                  75
```

<210> SEQ ID NO 55
<211> LENGTH: 76
<212> TYPE: PRT
<213> ORGANISM: Medicago truncatula

<400> SEQUENCE: 55

```
Met Ala Arg Ser Val Pro Leu Val Ser Thr Ile Phe Val Phe Leu Leu
1               5                   10                  15

Leu Leu Val Ala Thr Gly Pro Ser Met Val Ala Glu Ala Arg Thr Cys
            20                  25                  30

Glu Ser Gln Ser His Lys Phe Lys Gly Pro Cys Ala Ser Asp His Asn
        35                  40                  45

Cys Ala Ser Val Cys Gln Thr Glu Arg Phe Ser Gly Gly His Cys Arg
    50                  55                  60

Gly Phe Arg Arg Arg Cys Phe Cys Thr Thr His Cys
65                  70                  75
```

<210> SEQ ID NO 56
<211> LENGTH: 76
<212> TYPE: PRT
<213> ORGANISM: Medicago truncatula

<400> SEQUENCE: 56

```
Met Ala Arg Ser Val Pro Leu Val Ser Thr Ile Phe Val Phe Leu Leu
1               5                   10                  15

Leu Leu Val Ala Thr Gly Pro Ser Met Val Gly Glu Ala Arg Thr Cys
            20                  25                  30

Glu Ser Gln Ser His Lys Phe Lys Gly Pro Cys Ala Ser Asp His Asn
        35                  40                  45

Cys Ala Ser Val Cys Gln Thr Glu Arg Phe Ser Gly Gly His Cys Arg
```

```
                  50                  55                  60
Gly Phe Arg Arg Arg Cys Phe Cys Thr Thr His Cys
 65                  70                  75

<210> SEQ ID NO 57
<211> LENGTH: 76
<212> TYPE: PRT
<213> ORGANISM: Medicago truncatula
<220> FEATURE:
<221> NAME/KEY: misc_feature
<222> LOCATION: (69)..(69)
<223> OTHER INFORMATION: Xaa can be any naturally occurring amino acid

<400> SEQUENCE: 57

Met Ala Arg Ser Val Pro Leu Val Ser Thr Ile Phe Val Phe Leu Leu
 1               5                  10                  15

Leu Leu Val Ala Thr Gly Pro Ser Met Val Ala Glu Ala Arg Thr Cys
                20                  25                  30

Glu Ser Gln Ser His Lys Phe Lys Gly Pro Cys Ala Ser Asp His Asn
            35                  40                  45

Cys Ala Ser Val Cys Gln Thr Glu Arg Phe Ser Gly Gly His Cys Arg
        50                  55                  60

Gly Phe Arg Arg Xaa Cys Phe Cys Thr Thr His Cys
 65                  70                  75

<210> SEQ ID NO 58
<211> LENGTH: 76
<212> TYPE: PRT
<213> ORGANISM: Medicago truncatula

<400> SEQUENCE: 58

Met Ala Arg Ser Val Pro Leu Val Ser Thr Ile Phe Val Phe Leu Leu
 1               5                  10                  15

Leu Leu Val Ala Thr Gly Pro Ser Met Val Ala Glu Ala Arg Thr Cys
                20                  25                  30

Glu Ser Gln Ser His Lys Phe Lys Gly Pro Cys Ala Ser Asp His Asn
            35                  40                  45

Cys Ala Ser Val Cys Gln Thr Glu Arg Phe Ser Gly Gly His Cys Arg
        50                  55                  60

Gly Phe Arg Arg Arg Cys Phe Cys Thr Thr His Cys
 65                  70                  75

<210> SEQ ID NO 59
<211> LENGTH: 76
<212> TYPE: PRT
<213> ORGANISM: Medicago truncatula

<400> SEQUENCE: 59

Met Ala Arg Ser Val Pro Leu Val Ser Thr Ile Phe Val Phe Leu Leu
 1               5                  10                  15

Leu Leu Val Ala Thr Gly Pro Ser Met Val Ala Glu Ala Arg Thr Cys
                20                  25                  30

Glu Ser Gln Ser His Lys Phe Lys Gly Pro Cys Ala Ser Asp His Asn
            35                  40                  45

Cys Ala Ser Val Cys Gln Thr Glu Arg Phe Ser Gly Gly His Cys Arg
        50                  55                  60

Gly Phe Arg Arg Arg Cys Phe Cys Thr Thr His Cys
 65                  70                  75
```

<210> SEQ ID NO 60
<211> LENGTH: 76
<212> TYPE: PRT
<213> ORGANISM: Medicago truncatula

<400> SEQUENCE: 60

Met Ala Arg Ser Val Pro Leu Val Ser Thr Ile Phe Val Phe Leu Leu
1               5                   10                  15

Leu Leu Val Ala Thr Gly Pro Ser Met Val Ala Glu Ala Arg Thr Cys
            20                  25                  30

Glu Ser Gln Ser His Lys Phe Lys Gly Pro Cys Ala Ser Asp His Asn
        35                  40                  45

Cys Ala Ser Val Cys Gln Thr Glu Arg Phe Ser Gly Gly His Cys Arg
    50                  55                  60

Gly Phe Arg Arg Arg Cys Phe Cys Thr Thr His Cys
65                  70                  75

<210> SEQ ID NO 61
<211> LENGTH: 76
<212> TYPE: PRT
<213> ORGANISM: Medicago truncatula

<400> SEQUENCE: 61

Met Ala Arg Ser Val Pro Leu Val Ser Thr Ile Phe Val Phe Leu Leu
1               5                   10                  15

Leu Leu Val Ala Thr Gly Pro Ser Met Val Ala Glu Ala Arg Thr Cys
            20                  25                  30

Glu Ser Gln Ser His Lys Phe Lys Gly Pro Cys Ala Ser Asp His Asn
        35                  40                  45

Cys Ala Ser Val Cys Gln Thr Glu Arg Phe Ser Gly Gly His Cys Arg
    50                  55                  60

Gly Phe Arg Arg Arg Cys Phe Cys Thr Thr His Cys
65                  70                  75

<210> SEQ ID NO 62
<211> LENGTH: 76
<212> TYPE: PRT
<213> ORGANISM: Medicago truncatula

<400> SEQUENCE: 62

Met Ala Arg Ser Val Pro Leu Val Ser Thr Ile Phe Val Phe Leu Leu
1               5                   10                  15

Leu Leu Val Ala Thr Gly Pro Ser Met Val Ala Glu Ala Arg Thr Cys
            20                  25                  30

Glu Ser Gln Ser His Lys Phe Lys Gly Pro Cys Ala Ser Asp His Asn
        35                  40                  45

Cys Ala Ser Val Cys Gln Thr Glu Arg Phe Ser Gly Gly His Cys Arg
    50                  55                  60

Gly Phe Arg Arg Arg Cys Phe Cys Thr Thr His Cys
65                  70                  75

<210> SEQ ID NO 63
<211> LENGTH: 76
<212> TYPE: PRT
<213> ORGANISM: Medicago truncatula

<400> SEQUENCE: 63

Met Ala Arg Ser Val Pro Leu Val Ser Thr Ile Phe Val Phe Leu Leu
1               5                   10                  15

```
Leu Leu Val Ala Thr Gly Pro Ser Met Val Ala Glu Ala Arg Thr Cys
            20                  25                  30

Glu Ser Gln Ser His Lys Phe Lys Gly Pro Cys Ala Ser Asp His Asn
        35                  40                  45

Cys Ala Ser Val Cys Gln Thr Glu Arg Phe Ser Gly Gly His Cys Arg
    50                  55                  60

Gly Phe Arg Arg Arg Cys Phe Cys Thr Thr His Cys
65                  70                  75

<210> SEQ ID NO 64
<211> LENGTH: 76
<212> TYPE: PRT
<213> ORGANISM: Medicago truncatula

<400> SEQUENCE: 64

Met Ala Arg Ser Val Pro Leu Val Ser Thr Ile Phe Val Phe Leu Leu
1               5                   10                  15

Leu Leu Val Ala Thr Gly Pro Ser Met Val Ala Glu Ala Arg Thr Cys
            20                  25                  30

Glu Ser Gln Ser His Lys Phe Lys Gly Pro Cys Ala Ser Asp His Asn
        35                  40                  45

Cys Ala Ser Val Cys Gln Thr Glu Arg Phe Ser Gly Gly His Cys Arg
    50                  55                  60

Gly Phe Arg Arg Arg Cys Phe Cys Thr Thr His Cys
65                  70                  75

<210> SEQ ID NO 65
<211> LENGTH: 76
<212> TYPE: PRT
<213> ORGANISM: Medicago truncatula

<400> SEQUENCE: 65

Met Ala Arg Ser Val Pro Leu Val Ser Thr Ile Phe Val Phe Leu Leu
1               5                   10                  15

Leu Leu Val Ala Thr Gly Pro Ser Met Val Ala Glu Ala Arg Thr Cys
            20                  25                  30

Glu Ser Gln Ser His Lys Phe Lys Gly Pro Cys Ala Ser Asp His Asn
        35                  40                  45

Cys Ala Ser Val Cys Gln Thr Glu Arg Phe Ser Gly Gly His Cys Arg
    50                  55                  60

Gly Phe Arg Arg Arg Cys Phe Cys Thr Thr His Cys
65                  70                  75

<210> SEQ ID NO 66
<211> LENGTH: 76
<212> TYPE: PRT
<213> ORGANISM: Medicago truncatula

<400> SEQUENCE: 66

Met Ala Arg Ser Val Pro Leu Val Ser Thr Ile Phe Val Phe Leu Leu
1               5                   10                  15

Leu Leu Val Ala Thr Gly Pro Ser Met Val Ala Glu Ala Arg Thr Cys
            20                  25                  30

Glu Ser Gln Ser His Lys Phe Lys Gly Pro Cys Ala Ser Asp His Asn
        35                  40                  45

Cys Ala Ser Val Cys Gln Thr Glu Arg Phe Ser Gly Gly His Cys Arg
    50                  55                  60

Gly Phe Arg Arg Arg Cys Phe Cys Thr Thr His Cys
```

65               70              75

<210> SEQ ID NO 67
<211> LENGTH: 76
<212> TYPE: PRT
<213> ORGANISM: Medicago truncatula

<400> SEQUENCE: 67

Met Ala Arg Ser Val Pro Leu Val Ser Thr Ile Phe Val Phe Leu Leu
1               5                   10                  15

Leu Leu Val Ala Thr Gly Pro Ser Met Val Ala Glu Ala Arg Thr Cys
            20                  25                  30

Glu Ser Gln Ser His Lys Phe Lys Gly Pro Cys Ala Ser Asp His Asn
        35                  40                  45

Cys Ala Ser Val Cys Gln Thr Glu Arg Phe Ser Gly Gly His Cys Arg
    50                  55                  60

Gly Phe Arg Arg Arg Cys Phe Cys Thr Thr His Cys
65                  70              75

<210> SEQ ID NO 68
<211> LENGTH: 76
<212> TYPE: PRT
<213> ORGANISM: Medicago truncatula

<400> SEQUENCE: 68

Met Ala Arg Ser Val Pro Leu Val Ser Thr Ile Phe Val Phe Leu Leu
1               5                   10                  15

Leu Leu Val Ala Thr Gly Pro Ser Met Val Ala Glu Ala Arg Thr Cys
            20                  25                  30

Glu Ser Gln Ser His Lys Phe Lys Gly Pro Cys Ala Ser Asp His Asn
        35                  40                  45

Cys Ala Ser Val Cys Gln Thr Glu Arg Phe Ser Gly Gly His Cys Arg
    50                  55                  60

Gly Phe Arg Arg Arg Cys Phe Cys Thr Thr His Cys
65                  70              75

<210> SEQ ID NO 69
<211> LENGTH: 76
<212> TYPE: PRT
<213> ORGANISM: Medicago truncatula

<400> SEQUENCE: 69

Met Ala Arg Ser Val Pro Leu Val Ser Thr Ile Phe Val Phe Leu Leu
1               5                   10                  15

Leu Leu Val Ala Thr Gly Pro Ser Met Val Ala Glu Ala Arg Thr Cys
            20                  25                  30

Glu Ser Gln Ser His Lys Phe Lys Gly Pro Cys Ala Ser Asp His Asn
        35                  40                  45

Cys Ala Ser Val Cys Gln Thr Glu Arg Phe Ser Gly Gly His Cys Arg
    50                  55                  60

Gly Phe Arg Arg Arg Cys Phe Cys Thr Thr His Cys
65                  70              75

<210> SEQ ID NO 70
<211> LENGTH: 76
<212> TYPE: PRT
<213> ORGANISM: Medicago truncatula

<400> SEQUENCE: 70

```
Met Ala Arg Ser Val Pro Leu Val Ser Thr Ile Phe Val Phe Leu Leu
1               5                   10                  15

Leu Leu Val Ala Thr Gly Pro Ser Met Val Ala Glu Ala Arg Thr Cys
            20                  25                  30

Glu Ser Gln Ser His Lys Phe Lys Gly Pro Cys Ala Ser Asp His Asn
        35                  40                  45

Cys Ala Ser Val Cys Gln Thr Glu Arg Phe Ser Gly Gly His Cys Arg
    50                  55                  60

Gly Phe Arg Arg Arg Cys Phe Cys Thr Thr His Cys
65                  70                  75

<210> SEQ ID NO 71
<211> LENGTH: 47
<212> TYPE: PRT
<213> ORGANISM: Medicago truncatula

<400> SEQUENCE: 71

Arg Thr Cys Glu Ser Gln Ser His Lys Phe Lys Gly Pro Cys Ala Ser
1               5                   10                  15

Asp His Asn Cys Ala Ser Val Cys Gln Thr Glu Arg Phe Ser Gly Gly
            20                  25                  30

His Cys Arg Gly Phe Arg Arg Arg Cys Phe Cys Thr Thr His Cys
        35                  40                  45

<210> SEQ ID NO 72
<211> LENGTH: 239
<212> TYPE: DNA
<213> ORGANISM: Artificial Sequence
<220> FEATURE:
<223> OTHER INFORMATION: synthetic MtDef4.1(H33R) DNA sequence that
      encodes a MtDef4(H33R) polypeptide

<400> SEQUENCE: 72
ccatggctag gtccgtgcca ctcgtgtcca ccatcttcgt gttcctcctc ctcctcgtgg     60
ccaccggccc aagcatggtc gccgaggcca ggacctgcga gtcccaatcc cacaagttca    120
agggcccatg cgccagcgac acaactgcg cctccgtgtg ccaaaccgag cgcttctccg     180
gcggcaggtg caggggcttc cgcaggaggt gcttctgcac cacccactgc taatctaga    239

<210> SEQ ID NO 73
<211> LENGTH: 1727
<212> TYPE: DNA
<213> ORGANISM: Artificial Sequence
<220> FEATURE:
<223> OTHER INFORMATION: DNA construct for expression of mature MtDef4
      protein in yeast

<400> SEQUENCE: 73
ctgaaaaata acagttatta ttcgagatct aacatccaaa gacgaaaggt tgaatgaaac     60 cttttttgcca tccgacatcc acaggtccat tctcacacat aagtgccaaa cgcaacagga   120
ggggatacac tagcagcaga ccgttgcaaa cgcaggacct ccactcctct tctcctcaac   180
acccactttt gccatcgaaa aaccagccca gttattgggc ttgattggag ctcgctcatt   240
ccaattcctt ctattaggct actaacacca tgactttatt agcctgtcta tcctggcccc   300
cctggcgagg ttcatgtttg tttatttccg aatgcaacaa gctccgcatt acacccgaac   360
atcactccag atgagggctt tctgagtgtg gggtcaaata gtttcatgtt ccccaaatgg   420
cccaaaactg acagtttaaa cgctgtcttg gaacctaata tgacaaaagc gtgatctcat   480
ccaagatgaa ctaagtttgg ttcgttgaaa tgctaacggc cagttggtca aaagaaact   540
```

```
tccaaaagtc gccataccgt ttgtcttgtt tggtattgat tgacgaatgc tcaaaaataa    600
tctcattaat gcttagcgca gtctctctat cgcttctgaa ccccggtgca cctgtgccga    660
aacgcaaatg gggaaacacc cgcttttggg atgattatgc attgtctcca cattgtatgc    720
ttccaagatt ctggtgggaa tactgctgat agcctaacgt tcatgatcaa aatttaactg    780
ttctaacccc tacttgacag caatatataa acagaaggaa gctgccctgt cttaaacctt    840 ttttttatc atcattatta gcttactttc ataattgcga ctggttccaa ttgacaagct      900
tttgatttta acgacttta acgacaactt gagaagatca aaaacaact aattattcga       960 aggatccaaa cgatgagatt ccttcaatt tttactgcag ttttattcgc agcatcctcc     1020
gcattagctg ctccagtcaa cactacaaca gaagatgaaa cggcacaaat tccggctgaa    1080
gctgtcatcg gttactcaga tttagaaggg gatttcgatg ttgctgtttt gccattttcc    1140
aacagcacaa ataacgggtt attgtttata aatactacta ttgccagcat tgctgctaaa    1200
gaagaagggg tatctcgaga aagaagaac ttgtgagtca caaagtcaca aattcaaagg     1260
gccatgtgct agtgatcaca actgtgcttc tgtgtgccaa acagaacgtt tctctggagg    1320
acgctgccgt ggattccgtc gtagatgctt ttgcactaca cattgttaag aattccctag    1380
ggcggccgcg aattaattcg ccttagacat gactgttcct cagttcaagt tgggcactta    1440
cgagaagacc ggtcttgcta gattctaatc aagaggatgt cagaatgcca tttgcctgag    1500
agatgcaggc ttcattttg atactttttt atttgtaacc tatatagtat aggatttttt    1560
ttgtcatttt gtttcttctc gtacgagctt gctcctgatc agcctatctc gcagctgatg    1620
aatatcttgt ggtaggggtt tgggaaaatc attcgagttt gatgttttc ttggtatttc    1680 ccactcctct tcagagtaca gaagattaag tgagaagttc gtttgtg               1727
```

<210> SEQ ID NO 74
<211> LENGTH: 2596
<212> TYPE: DNA
<213> ORGANISM: Artificial Sequence
<220> FEATURE:
<223> OTHER INFORMATION: DNA for expression of MtDef4 protein in plants
<220> FEATURE:
<221> NAME/KEY: misc_feature
<222> LOCATION: (598)..(598)
<223> OTHER INFORMATION: n is a, c, g, or t
<220> FEATURE:
<221> NAME/KEY: misc_feature
<222> LOCATION: (781)..(782)
<223> OTHER INFORMATION: n is a, c, g, or t
<220> FEATURE:
<221> NAME/KEY: misc_feature
<222> LOCATION: (1969)..(1970)
<223> OTHER INFORMATION: n is a, c, g, or t

<400> SEQUENCE: 74

```
agcttgcatg cctgcagtgc agcgtgaccc ggtcgtgccc ctctctagag ataatgagca    60
ttgcatgtct aagttataaa aaattaccac atatttttt tgtcacactt gtttgaagtg    120
cagtttatct atctttatac atatatttaa actttactct acgaataata taatctatag   180
tactacaata atatcagtgt tttagagaat catataaatg aacagttaga catggtctaa   240
aggacaattg agtattttga caacaggact ctacagtttt atctttttag tgtgcatgtg   300 ttctccttt tttttgcaaa tagcttcacc tatataatac ttcatccatt ttattagtac    360
atccatttag ggtttagggt taatggtttt tatagactaa ttttttagt acatctattt    420 tattctattt tagcctctaa attaagaaaa ctaaaactct attttagttt ttttatttaa   480
```

```
taatttagat ataaaataga ataaaataaa gtgactaaaa attaaacaaa taccctttaa    540
gaaattaaaa aaactaaggg aacattttc ttgtttcgag tagataatgc cagcctgnta     600
aacgccgtcg acgagtctaa cggacaccaa ccagcgaacc agcagcgtcg cgtcgggcca    660
gcgaagcaga cggcacggca tctctgtcgc tgcctctgga cccctctcga gagttccgct    720
ccaccgttgg acttgctccg ctgtcggcat ccagaaattg cgtggcggag cggcagacgt    780
nngccggcac ggcaggcggc ctcctcctcc tctcacggca ccggcagcta cggggggattc   840 cttcccacc gctccttcgc tttcccttcc tcgcccgccg taataaatag cacccccctc     900
cacaccctct ttccccaacc tcgtgttgtt cggagcgcac acacacacaa ccagatctcc    960
cccaaatcca cccgtcggca cctccgcttc aaggtacgcc gctcgtcctc ccccccccc   1020 cctctctacc ttctctagat cggcgttccg gtccatggtt agggcccggt agttctactt   1080
ctgttcatgt ttgtgttaga tccgtgtttg tgttagatcc gtgctgctag cgttcgtaca   1140
cggatgcgac ctgtacgtca gacacgttct gattgctaac ttgccagtgt ttctctttgg   1200
ggaatcctgg gatggctcta gccgttccgc agacgggatc gatttcatga ttttttttgt   1260
ttcgttgcat agggtttggt ttgccctttt cctttatttc aatatatgcc gtgcacttgt   1320
ttgtcgggtc atcttttcat gctttttttt gtcttggttg tgatgatgtg gtctggttgg   1380
gcggtcgttc tagatcggag tagaattaat tctgtttcaa actacctggt ggatttatta   1440
attttggatc tgtatgtgtg tgccatacat attcatagtt acgaattgaa gatgatggat   1500
ggaaatatcg atctaggata ggtatacatg ttgatgcggg ttttactgat gcatatacag   1560
agatgctttt tgttcgcttg gttgtgatga tgtggtgtgg ttgggcggtc gttcattcgt   1620
tctagatcgg agtagaatac tgtttcaaac tacctggtgt atttattaat tttggaactg   1680
tatgtgtgtg tcatacatct tcatagttac gagtttaaga tggatggaaa tatcgatcta   1740
ggataggtat acatgttgat gtgggtttta ctgatgcata tacatgatgg catatgcagc   1800
atctattcat atgctctaac cttgagtacc tatctattat aataaacaag tatgttttat   1860
aattattttg atcttgatat acttggatga tggcatatgc agcagctata tgtggatttt   1920
tttagccctg ccttcatacg ctatttattt gcttggtact gtttctttnn tcgatgctca   1980
ccctgttgtt tggtgttact tctgcaggtc gagaattctc aacacaacat atacaaaaca   2040
aacgaatctc aagcaatcaa gcattctact tctattgcag caatttaaat catttctttt   2100
aaagcaaaag caattttctg aaaattttca ccatttacga acgatagcca tggctaggtc   2160
cgtgccactc gtgtccacca tcttcgtgtt cctcctcctc ctcgtggcca ccggcccaag   2220
catggtcgcc gaggccagga cctgcgagtc ccaatcccac aagttcaagg gcccatgcgc   2280
cagcgaccac aactgcgcct ccgtgtgcca aaccgagcgc ttctccggcg gcaggtgcag   2340
gggcttccgc aggaggtgct tctgcaccac ccactgctaa tctagagtcc gcaaaaatca   2400
ccagtctctc tctacaaatc tatctctctc tattttctc cagaataatg tgtgagtagt    2460
tcccagataa gggaattagg gttcttatag ggtttcgctc atgtgttgag catataagaa   2520 accttagta tgtatttgta tttgtaaaat acttctatca ataaaatttc taattcctaa    2580
aaccaaaatc cagtga                                                  2596
```

<210> SEQ ID NO 75
<211> LENGTH: 2175
<212> TYPE: DNA
<213> ORGANISM: Artificial Sequence
<220> FEATURE:
<223> OTHER INFORMATION: DNA for expression of MtDef4 protein in plants

```
<220> FEATURE:
<221> NAME/KEY: misc_feature
<222> LOCATION: (1110)..(1110)
<223> OTHER INFORMATION: n is a, c, g, or t

<400> SEQUENCE: 75
caaaatattt agcagcattc cagattgggt tcaatcaaca aggtacgagc catatcactt      60
tattcaaatt ggtatcgcca aaaccaagaa ggaactccca tcctcaaagg tttgtaagga     120
agaattctca gtccaaagcc tcaacaaggt cagggtacag agtctccaaa ccattagcca     180
aaagctacag gagatcaatg aagaatcttc aatcaaagta aactactgtt ccagcacatg     240
catcatggtc agtaagtttc agaaaaagac atccaccgaa gacttaaagt tagtgggcat     300
ctttgaaagt aatcttgtca acatcgagca gctggcttgt ggggaccaga caaaaaagga     360
atggtgcaga attgttaggc gcacctacca aaagcatctt tgcctttatt gcaaagataa     420
agcagattcc tctagtacaa gtggggaaca aaataacgtg gaaaagagct gtcctgacag     480
cccactcact aatgcgtatg acgaacgcag tgacgaccac aaaagaattc cctctatata     540
agaaggcatt cattcccatt tgaaggatca tcagatactg aaccaatatt gataattccg     600
atattctcag agagcttttc attcaaaggt atggagtttt gaagggcttt actcttaaca     660
tttgtttttc tttgtaaatt gttaatggtg gtttctgtgg gggaagaatc ttttgccagg     720
tccttttggg tttcgcatgt ttatttgggt tattttctc gactatggct gacattacta     780
gggctttcgt gctttcatct gtgttttctt cccttaatag gtctgtctct ctggaatatt     840
taattttcgt atgtaagtta tgagtagtcg ctgtttgtaa taggctcttg tctgtaaagg     900
tttcagcagg tgtttgcgtt ttattgcgtc atgtgtttca gaaggccttt gcagattatt     960
gcgttgtact ttaatatttt gtctccaacc ttgttatagt ttccctcctt tgatctcaca    1020
ggaacccttt cttctttgag cattttcttg tggcgttctg tagtaatatt ttaattttgg    1080
gcccgggttc tgagggtagg tgattattcn cagtgatgtg ctttccctat aaggtcctct    1140
atgtgtaagc tgttagggtt tgtgcgttac tattgacatg tcacatgtca catattttct    1200
tcctcttatc cttcgaactg atggttcttt ttctaattcg tggattgctg gtgccatatt    1260
ttatttctat tgcaactgta ttttaggtg tctctttctt tttgatttct tgttaatatt    1320
tgtgttcagg ttgtaactat gggttgctag ggtgtctgcc ctcttctttt gtgcttcttt    1380
cgcagaatct gtccgttggt ctgtatttgg gtgatgaatt atttattcct tgaagtatct    1440
gtctaattag cttgtgatga tgtgcaggta tattcgttag tcatatttca aggatccaaa    1500
accatggctc gttcagttcc tttggtttcc accatctttg tcttccttct gcttcttgtg    1560
gccactggtg agtagtgttt ctttatcctt aatctaacac catcatgtct ttgtttactc    1620
aattaaccag tttatatctt gacaaaatct caattaacat agtcatagta taatccataa    1680
tatttctta ttttgatata gaattgttgt taattgattt tgtgatatat ggtatagggc    1740
caagtatggt ggcagaagca agaacttgtg agtcacaaag tcacaaattc aaagggccat    1800
gtgctagtga tcacaactgt gcttctgtgt gccaaacaga acgtttctct ggaggacact    1860
gccgtggatt ccgtcgtaga tgcttttgca ctacacattg ttaagagctc cgaatttccc    1920
cgatcgttca aacatttggc aataaagttt cttaagattg aatcctgttg ccggtcttgc    1980
gatgattatc atataaattc tgttgaatta cgttaagcat gtaataatta acatgtaatg    2040
catgacgtta tttatgagat gggttttat gattagagtc ccgcaattat acatttaata    2100
cgcgatagaa aacaaaatat agcgcgcaaa ctaggataaa ttatcgcgcg cggtgtcatc    2160
```

<210> SEQ ID NO 76
<211> LENGTH: 2220
<212> TYPE: DNA
<213> ORGANISM: Artificial Sequence
<220> FEATURE:
<223> OTHER INFORMATION: DNA for expression of MtDef4 protein in plants
<220> FEATURE:
<221> NAME/KEY: misc_feature
<222> LOCATION: (1110)..(1110)
<223> OTHER INFORMATION: n is a, c, g, or t

<400> SEQUENCE: 76

```
caaaatattt agcagcattc cagattgggt tcaatcaaca aggtacgagc catatcactt      60
tattcaaatt ggtatcgcca aaaccaagaa ggaactccca tcctcaaagg tttgtaagga     120
agaattctca gtccaaagcc tcaacaaggt cagggtacag agtctccaaa ccattagcca     180
aaagctacag gagatcaatg aagaatcttc aatcaaagta aactactgtt ccagcacatg     240
catcatggtc agtaagtttc agaaaaagac atccaccgaa gacttaaagt tagtgggcat     300 cttttgaaagt aatcttgtca acatcgagca gctggcttgt ggggaccaga caaaaaagga     360
atggtgcaga attgttaggc gcacctacca aaagcatctt tgcctttatt gcaaagataa     420
agcagattcc tctagtacaa gtggggaaca aaataacgtg gaaaagagct gtcctgacag     480
cccactcact aatgcgtatg acgaacgcag tgacgaccac aaaagaattc cctctatata     540
agaaggcatt cattcccatt tgaaggatca tcagatactg aaccaatatt gataattccg     600
atattctcag agagcttttc attcaaaggt atggagtttt gaagggcttt actcttaaca     660
tttgtttttc tttgtaaatt gttaatggtg gtttctgtgg gggaagaatc ttttgccagg     720
tccttttggg tttcgcatgt ttatttgggt tattttctc gactatggct gacattacta     780
gggctttcgt gctttcatct gtgttttctt cccttaatag gtctgtctct ctggaatatt     840
taattttcgt atgtaagtta tgagtagtcg ctgtttgtaa taggctcttg tctgtaaagg     900
tttcagcagg tgtttgcgtt ttattgcgtc atgtgtttca gaaggccttt gcagattatt     960
gcgttgtact ttaatatttt gtctccaacc ttgttatagt ttccctcctt tgatctcaca    1020
ggaacccttt cttctttgag cattttcttg tggcgttctg tagtaatatt ttaattttgg    1080
gcccgggttc tgagggtagg tgattattcn cagtgatgtg ctttccctat aaggtcctct    1140
atgtgtaagc tgttagggtt tgtgcgttac tattgacatg tcacatgtca catattttct    1200
tcctcttatc cttcgaactg atggttcttt ttctaattcg tggattgctg gtgccatatt    1260
ttatttctat tgcaactgta ttttagggtg tctctttctt tttgatttct tgttaatatt    1320
tgtgttcagg ttgtaactat gggttgctag ggtgtctgcc ctcttctttt gtgcttcttt    1380
cgcagaatct gtccgttggt ctgtatttgg gtgatgaatt atttattcct tgaagtatct    1440
gtctaattag cttgtgatga tgtgcaggta tattcgttag tcatatttca aggatccaaa    1500
accatggctc gttcagttcc tttggtttcc accatctttg tcttccttct gcttcttgtg    1560
gccactggtg agtagtgttt ctttatcctt aatctaacac catcatgtct tgtttactc    1620 aattaaccag tttatatctt gacaaaatct caattaacat agtcatagta taatccataa    1680 tatttctttta ttttgatata gaattgttgt taattgattt tgtgatatat ggtataggc    1740 caagtatggt ggcagaagca agaacttgtg agtcacaaag tcacaaattc aaagggccat    1800
gtgctagtga tcacaactgt gcttctgtgt gccaaacaga acgttctct ggaggacact    1860 gccgtggatt ccgtcgtaga tgcttttgca ctacacattg tgtcttcgcc gaggccatcg    1920
```

```
ccgccaactc cactcttgtc gcagaataag agctccgaat ttccccgatc gttcaaacat    1980
ttggcaataa agtttcttaa gattgaatcc tgttgccggt cttgcgatga ttatcatata    2040
atttctgttg aattacgtta agcatgtaat aattaacatg taatgcatga cgttatttat    2100
gagatgggtt tttatgatta gagtcccgca attatacatt taatacgcga tagaaaacaa    2160
aatatagcgc gcaaactagg ataaattatc gcgcgcggtg tcatctatgt tactagatcg    2220
```

<210> SEQ ID NO 77
<211> LENGTH: 76
<212> TYPE: PRT
<213> ORGANISM: Medicago truncatula

<400> SEQUENCE: 77

Met Ala Arg Ser Val Phe Leu Val Ser Thr Ile Phe Val Phe Leu Leu
1               5                   10                  15

Val Leu Val Ala Thr Gly Pro Ser Met Val Ala Glu Ala Arg Thr Cys
            20                  25                  30

Glu Ser Gln Ser His Lys Phe Lys Gly Pro Cys Ala Ser Asp His Asn
        35                  40                  45

Cys Ala Ser Val Cys Gln Thr Glu Arg Phe Ser Gly Gly His Cys Arg
    50                  55                  60

Gly Phe Arg Arg Arg Cys Phe Cys Thr Thr His Cys
65                  70                  75

<210> SEQ ID NO 78
<211> LENGTH: 76
<212> TYPE: PRT
<213> ORGANISM: Medicago truncatula

<400> SEQUENCE: 78

Met Ala Arg Ser Val Ser Leu Val Phe Thr Ile Phe Val Phe Leu Leu
1               5                   10                  15

Leu Val Val Ala Thr Gly Pro Ser Met Val Ala Glu Ala Arg Thr Cys
            20                  25                  30

Glu Ser Gln Ser His Lys Phe Lys Gly Pro Cys Ala Ser Asp His Asn
        35                  40                  45

Cys Ala Ser Val Cys Gln Thr Glu Arg Phe Ser Gly Gly His Cys Arg
    50                  55                  60

Gly Phe Arg Arg Arg Cys Phe Cys Thr Thr His Cys
65                  70                  75

<210> SEQ ID NO 79
<211> LENGTH: 76
<212> TYPE: PRT
<213> ORGANISM: Medicago truncatula

<400> SEQUENCE: 79

Met Gly Ser Phe Ser Ser Phe Gly Phe Thr Ile Phe Val Phe Leu Leu
1               5                   10                  15

Leu Leu Val Ala Thr Gly Pro Ser Met Val Ala Glu Ala Arg Thr Cys
            20                  25                  30

Glu Ser Gln Ser His Lys Phe Lys Gly Pro Cys Ala Ser Asp His Asn
        35                  40                  45

Cys Ala Ser Val Cys Gln Thr Glu Arg Phe Ser Gly Gly His Cys Arg
    50                  55                  60

Gly Phe Arg Arg Arg Cys Phe Cys Thr Thr His Cys
65                  70                  75

<210> SEQ ID NO 80
<211> LENGTH: 76
<212> TYPE: PRT
<213> ORGANISM: Medicago truncatula

<400> SEQUENCE: 80

Met Ala Arg Ser Val Pro Leu Val Ser Thr Ile Phe Val Phe Leu Leu
1               5                   10                  15

Leu Leu Val Ala Thr Gly Pro Ser Met Val Ala Glu Ala Arg Thr Cys
            20                  25                  30

Glu Ser Gln Ser His Lys Phe Lys Gly Pro Cys Ala Ser Asp His Asn
        35                  40                  45

Cys Ala Ser Val Cys Gln Thr Glu Arg Phe Phe Gly Gly His Cys Arg
    50                  55                  60

Gly Phe Arg Arg Arg Cys Phe Cys Thr Thr His Cys
65                  70                  75

<210> SEQ ID NO 81
<211> LENGTH: 76
<212> TYPE: PRT
<213> ORGANISM: Medicago truncatula

<400> SEQUENCE: 81

Met Ala Arg Ser Val Pro Leu Val Ser Thr Ile Phe Val Phe Leu Leu
1               5                   10                  15

Leu Leu Val Ala Thr Gly Pro Ser Met Val Ala Glu Ala Arg Thr Cys
            20                  25                  30

Glu Ser Gln Ser His Lys Phe Lys Gly Pro Cys Ala Ser Asp His Asn
        35                  40                  45

Cys Ala Ser Val Cys Gln Thr Glu Arg Phe Ser Gly Gly His Cys Arg
    50                  55                  60

Gly Phe Arg Arg Arg Cys Phe Cys Thr Thr His Cys
65                  70                  75

<210> SEQ ID NO 82
<211> LENGTH: 76
<212> TYPE: PRT
<213> ORGANISM: Medicago truncatula

<400> SEQUENCE: 82

Met Ala Arg Ser Val Pro Leu Val Ser Thr Ile Phe Val Phe Leu Leu
1               5                   10                  15

Leu Leu Val Ala Thr Gly Pro Ser Met Val Ala Glu Ala Arg Thr Cys
            20                  25                  30

Glu Ser Gln Ser His Lys Phe Lys Gly Pro Cys Ala Ser Asp His Asn
        35                  40                  45

Cys Ala Ser Val Cys Gln Thr Glu Arg Phe Ser Gly Gly His Cys Arg
    50                  55                  60

Gly Phe Arg Arg Arg Cys Phe Cys Thr Thr His Cys
65                  70                  75

<210> SEQ ID NO 83
<211> LENGTH: 76
<212> TYPE: PRT
<213> ORGANISM: Medicago truncatula

<400> SEQUENCE: 83

Met Ala Arg Ser Val Pro Leu Val Ser Thr Ile Phe Val Phe Leu Leu

```
                1               5                  10                 15
Leu Leu Val Ala Thr Gly Pro Ser Met Val Ala Glu Ala Arg Thr Cys
            20                  25                 30

Glu Ser Gln Ser His Lys Phe Lys Gly Pro Cys Ala Ser Asp His Asn
            35                  40                 45

Cys Ala Ser Val Cys Gln Thr Glu Arg Phe Ser Gly Gly His Cys Arg
            50                  55                 60

Gly Phe Arg Arg Arg Cys Phe Cys Thr Thr His Cys
65                  70                 75

<210> SEQ ID NO 84
<211> LENGTH: 76
<212> TYPE: PRT
<213> ORGANISM: Medicago truncatula

<400> SEQUENCE: 84

Met Ala Arg Ser Val Pro Leu Val Ser Thr Ile Phe Val Phe Leu Leu
1               5                  10                 15

Leu Leu Val Ala Thr Gly Pro Ser Met Val Ala Glu Ala Arg Thr Cys
            20                  25                 30

Glu Ser Gln Ser His Lys Phe Lys Gly Pro Cys Ala Ser Asp His Asn
            35                  40                 45

Cys Ala Ser Val Cys Gln Thr Glu Arg Phe Ser Gly Gly His Cys Arg
            50                  55                 60

Gly Phe Arg Arg Arg Cys Phe Cys Thr Thr His Cys
65                  70                 75

<210> SEQ ID NO 85
<211> LENGTH: 76
<212> TYPE: PRT
<213> ORGANISM: Medicago truncatula

<400> SEQUENCE: 85

Met Ala Arg Ser Val Pro Leu Val Ser Thr Ile Phe Val Phe Leu Leu
1               5                  10                 15

Leu Leu Val Ala Thr Gly Pro Ser Met Val Ala Glu Ala Arg Thr Cys
            20                  25                 30

Glu Ser Gln Ser His Lys Phe Lys Gly Pro Cys Ala Ser Asp His Asn
            35                  40                 45

Cys Ala Ser Val Cys Gln Thr Glu Arg Phe Ser Gly Gly His Cys Arg
            50                  55                 60

Gly Phe Arg Arg Arg Cys Phe Cys Thr Thr His Cys
65                  70                 75

<210> SEQ ID NO 86
<211> LENGTH: 76
<212> TYPE: PRT
<213> ORGANISM: Medicago truncatula

<400> SEQUENCE: 86

Met Ala Arg Ser Val Pro Leu Val Ser Thr Ile Phe Val Phe Leu Leu
1               5                  10                 15

Leu Leu Val Ala Thr Gly Pro Ser Met Val Ala Glu Ala Arg Thr Cys
            20                  25                 30

Glu Ser Gln Ser His Lys Phe Lys Gly Pro Cys Ala Ser Asp His Asn
            35                  40                 45

Cys Ala Ser Val Cys Gln Thr Glu Arg Phe Ser Gly Gly His Cys Arg
            50                  55                 60
```

```
Gly Phe Arg Arg Arg Cys Phe Cys Thr Thr His Cys
65                  70                  75

<210> SEQ ID NO 87
<211> LENGTH: 76
<212> TYPE: PRT
<213> ORGANISM: Medicago truncatula

<400> SEQUENCE: 87

Met Ala Arg Ser Val Pro Leu Val Ser Thr Ile Phe Val Phe Leu Leu
1               5                   10                  15

Leu Leu Val Ala Thr Gly Pro Ser Met Val Gly Glu Ala Arg Thr Cys
            20                  25                  30

Glu Ser Gln Ser His Lys Phe Lys Gly Pro Cys Ala Ser Asp His Asn
        35                  40                  45

Cys Ala Ser Val Cys Gln Thr Glu Arg Phe Ser Gly Gly His Cys Arg
    50                  55                  60

Gly Phe Arg Arg Arg Cys Phe Cys Thr Thr His Cys
65                  70                  75

<210> SEQ ID NO 88
<211> LENGTH: 76
<212> TYPE: PRT
<213> ORGANISM: Medicago truncatula

<400> SEQUENCE: 88

Met Ala Arg Ser Val Pro Leu Val Ser Thr Ile Phe Val Phe Leu Leu
1               5                   10                  15

Leu Leu Val Ala Thr Gly Pro Ser Met Val Ala Glu Ala Arg Thr Cys
            20                  25                  30

Glu Ser Gln Ser His Lys Phe Lys Gly Pro Cys Ala Ser Asp His Asn
        35                  40                  45

Cys Ala Ser Val Cys Gln Thr Glu Arg Phe Ser Gly Gly His Cys Arg
    50                  55                  60

Gly Phe Arg Arg Arg Cys Phe Cys Thr Thr His Cys
65                  70                  75

<210> SEQ ID NO 89
<211> LENGTH: 76
<212> TYPE: PRT
<213> ORGANISM: Medicago truncatula

<400> SEQUENCE: 89

Met Ala Arg Ser Val Pro Leu Val Ser Thr Ile Phe Val Phe Leu Leu
1               5                   10                  15

Leu Leu Val Ala Thr Gly Pro Ser Met Val Ala Glu Ala Arg Thr Cys
            20                  25                  30

Glu Ser Gln Ser His Lys Phe Lys Gly Pro Cys Ala Ser Asp His Asn
        35                  40                  45

Cys Ala Ser Val Cys Gln Thr Glu Arg Phe Ser Gly Gly His Cys Arg
    50                  55                  60

Gly Phe Arg Arg Arg Cys Phe Cys Thr Thr His Cys
65                  70                  75

<210> SEQ ID NO 90
<211> LENGTH: 76
<212> TYPE: PRT
<213> ORGANISM: Medicago truncatula
```

```
<400> SEQUENCE: 90

Met Ala Arg Ser Val Pro Leu Val Ser Thr Ile Phe Val Phe Leu Leu
1               5                   10                  15

Leu Leu Val Ala Thr Gly Pro Ser Met Val Ala Glu Ala Arg Thr Cys
            20                  25                  30

Glu Ser Gln Ser His Lys Phe Lys Gly Pro Cys Ala Ser Asp His Asn
        35                  40                  45

Cys Ala Ser Val Cys Gln Thr Glu Arg Phe Ser Gly Gly His Cys Arg
    50                  55                  60

Gly Phe Arg Arg Arg Cys Phe Cys Thr Thr His Cys
65                  70                  75

<210> SEQ ID NO 91
<211> LENGTH: 76
<212> TYPE: PRT
<213> ORGANISM: Medicago truncatula

<400> SEQUENCE: 91

Met Ala Arg Ser Val Pro Leu Val Ser Thr Ile Phe Val Phe Leu Leu
1               5                   10                  15

Leu Leu Val Ala Thr Gly Pro Ser Met Val Ala Glu Ala Arg Thr Cys
            20                  25                  30

Glu Ser Gln Ser His Lys Phe Lys Gly Pro Cys Ala Ser Asp His Asn
        35                  40                  45

Cys Ala Ser Val Cys Gln Thr Glu Arg Phe Ser Gly Gly His Cys Arg
    50                  55                  60

Gly Phe Arg Arg Arg Cys Phe Cys Thr Thr His Cys
65                  70                  75

<210> SEQ ID NO 92
<211> LENGTH: 76
<212> TYPE: PRT
<213> ORGANISM: Medicago truncatula

<400> SEQUENCE: 92

Met Ala Arg Ser Val Pro Leu Val Ser Thr Ile Phe Val Phe Leu Leu
1               5                   10                  15

Leu Leu Val Ala Thr Gly Pro Ser Met Val Ala Glu Ala Arg Thr Cys
            20                  25                  30

Glu Ser Gln Ser His Lys Phe Lys Gly Pro Cys Ala Ser Asp His Asn
        35                  40                  45

Cys Ala Ser Val Cys Gln Thr Glu Arg Phe Ser Gly Gly His Cys Arg
    50                  55                  60

Gly Phe Arg Arg Arg Cys Phe Cys Thr Thr His Cys
65                  70                  75

<210> SEQ ID NO 93
<211> LENGTH: 76
<212> TYPE: PRT
<213> ORGANISM: Medicago truncatula

<400> SEQUENCE: 93

Met Ala Arg Ser Val Pro Leu Val Ser Thr Ile Phe Val Phe Leu Leu
1               5                   10                  15

Leu Leu Val Ala Thr Gly Pro Ser Met Val Ala Glu Ala Arg Thr Cys
            20                  25                  30

Glu Ser Gln Ser His Lys Phe Lys Gly Pro Cys Ala Ser Asp His Asn
        35                  40                  45
```

```
Cys Ala Ser Val Cys Gln Thr Glu Arg Phe Ser Gly Gly His Cys Arg
        50                  55                  60

Gly Phe Arg Arg Arg Cys Phe Cys Thr Thr His Cys
65                  70                  75

<210> SEQ ID NO 94
<211> LENGTH: 76
<212> TYPE: PRT
<213> ORGANISM: Medicago truncatula

<400> SEQUENCE: 94

Met Ala Arg Ser Val Pro Leu Val Ser Thr Ile Phe Val Phe Leu Leu
1               5                   10                  15

Leu Leu Val Ala Thr Gly Pro Ser Met Val Ala Glu Ala Arg Thr Cys
            20                  25                  30

Glu Ser Gln Ser His Lys Phe Lys Gly Pro Cys Ala Ser Asp His Asn
        35                  40                  45

Cys Ala Ser Val Cys Gln Thr Glu Arg Phe Ser Gly Gly His Cys Arg
    50                  55                  60

Gly Phe Arg Arg Arg Cys Phe Cys Thr Thr His Cys
65                  70                  75

<210> SEQ ID NO 95
<211> LENGTH: 76
<212> TYPE: PRT
<213> ORGANISM: Medicago truncatula

<400> SEQUENCE: 95

Met Ala Arg Ser Val Pro Leu Val Ser Thr Ile Phe Val Phe Leu Leu
1               5                   10                  15

Leu Leu Val Ala Thr Gly Pro Ser Met Val Ala Glu Ala Arg Thr Cys
            20                  25                  30

Glu Ser Gln Ser His Lys Phe Lys Gly Pro Cys Ala Ser Asp His Asn
        35                  40                  45

Cys Ala Ser Val Cys Gln Thr Glu Arg Phe Ser Gly Gly His Cys Arg
    50                  55                  60

Gly Phe Arg Arg Arg Cys Phe Cys Thr Thr His Cys
65                  70                  75

<210> SEQ ID NO 96
<211> LENGTH: 76
<212> TYPE: PRT
<213> ORGANISM: Medicago truncatula

<400> SEQUENCE: 96

Met Ala Arg Ser Val Pro Leu Val Ser Thr Ile Phe Val Phe Leu Leu
1               5                   10                  15

Leu Leu Val Ala Thr Gly Pro Ser Met Val Ala Glu Ala Arg Thr Cys
            20                  25                  30

Glu Ser Gln Ser His Lys Phe Lys Gly Pro Cys Ala Ser Asp His Asn
        35                  40                  45

Cys Ala Ser Val Cys Gln Thr Glu Arg Phe Ser Gly Gly His Cys Arg
    50                  55                  60

Gly Phe Arg Arg Arg Cys Phe Cys Thr Thr His Cys
65                  70                  75

<210> SEQ ID NO 97
<211> LENGTH: 76
```

<212> TYPE: PRT
<213> ORGANISM: Medicago truncatula

<400> SEQUENCE: 97

```
Met Ala Arg Ser Val Pro Leu Val Ser Thr Ile Phe Val Phe Leu Leu
1               5                   10                  15

Leu Leu Val Ala Thr Gly Pro Ser Met Val Ala Glu Ala Arg Thr Cys
            20                  25                  30

Glu Ser Gln Ser His Lys Phe Lys Gly Pro Cys Ala Ser Asp His Asn
        35                  40                  45

Cys Ala Ser Val Cys Gln Thr Glu Arg Phe Ser Gly Gly His Cys Arg
    50                  55                  60

Gly Phe Arg Arg Arg Cys Phe Cys Thr Thr His Cys
65                  70                  75
```

<210> SEQ ID NO 98
<211> LENGTH: 76
<212> TYPE: PRT
<213> ORGANISM: Medicago truncatula

<400> SEQUENCE: 98

```
Met Ala Arg Ser Val Pro Leu Val Ser Thr Ile Phe Val Phe Leu Leu
1               5                   10                  15

Leu Leu Val Ala Thr Gly Pro Ser Met Val Ala Glu Ala Arg Thr Cys
            20                  25                  30

Glu Ser Gln Ser His Lys Phe Lys Gly Pro Cys Ala Ser Asp His Asn
        35                  40                  45

Cys Ala Ser Val Cys Gln Thr Glu Arg Phe Ser Gly Gly His Cys Arg
    50                  55                  60

Gly Phe Arg Arg Arg Cys Phe Cys Thr Thr His Cys
65                  70                  75
```

<210> SEQ ID NO 99
<211> LENGTH: 76
<212> TYPE: PRT
<213> ORGANISM: Medicago truncatula

<400> SEQUENCE: 99

```
Met Ala Arg Ser Val Pro Leu Val Ser Thr Ile Phe Val Phe Leu Leu
1               5                   10                  15

Leu Leu Val Ala Thr Gly Pro Ser Met Val Ala Glu Ala Arg Thr Cys
            20                  25                  30

Glu Ser Gln Ser His Lys Phe Lys Gly Pro Cys Ala Ser Asp His Asn
        35                  40                  45

Cys Ala Ser Val Cys Gln Thr Glu Arg Phe Ser Gly Gly His Cys Arg
    50                  55                  60

Gly Phe Arg Arg Arg Cys Phe Cys Thr Thr His Cys
65                  70                  75
```

<210> SEQ ID NO 100
<211> LENGTH: 367
<212> TYPE: DNA
<213> ORGANISM: Medicago truncatula

<400> SEQUENCE: 100

```
tttttttctt acaagttatc atggctcgtt cagttccttt ggtttccacc atctttgtct     60
tccttctgct tcttgtggcc actgggccaa gtatggtggc agaagcaaga acttgtgagt    120
cacaaagtca caaattcaaa gggccatgtg ctagtgatca caactgtgct tctgtgtgcc    180
```

```
aaacagaacg tttctctgga ggacactgcc gtggattccg tcgtagatgc ttttgcacta      240
cacattgtta aatacatgtt taagaaatta atccctatat gctaagaaaa aaaagatgat      300
ggatccatca ccttttttcta cttgttcatg ttttggaata aagctagcta gctatccatt     360
ttattat                                                                367
```

<210> SEQ ID NO 101
<211> LENGTH: 480
<212> TYPE: DNA
<213> ORGANISM: Medicago truncatula

<400> SEQUENCE: 101

```
cttacaagtt atcatggctc gttcagtttt tttggtttcc accatctttg tcttccttct      60
ggttcttgtg ccactgggc caagtatggt ggcagaagca agaacttgtg agtcacaaag       120
tcacaaattc aaagggccat gtgctagtga tcacaactgt gcttctgtgt gccaaacaga      180
acgtttctct ggaggacact gccgtggatt ccgtcgtaga tgcttttgca ctacacattg      240
ttaaatacat gtttaagaaa ttaatcccta tatgctaaga aaaaaagat gatggatcca       300 tcaccttttt ctacttgttc atgttttgga ataaagctag ctagctatcc attttattat     360
gggtttcttt ctatctttgt ctttttttta atgtcttgtt atagatcttt cgatcgtacg      420
agtagaagtg aatgaaatga agaatatcat gtgtgttctc tcaaaacaaa aaaaaaaaa     480
```

<210> SEQ ID NO 102
<211> LENGTH: 420
<212> TYPE: DNA
<213> ORGANISM: Medicago truncatula

<400> SEQUENCE: 102

```
gttctctttt tttcttacaa gttatcatgg ctcgttcagt tcctttggtt tccaccatct      60 tgtcttcct tctgcttctt gtggccactg ggccaagtat ggtggcagaa gcaagaactt       120
gtgagtcaca agtcacaaa ttcaaagggc catgtgctag tgatcacaac tgtgcttctg      180
tgtgccaaac agaacgtttc tttggaggac actgccgtgg attccgtcgt agatgctttt     240
gcactacaca ttgttaaata catgtttaag aaattaatcc ctatatgcta agaaaaaaaa     300
gatgatggat ccatcccctt ttctacttg ttcatgtttt ggaataaagc tagctagcta      360 tccatttat tatgggtttc tttctaaaaa aaaaaaaaaa aaaaaaaaaa aaaaaaaaaa      420
```

<210> SEQ ID NO 103
<211> LENGTH: 509
<212> TYPE: DNA
<213> ORGANISM: Medicago truncatula

<400> SEQUENCE: 103

```
acaagttatc atggctcgtt cagtttcttt ggttttcacc atctttgtct tccttctgct     60
tgttgtggcc actgggccaa gtatggtggc agaagcaaga acttgtgagt cacaaagtca     120
caaattcaaa gggccatgtg ctagtgatca caactgtgct tctgtgtgcc aaacagaacg     180
tttctctgga ggacactgcc gtggattccg tcgtagatgc ttttgcacta cacattgtta     240
aatacatgtt taagaaatta atccctatat gctaagaaaa aaaagatgat ggatccatca     300 ccttttttcta cttgttcatg ttttggaata aagctagcta gctatccatt ttattatggg    360 tttcttttcta tctttgtctt tttttaatg tcttgttata gatctttcga tcgtacgagt     420
agaagtgaat gaaatgaaga atatcatgtg tgttctctca acaatctttt gatcatatca     480
```

-continued

```
aactgcaaat tatgtgggtt tattcctct                                    509
```

<210> SEQ ID NO 104
<211> LENGTH: 464
<212> TYPE: DNA
<213> ORGANISM: Medicago truncatula

<400> SEQUENCE: 104

```
ttcttacaag ttatcatggc tcgttcagtt cctttggttt ccaccatctt tgtcttcctt     60
ctgcttcttg tggccactgg gccaagtatg gtgggagaag caagaacttg tgagtcacaa    120
agtcacaaat tcaaagggcc atgtgctagt gatcacaact gtgcttctgt gtgccaaaca    180
gaacgtttct ctggaggaca ctgccgtgga ttccgtcgta gatgcttttg cactacacat    240
tgttaaatac atgtttaaga aattaatccc tatatgctaa gaaaaaaaag atgatggatc    300
catcaccttt ttctacttgt tcatgttttg gaataaagct agctagctat ccattttatt    360
atgggtttct ttctatcttt gtctttttt  taatgtcttg ttatagatct ttcgatcgta    420
cgagtagaag tgaatgaaat gaagaatatc atgtgtgttc tctc                     464
```

<210> SEQ ID NO 105
<211> LENGTH: 47
<212> TYPE: PRT
<213> ORGANISM: Medicago truncatula

<400> SEQUENCE: 105

```
Arg Thr Cys Glu Ser Gln Ser His Lys Phe Lys Gly Pro Cys Ala Ser
1               5                   10                  15

Asp His Asn Cys Ala Ser Val Cys Gln Thr Glu Arg Phe Phe Gly Gly
            20                  25                  30

His Cys Arg Gly Phe Arg Arg Arg Cys Phe Cys Thr Thr His Cys
        35                  40                  45
```

<210> SEQ ID NO 106
<211> LENGTH: 19
<212> TYPE: DNA
<213> ORGANISM: Medicago truncatula

<400> SEQUENCE: 106

```
atggtggcag aagcaagaa                                                  19
```

<210> SEQ ID NO 107
<211> LENGTH: 18
<212> TYPE: DNA
<213> ORGANISM: Medicago truncatula

<400> SEQUENCE: 107

```
caaaagatct acggacgg                                                   18
```

<210> SEQ ID NO 108
<211> LENGTH: 401
<212> TYPE: DNA
<213> ORGANISM: Medicago truncatula

<400> SEQUENCE: 108

```
atggctcgtt cagttccttt ggtttccacc atctttgtct tccttctgct tcttgtggcc     60
actggtgagt agtgtttctt tatccttaat ctaacaccat catgtctttg tttactcaat    120
taaccagttt atatcttgac aaaatctcaa ttaacatagt catagtataa tccataatat    180
ttctttattt tgatatagaa ttgttgttaa ttgattttgt gatatatggt atagggccaa    240
```

```
gtatggtggc agaagcaaga acttgtgagt cacaaagtca caaattcaaa gggccatgtg      300
ctagtgatca caactgtgct tctgtgtgcc aaacagaacg tttctctgga ggacactgcc      360
gtggattccg tcgtagatgc ttttgcacta cacattgtta a                          401

<210> SEQ ID NO 109
<211> LENGTH: 475
<212> TYPE: DNA
<213> ORGANISM: Medicago truncatula

<400> SEQUENCE: 109
atggctcgtt cagttccttt ggtttccacc atctttgtct ttttcttct tattgtggcc       60 actggtgggt gcaatttctt gatgcttaat taatttacaa catcattttg ttgttgatct     120
caattactaa ctaactttag tcgctattat agcacactta cattccataa tgtaatccat     180
aattgtgttt aatgtttatt tatttcacaa atccaaatct agtgcaattt gatttccttt     240
tattattatt ttttgcatga aagtattatt aatttacttg tgtttttgat ctgtgatatg     300
gacagaaatg gggccaagta tggtagcagc aaggacttgt gagactccaa gtaacagctt     360
caaaggagca tgcttcagtg acaccaattg tgcttctgtg tgccaaactg agggtttccc     420
tggaggacac tgcaaaggct tccgtcagag atgcttttgc actacacatt gttaa          475

<210> SEQ ID NO 110
<211> LENGTH: 506
<212> TYPE: DNA
<213> ORGANISM: Medicago truncatula

<400> SEQUENCE: 110
atggctcgtt cagttccttt ggtttccacc atctttgttt ttttcttct tcttgtggcc       60 actggtgggg tctaatttct tgatgcttaa ttaatttaca acattttttt tttttttgtt     120
gatctcaatt aactaatttt agtttctaca attgtgttta atattttgtt gatctcaatt     180
tttttgttga gctcaataat tgtgtttaat atttatttat ttcacaaatc taactctagt     240
ctgatttgat ttccgtttat ttatttttatt tgttatttta tgtttgaatg aatttgtaat    300
ttacttgtgt tgttgatttt gtgatatgga cagagatggg gccaattatg gtggcagaag    360
caaggacttg tgagactcca gtaacaact tcaaaggact atgtgtgagt gacaccaatt     420
gtgcttctgt gtgccaaact gagggttttc ctggaggaca ctgcgaaggc ttccgtcaga    480
gatgcttttg cactacacat tgttaa                                         506

<210> SEQ ID NO 111
<211> LENGTH: 76
<212> TYPE: PRT
<213> ORGANISM: Medicago truncatula

<400> SEQUENCE: 111

Met Ala Arg Ser Val Pro Leu Val Ser Thr Ile Phe Val Phe Leu Leu
1               5                   10                  15

Leu Leu Val Ala Thr Gly Pro Ser Met Val Ala Glu Ala Arg Thr Cys
            20                  25                  30

Glu Ser Gln Ser His Lys Phe Lys Gly Pro Cys Ala Ser Asp His Asn
        35                  40                  45

Cys Ala Ser Val Cys Gln Thr Glu Arg Phe Ser Gly Gly His Cys Arg
    50                  55                  60

Gly Phe Arg Arg Arg Cys Phe Cys Thr Thr His Cys
65                  70                  75
```

<210> SEQ ID NO 112
<211> LENGTH: 47
<212> TYPE: PRT
<213> ORGANISM: Medicago truncatula

<400> SEQUENCE: 112

Arg Thr Cys Glu Ser Gln Ser His Lys Phe Lys Gly Pro Cys Ala Ser
1               5                   10                  15

Asp His Asn Cys Ala Ser Val Cys Gln Thr Glu Arg Phe Ser Gly Gly
            20                  25                  30

His Cys Arg Gly Phe Arg Arg Cys Phe Cys Thr Thr His Cys
        35                  40                  45

<210> SEQ ID NO 113
<211> LENGTH: 77
<212> TYPE: PRT
<213> ORGANISM: Medicago truncatula

<400> SEQUENCE: 113

Met Ala Arg Ser Val Pro Leu Val Ser Thr Ile Phe Val Phe Phe Leu
1               5                   10                  15

Leu Ile Val Ala Thr Glu Met Gly Pro Ser Met Val Ala Ala Arg Thr
            20                  25                  30

Cys Glu Thr Pro Ser Asn Ser Phe Lys Gly Ala Cys Phe Ser Asp Thr
        35                  40                  45

Asn Cys Ala Ser Val Cys Gln Thr Glu Gly Phe Pro Gly Gly His Cys
    50                  55                  60

Glu Gly Phe Arg Gln Arg Cys Phe Cys Thr Thr His Cys
65                  70                  75

<210> SEQ ID NO 114
<211> LENGTH: 47
<212> TYPE: PRT
<213> ORGANISM: Medicago truncatula

<400> SEQUENCE: 114

Arg Thr Cys Glu Thr Pro Ser Asn Ser Phe Lys Gly Ala Cys Phe Ser
1               5                   10                  15

Asp Thr Asn Cys Ala Ser Val Cys Gln Thr Glu Gly Phe Pro Gly Gly
            20                  25                  30

His Cys Glu Gly Phe Arg Gln Arg Cys Phe Cys Thr Thr His Cys
        35                  40                  45

<210> SEQ ID NO 115
<211> LENGTH: 78
<212> TYPE: PRT
<213> ORGANISM: Medicago truncatula

<400> SEQUENCE: 115

Met Ala Arg Ser Val Pro Leu Val Ser Thr Ile Phe Val Phe Phe Leu
1               5                   10                  15

Leu Leu Val Ala Thr Glu Met Gly Pro Ile Met Val Ala Glu Ala Arg
            20                  25                  30

Thr Cys Glu Thr Pro Ser Asn Asn Phe Lys Gly Leu Cys Val Ser Asp
        35                  40                  45

Thr Asn Cys Ala Ser Val Cys Gln Thr Glu Gly Phe Pro Gly Gly His
    50                  55                  60

Cys Glu Gly Phe Arg Gln Arg Cys Phe Cys Thr Thr His Cys
65                  70                  75

```
<210> SEQ ID NO 116
<211> LENGTH: 47
<212> TYPE: PRT
<213> ORGANISM: Medicago truncatula

<400> SEQUENCE: 116

Arg Thr Cys Glu Thr Pro Ser Asn Asn Phe Lys Gly Leu Cys Val Ser
1               5                   10                  15

Asp Thr Asn Cys Ala Ser Val Cys Gln Thr Glu Gly Phe Pro Gly Gly
            20                  25                  30

His Cys Glu Gly Phe Arg Gln Arg Cys Phe Cys Thr Thr His Cys
        35                  40                  45

<210> SEQ ID NO 117
<211> LENGTH: 29
<212> TYPE: PRT
<213> ORGANISM: Medicago truncatula

<400> SEQUENCE: 117

Met Ala Arg Ser Val Pro Leu Val Ser Thr Ile Phe Val Phe Leu Leu
1               5                   10                  15

Leu Leu Val Ala Thr Gly Pro Ser Met Val Ala Glu Ala
            20                  25

<210> SEQ ID NO 118
<211> LENGTH: 29
<212> TYPE: PRT
<213> ORGANISM: Medicago truncatula

<400> SEQUENCE: 118

Met Ala Arg Ser Val Pro Leu Val Ser Thr Ile Phe Val Phe Leu Leu
1               5                   10                  15

Leu Leu Val Ala Thr Gly Pro Ser Met Val Ala Glu Ala
            20                  25

<210> SEQ ID NO 119
<211> LENGTH: 30
<212> TYPE: PRT
<213> ORGANISM: Medicago truncatula

<400> SEQUENCE: 119

Met Ala Arg Ser Val Pro Leu Val Ser Thr Ile Phe Val Phe Phe Leu
1               5                   10                  15

Leu Ile Val Ala Thr Glu Met Gly Pro Ser Met Val Ala Ala
            20                  25                  30

<210> SEQ ID NO 120
<211> LENGTH: 31
<212> TYPE: PRT
<213> ORGANISM: Medicago truncatula

<400> SEQUENCE: 120

Met Ala Arg Ser Val Pro Leu Val Ser Thr Ile Phe Val Phe Phe Leu
1               5                   10                  15

Leu Leu Val Ala Thr Glu Met Gly Pro Ile Met Val Ala Glu Ala
            20                  25                  30

<210> SEQ ID NO 121
<211> LENGTH: 29
<212> TYPE: PRT
<213> ORGANISM: Medicago truncatula
```

<400> SEQUENCE: 121

Met Ala Arg Ser Val Phe Leu Val Ser Thr Ile Phe Val Phe Leu Leu
1               5                   10                  15

Val Leu Val Ala Thr Gly Pro Ser Met Val Ala Glu Ala
            20                  25

<210> SEQ ID NO 122
<211> LENGTH: 29
<212> TYPE: PRT
<213> ORGANISM: Medicago truncatula

<400> SEQUENCE: 122

Met Ala Arg Ser Val Ser Leu Val Phe Thr Ile Phe Val Phe Leu Leu
1               5                   10                  15

Leu Val Val Ala Thr Gly Pro Ser Met Val Ala Glu Ala
            20                  25

<210> SEQ ID NO 123
<211> LENGTH: 29
<212> TYPE: PRT
<213> ORGANISM: Medicago truncatula

<400> SEQUENCE: 123

Met Ala Arg Ser Val Pro Leu Val Ser Thr Ile Phe Val Phe Leu Leu
1               5                   10                  15

Leu Leu Val Ala Thr Gly Pro Ser Met Val Gly Glu Ala
            20                  25

<210> SEQ ID NO 124
<211> LENGTH: 234
<212> TYPE: DNA
<213> ORGANISM: Medicago truncatula

<400> SEQUENCE: 124
atggctcgtt cagttccttt ggtttccacc atctttgtct tttttcttct tattgtggcc      60
actgaaatgg ggccaagtat ggtagcagca aggacttgtg agactccaag taacagcttc     120
aaaggagcat gcttcagtga caccaattgt gcttctgtgt gccaaactga gggtttccct     180
ggaggacact gcaaaggctt ccgtcagaga tgcttttgca ctacacattg ttaa           234

<210> SEQ ID NO 125
<211> LENGTH: 47
<212> TYPE: PRT
<213> ORGANISM: Medicago truncatula

<400> SEQUENCE: 125

Arg Thr Cys Glu Ser Gln Ser His Lys Phe Lys Gly Pro Cys Ala Ser
1               5                   10                  15

Asp His Asn Cys Ala Ser Val Cys Gln Thr Glu Arg Phe Ser Gly Gly
            20                  25                  30

Arg Cys Arg Gly Phe Arg Arg Arg Cys Phe Cys Thr Thr His Cys
        35                  40                  45

<210> SEQ ID NO 126
<211> LENGTH: 231
<212> TYPE: DNA
<213> ORGANISM: Medicago truncatula

<400> SEQUENCE: 126
atggctcgtt cagttccttt ggtttccacc atctttgtct tccttctgct tcttgtggcc      60

```
actgggccaa gtatggtggc agaagcaaga acttgtgagt cacaaagtca caaattcaaa        120
gggccatgtg ctagtgatca caactgtgct tctgtgtgcc aaacagaacg tttctctgga        180
ggacactgcc gtggattccg tcgtagatgc ttttgcacta cacattgtta a                 231
```

<210> SEQ ID NO 127
<211> LENGTH: 42
<212> TYPE: DNA
<213> ORGANISM: Artificial Sequence
<220> FEATURE:
<223> OTHER INFORMATION: Primer sequence

<400> SEQUENCE: 127

```
ctcgagaaaa gaagaacttc tgagtcacaa agtcacaaat tc                            42
```

<210> SEQ ID NO 128
<211> LENGTH: 32
<212> TYPE: DNA
<213> ORGANISM: Artificial Sequence
<220> FEATURE:
<223> OTHER INFORMATION: Primer sequence

<400> SEQUENCE: 128

```
ttcaaagggc catctgctag tgatcacaac tg                                       32
```

<210> SEQ ID NO 129
<211> LENGTH: 35
<212> TYPE: DNA
<213> ORGANISM: Artificial Sequence
<220> FEATURE:
<223> OTHER INFORMATION: Primer sequence

<400> SEQUENCE: 129

```
gctagtgatc acaactctgc ttctgtgtgc caaac                                    35
```

<210> SEQ ID NO 130
<211> LENGTH: 30
<212> TYPE: DNA
<213> ORGANISM: Artificial Sequence
<220> FEATURE:
<223> OTHER INFORMATION: Primer sequence

<400> SEQUENCE: 130

```
caactgtgct tctgtgtccc aaacagaacg                                          30
```

<210> SEQ ID NO 131
<211> LENGTH: 39
<212> TYPE: DNA
<213> ORGANISM: Artificial Sequence
<220> FEATURE:
<223> OTHER INFORMATION: Primer sequence

<400> SEQUENCE: 131

```
tgcttttgca ctacacattc ttaagaattc ccctagggc                                39
```

<210> SEQ ID NO 132
<211> LENGTH: 25
<212> TYPE: DNA
<213> ORGANISM: Artificial Sequence
<220> FEATURE:
<223> OTHER INFORMATION: Primer sequence

<400> SEQUENCE: 132

```
ctggaggacg ctcccgtgga ttccg                                               25
```

<210> SEQ ID NO 133
<211> LENGTH: 35
<212> TYPE: DNA
<213> ORGANISM: Artificial Sequence
<220> FEATURE:
<223> OTHER INFORMATION: Primer sequence

<400> SEQUENCE: 133
ggattccgtc gtagatcctt ttgcactaca cattg                          35

<210> SEQ ID NO 134
<211> LENGTH: 35
<212> TYPE: DNA
<213> ORGANISM: Artificial Sequence
<220> FEATURE:
<223> OTHER INFORMATION: Primer sequence

<400> SEQUENCE: 134
ccgtcgtaga tgcttttcca ctacacattg ttaag                          35

<210> SEQ ID NO 135
<211> LENGTH: 47
<212> TYPE: PRT
<213> ORGANISM: Artificial Sequence
<220> FEATURE:
<223> OTHER INFORMATION: Mature MtDef4.1 (H33R,C3S,C47S) peptide
      sequence

<400> SEQUENCE: 135

Arg Thr Ser Glu Ser Gln Ser His Lys Phe Lys Gly Pro Cys Ala Ser
1               5                   10                  15

Asp His Asn Cys Ala Ser Val Cys Gln Thr Glu Arg Phe Ser Gly Gly
            20                  25                  30

Arg Cys Arg Gly Phe Arg Arg Arg Cys Phe Cys Thr Thr His Ser
        35                  40                  45

<210> SEQ ID NO 136
<211> LENGTH: 47
<212> TYPE: PRT
<213> ORGANISM: Artificial Sequence
<220> FEATURE:
<223> OTHER INFORMATION: Mature MtDef4.1(H33R,C14S,C34S) peptide
      sequence

<400> SEQUENCE: 136

Arg Thr Cys Glu Ser Gln Ser His Lys Phe Lys Gly Pro Ser Ala Ser
1               5                   10                  15

Asp His Asn Cys Ala Ser Val Cys Gln Thr Glu Arg Phe Ser Gly Gly
            20                  25                  30

Arg Ser Arg Gly Phe Arg Arg Arg Cys Phe Cys Thr Thr His Cys
        35                  40                  45

<210> SEQ ID NO 137
<211> LENGTH: 47
<212> TYPE: PRT
<213> ORGANISM: Artificial Sequence
<220> FEATURE:
<223> OTHER INFORMATION: Mature MtDef4.1(H33R,C20S,C41S) peptide
      sequence

<400> SEQUENCE: 137

Arg Thr Cys Glu Ser Gln Ser His Lys Phe Lys Gly Pro Cys Ala Ser
1               5                   10                  15

Asp His Asn Ser Ala Ser Val Cys Gln Thr Glu Arg Phe Ser Gly Gly

```
                    20                  25                  30
Arg Cys Arg Gly Phe Arg Arg Arg Ser Phe Cys Thr Thr His Cys
         35                  40                  45

<210> SEQ ID NO 138
<211> LENGTH: 47
<212> TYPE: PRT
<213> ORGANISM: Artificial Sequence
<220> FEATURE:
<223> OTHER INFORMATION: Mature MtDef4.1(H33R,C24S,C43S) peptide
      sequence

<400> SEQUENCE: 138

Arg Thr Cys Glu Ser Gln Ser His Lys Phe Lys Gly Pro Cys Ala Ser
1               5                   10                  15

Asp His Asn Cys Ala Ser Val Ser Gln Thr Glu Arg Phe Ser Gly Gly
                20                  25                  30

Arg Cys Arg Gly Phe Arg Arg Arg Cys Phe Ser Thr Thr His Cys
         35                  40                  45

<210> SEQ ID NO 139
<211> LENGTH: 38
<212> TYPE: DNA
<213> ORGANISM: Artificial Sequence
<220> FEATURE:
<223> OTHER INFORMATION: Primer sequence

<400> SEQUENCE: 139
agaaaagaag aacttgtgag tcacaaagtc acaaattc                             38

<210> SEQ ID NO 140
<211> LENGTH: 45
<212> TYPE: DNA
<213> ORGANISM: Artificial Sequence
<220> FEATURE:
<223> OTHER INFORMATION: Primer sequence

<400> SEQUENCE: 140
gattacgaat tcttaacaat gtgtagtgca aaagcatcta cgacg                     45

<210> SEQ ID NO 141
<211> LENGTH: 593
<212> TYPE: DNA
<213> ORGANISM: Artificial Sequence
<220> FEATURE:
<223> OTHER INFORMATION: MtDef4 TC94214 consensus sequence

<400> SEQUENCE: 141
atttaaggca agctagttgc atgtgtattt tcacttaaaa ttctacacta tagttctctt     60
tttttcttac aagttatcat ggctcgttca gttcctttgg tttccaccat ctttgtcttc    120
cttctgcttc ttgtggccac tgggccaagt atggtggcag aagcaagaac ttgtgagtca    180
caaagtcaca aattcaaagg gccatgtgct agtgatcaca actgtgcttc tgtgtgccaa    240
acagaacgtt tctctggagg acactgccgt ggattccgtc gtagatgctt ttgcactaca    300
cattgttaaa tacatgttta agaaattaat ccctatatgc taagaaaaaa aagatgatgg    360
atccatcacc ttttctact tgttcatgtt tggaataaa gctagctagc tatccatttt     420
attatgggtt tctttctatc tttgtctttt ttttaatgtc ttgttataga tctttcgatc    480
gtacgagtag aagtgaatga atgaagaat atcatgtgtg ttctctcaaa caatctttga    540
tcatatcaaa ctgcaaatta tgtgggttta ttcctctaat aaatccgagt tat           593
```

<210> SEQ ID NO 142
<211> LENGTH: 231
<212> TYPE: DNA
<213> ORGANISM: Medicago sativa

<400> SEQUENCE: 142

```
atggctcgtt cagttccttt ggtttccacc atctttgtct tccttctgct tcttgtggcc      60
actgggccaa gtatggtggc agaagcaagg acttgtgagt cacaaagtca caaattcaaa     120
gggccatgtg ctagtgatca caactgtgct tctgtgtgcc aaacagaacg tttctctgga     180
ggacactgcc gtggattccg tcgtagatgc ttttgcacta cacattgtta a              231
```

<210> SEQ ID NO 143
<211> LENGTH: 237
<212> TYPE: DNA
<213> ORGANISM: Medicago truncatula

<400> SEQUENCE: 143

```
atggctcgtt cagttccttt ggtttccacc atctttgttt tttttcttct tcttgtggcc      60
actgagatgg ggccaattat ggtggcagaa gcaaggactt gtgagactcc aagtaacaac     120
ttcaaaggac tatgtgtgag tgacaccaat gtgcttctg tgtgccaaac tgagggtttt     180
cctggaggac actgcgaagg cttccgtcag agatgctttt gcactacaca ttgttaa       237
```

<210> SEQ ID NO 144
<211> LENGTH: 144
<212> TYPE: DNA
<213> ORGANISM: Medicago truncatula

<400> SEQUENCE: 144

```
agaacttgtg agtcacaaag tcacaaattc aaagggccat gtgctagtga tcacaactgt      60
gcttctgtgt gccaaacaga acgtttctct ggaggacgct gccgtggatt ccgtcgtaga     120
tgcttttgca ctacacattg ttaa                                             144
```

<210> SEQ ID NO 145
<211> LENGTH: 1727
<212> TYPE: DNA
<213> ORGANISM: Artificial Sequence
<220> FEATURE:
<223> OTHER INFORMATION: Pichia expression vector sequence

<400> SEQUENCE: 145

```
ctgaaaaata acagttatta ttcgagatct aacatccaaa gacgaaaggt tgaatgaaac      60
cttttttgcca tccgacatcc acaggtccat tctcacacat aagtgccaaa cgcaacagga    120
ggggatacac tagcagcaga ccgttgcaaa cgcaggacct ccactcctct tctcctcaac    180
acccactttt gccatcgaaa aaccagccca gttattgggc ttgattggag ctcgctcatt    240
ccaattcctt ctattaggct actaacacca tgactttatt agcctgtcta tcctggcccc    300
cctggcgagg ttcatgtttg tttatttccg aatgcaacaa gctccgcatt acacccgaac    360
atcactccag atgagggctt tctgagtgtg ggtcaaata gtttcatgtt ccccaaatgg    420
cccaaaactg acagtttaaa cgctgtcttg aacctaata tgacaaaagc gtgatctcat    480
ccaagatgaa ctaagtttgg ttcgttgaaa tgctaacggc cagttggtca aaagaaact    540
tccaaaagtc gccataccgt ttgtcttgtt tggtattgat tgacgaatgc tcaaaaataa    600
tctcattaat gcttagcgca gtctctctat cgcttctgaa ccccggtgca cctgtgccga    660
aacgcaaatg gggaaacacc cgcttttttgg atgattatgc attgtctcca cattgtatgc    720
```

```
ttccaagatt ctggtgggaa tactgctgat agcctaacgt tcatgatcaa aatttaactg      780
ttctaacccc tacttgacag caatatataa acagaaggaa gctgccctgt cttaaacctt      840 ttttttatc atcattatta gcttactttc ataattgcga ctggttccaa ttgacaagct       900
tttgatttta acgacttta acgacaactt gagaagatca aaaacaact aattattcga        960 aggatccaaa cgatgagatt tccttcaatt tttactgcag ttttattcgc agcatcctcc     1020
gcattagctg ctccagtcaa cactacaaca gaagatgaaa cggcacaaat tccggctgaa     1080
gctgtcatcg gttactcaga tttagaaggg gatttcgatg ttgctgtttt gccattttcc     1140
aacagcacaa ataacgggtt attgtttata aatactacta ttgccagcat tgctgctaaa     1200
gaagaagggg tatctcgaga aaagaagaac ttgtgagtca caaagtcaca aattcaaagg     1260
gccatgtgct agtgatcaca actgtgcttc tgtgtgccaa acagaacgtt tctctggagg     1320
acactgccgt ggattccgtc gtagatgctt tgcactaca cattgttaag aattccctag      1380
ggcggccgcg aattaattcg ccttagacat gactgttcct cagttcaagt tgggcactta     1440
cgagaagacc ggtcttgcta gattctaatc aagaggatgt cagaatgcca tttgcctgag     1500
agatgcaggc ttcattttg atacttttt atttgtaacc tatatagtat aggattttt       1560 ttgtcatttt gtttcttctc gtacgagctt gctcctgatc agcctatctc gcagctgatg     1620
aatatcttgt ggtaggggtt tgggaaaatc attcgagttt gatgttttc ttggtatttc     1680 ccactcctct tcagagtaca gaagattaag tgagaagttc gtttgtg                   1727

<210> SEQ ID NO 146
<211> LENGTH: 144
<212> TYPE: DNA
<213> ORGANISM: Artificial Sequence
<220> FEATURE:
<223> OTHER INFORMATION: A mature MtDef4.1(H33R,C3S,C47S) coding
      sequence

<400> SEQUENCE: 146
agaacttctg agtcacaaag tcacaaattc aaagggccat gtgctagtga tcacaactgt      60
gcttctgtgt gccaaacaga acgtttctct ggaggacgct gccgtggatt ccgtcgtaga     120
tgcttttgca ctacacattc ttaa                                            144

<210> SEQ ID NO 147
<211> LENGTH: 144
<212> TYPE: DNA
<213> ORGANISM: Artificial Sequence
<220> FEATURE:
<223> OTHER INFORMATION: A mature MtDef4.1(H33R,C14S,C34S) coding
      sequence

<400> SEQUENCE: 147
agaacttgtg agtcacaaag tcacaaattc aaagggccat ctgctagtga tcacaactgt      60
gcttctgtgt gccaaacaga acgtttctct ggaggacgct cccgtggatt ccgtcgtaga     120
tgcttttgca ctacacattg ttaa                                            144

<210> SEQ ID NO 148
<211> LENGTH: 144
<212> TYPE: DNA
<213> ORGANISM: Artificial Sequence
<220> FEATURE:
<223> OTHER INFORMATION: A mature MtDef4.1(H33R,C20S,C41S) coding
      sequence

<400> SEQUENCE: 148
```

```
agaacttgtg agtcacaaag tcacaaattc aaagggccat gtgctagtga tcacaactct    60
gcttctgtgt gccaaacaga acgtttctct ggaggacgct gccgtggatt ccgtcgtaga   120
tccttttgca ctacacattg ttaa                                          144
```

<210> SEQ ID NO 149
<211> LENGTH: 144
<212> TYPE: DNA
<213> ORGANISM: Artificial Sequence
<220> FEATURE:
<223> OTHER INFORMATION: A mature MtDef4.1(H33R,C24S,C43S) coding
      sequence

<400> SEQUENCE: 149

```
agaacttgtg agtcacaaag tcacaaattc aaagggccat gtgctagtga tcacaactgt    60
gcttctgtgt cccaaacaga acgtttctct ggaggacgct gccgtggatt ccgtcgtaga   120
tgcttttcca ctacacattg ttaa                                          144
```

<210> SEQ ID NO 150
<211> LENGTH: 3736
<212> TYPE: DNA
<213> ORGANISM: Artificial Sequence
<220> FEATURE:
<223> OTHER INFORMATION: DNA construct for expression of MtDef4
      proteins in plants
<220> FEATURE:
<221> NAME/KEY: misc_feature
<222> LOCATION: (1110)..(1110)
<223> OTHER INFORMATION: n is a, c, g, or t

<400> SEQUENCE: 150

```
caaaatattt agcagcattc cagattgggt tcaatcaaca aggtacgagc catatcactt    60
tattcaaatt ggtatcgcca aaaccaagaa ggaactccca tcctcaaagg tttgtaagga   120
agaattctca gtccaaagcc tcaacaaggt cagggtacag agtctcccaaa ccattagcca   180 aaagctacag gagatcaatg aagaatcttc aatcaaagta aactactgtt ccagcacatg   240
catcatggtc agtaagtttc agaaaaagac atccaccgaa gacttaaagt tagtgggcat   300 cttttgaaagt aatcttgtca acatcgagca gctggcttgt ggggaccaga caaaaaagga   360
atggtgcaga attgttaggc gcacctacca aaagcatctt tgcctttatt gcaaagataa   420
agcagattcc tctagtacaa gtggggaaca aaataacgtg gaaagagct gtcctgacag   480 cccactcact aatgcgtatg acgaacgcag tgacgaccac aaaagaattc cctctatata   540
agaaggcatt cattcccatt tgaaggatca tcagatactg aaccaatatt gataattccg   600
atattctcag agagcttttc attcaaaggt atggagtttt gaagggcttt actcttaaca   660 tttgttttc tttgtaaatt gttaatggtg gtttctgtgg gggaagaatc ttttgccagg   720
tccttttggg tttcgcatgt ttatttgggt tattttctc gactatggct gacattacta   780
gggctttcgt gctttcatct gtgttttctt cccttaatag gtctgtctct ctggaatatt   840
taattttcgt atgtaagtta tgagtagtcg ctgtttgtaa taggctcttg tctgtaaagg   900
tttcagcagg tgtttgcgtt ttattgcgtc atgtgtttca gaaggccttt gcagattatt   960
gcgttgtact ttaatatttt gtctccaacc ttgttatagt ttccctcctt tgatctcaca  1020 ggaaccctt cttctttgag cattttcttg tggcgttctg tagtaatatt ttaattttgg  1080
gcccgggttc tgagggtagg tgattattcn cagtgatgtg ctttccctat aaggtcctct  1140
atgtgtaagc tgttagggtt tgtgcgttac tattgacatg tcacatgtca catatttcct  1200
```

```
tcctcttatc cttcgaactg atggttcttt ttctaattcg tggattgctg gtgccatatt    1260
ttatttctat tgcaactgta ttttagggtg tctctttctt tttgatttct tgttaatatt    1320
tgtgttcagg ttgtaactat gggttgctag ggtgtctgcc ctcttctttt gtgcttcttt    1380
cgcagaatct gtccgttggt ctgtatttgg gtgatgaatt atttattcct tgaagtatct    1440
gtctaattag cttgtgatga tgtgcaggta tattcgttag tcatatttca aggatccaaa    1500
accatggctc gttcagttcc tttggtttcc accatctttg tcttccttct gcttcttgtg    1560
gccactggtg agtagtgttt ctttatcctt aatctaacac catcatgtct ttgtttactc    1620
aattaaccag tttatatctt gacaaaatct caattaacat agtcatagta taatccataa    1680
tatttcttta ttttgatata gaattgttgt taattgattt tgtgatatat ggtatagggc    1740
caagtatggt ggcagaagca agaacttgtg agtcacaaag tcacaaattc aaagggccat    1800
gtgctagtga tcacaactgt gcttctgtgt gccaaacaga acgtttctct ggaggacact    1860
gccgtggatt ccgtcgtaga tgcttttgca ctacacattg taaggatgaa ctttaagagc    1920
tccgaatttc cccgatcgtt caaacatttg gcaataaagt ttcttaagat tgaatcctgt    1980
tgccggtctt gcgatgatta tcatataatt tctgttgaat tacgttaagc atgtaataat    2040
taacatgtaa tgcatgacgt tatttatgag atgggttttt atgattagag tcccgcaatt    2100
atacatttaa tacgcgatag aaaacaaaat atagcgcgca aactaggata aattatcgcg    2160
cgcggtgtca tctatgttac tagatcgcaa ttggatctcc ctgcaggcgc gccttaatta    2220
agcggccgcg gtaccgggcc cccctcgag gtcgacggta tcgataagct tcacgctgcc    2280
gcaagcactc agggcgcaag ggctgctaaa ggaagcggaa cacgtagaaa gccagtccgc    2340
agaaacggtg ctgaccccgg atgaatgtca gctactgggc tatctggaca agggaaaacg    2400
caagcgcaaa gagaaagcag gtagcttgca gtgggcttac atggcgatag ctagactggg    2460
cggttttatg gacagcaagc gaaccggaat tgccagctgg ggcgccctct ggtaaggttg    2520
ggaagccctg caaagtaaac tggatggctt tcttgccgcc aaggatctga tggcgcaggg    2580
gatcaagatc atgagcggag aattaaggga gtcacgttat gacccccgcc gatgacgcgg    2640
gacaagccgt tttacgtttg gaactgacag aaccgcaacg ttgaaggagc cactcagccg    2700
cgggtttctg gagtttaatg agctaagcac atacgtcaga aaccattatt gcgcgttcaa    2760
aagtcgccta aggtcactat cagctagcaa atatttcttg tcaaaaatgc tccactgacg    2820
ttccataaat tcccctcggt atccaattag agtctcatat tcactctcaa tccagatctc    2880
gactctaggg ggatctacca tgagcccaga acgacgcccg gccgacatcc gccgtgccac    2940
cgaggcggac atgccggcgg tctgcaccat cgtcaaccac tacatcgaga caagcacggt    3000
caacttccgt accgagccgc aggaaccgca ggagtggacg gacgacctcg tccgtctgcg    3060
ggagcgctat ccctggctcg tcgccgaggt ggacggcgag gtcgccggca tcgcctacgc    3120
gggcccctgg aaggcacgca acgcctacga ctggacggcc gagtcgaccg tgtacgtctc    3180
cccccgccac cagcggacgg gactgggctc cacgctctac acccacctgc tgaagtccct    3240
ggaggcacag ggcttcaaga gcgtggtcgc tgtcatcggg ctgcccaacg acccgagcgt    3300
gcgcatgcac gaggcgctcg gatatgcccc ccgcggcatg ctgcgggcgg ccggcttcaa    3360
gcacgggaac tggcatgacg tgggtttctg gcagctggac ttcagcctgc cggtgccgcc    3420
ccgtccggtc ctgcccgtca ccgagatctg atgacccta gaggatcagc tcgaatttcc    3480
ccgatcgttc aaacatttgg caataaagtt tcttaagatt gaatcctgtt gccggtcttg    3540
cgatgattat catataattt ctgttgaatt acgttaagca tgtaataatt aacatgtaat    3600
```

-continued

```
gcatgacgtt atttatgaga tgggttttta tgattagagt cccgcaatta tacatttaat    3660
acgcgataga aaacaaaata tagcgcgcaa actaggataa attatcgcgc gcggtgtcat    3720
ctatgttact agatcg                                                    3736
```

<210> SEQ ID NO 151
<211> LENGTH: 76
<212> TYPE: PRT
<213> ORGANISM: Medicago truncatula

<400> SEQUENCE: 151

```
Met Ala Arg Ser Val Pro Leu Val Ser Thr Ile Phe Val Phe Leu Leu
1               5                   10                  15

Leu Leu Val Ala Thr Gly Pro Ser Met Val Ala Glu Ala Arg Thr Cys
            20                  25                  30

Glu Ser Gln Ser His Lys Phe Lys Gly Pro Cys Ala Ser Asp His Asn
        35                  40                  45

Cys Ala Ser Val Cys Gln Thr Glu Arg Phe Ser Gly Gly Arg Cys Arg
    50                  55                  60

Gly Phe Arg Arg Arg Cys Phe Cys Thr Thr His Cys
65                  70                  75
```

<210> SEQ ID NO 152
<211> LENGTH: 37
<212> TYPE: PRT
<213> ORGANISM: Medicago truncatula

<400> SEQUENCE: 152

```
Arg Thr Cys Glu Ser Gln Ser His Lys Phe Lys Gly Pro Cys Ala Ser
1               5                   10                  15

Asp His Asn Ser Ala Ser Val Cys Gln Thr Glu Arg Phe Ser Gly Gly
            20                  25                  30

Arg Cys Arg Gly Phe
        35
```

<210> SEQ ID NO 153
<211> LENGTH: 36
<212> TYPE: PRT
<213> ORGANISM: Medicago truncatula

<400> SEQUENCE: 153

```
Ser His Lys Phe Lys Gly Pro Cys Ala Ser Asp His Asn Ser Ala Ser
1               5                   10                  15

Val Cys Gln Thr Glu Arg Phe Ser Gly Gly Arg Cys Arg Gly Phe Arg
            20                  25                  30

Arg Arg Ser Phe
        35
```

<210> SEQ ID NO 154
<211> LENGTH: 37
<212> TYPE: PRT
<213> ORGANISM: Medicago truncatula

<400> SEQUENCE: 154

```
Thr Cys Glu Ser Gln Ser His Lys Phe Lys Gly Pro Cys Ala Ser Asp
1               5                   10                  15

His Asn Ser Ala Ser Val Cys Gln Thr Glu Arg Phe Ser Gly Gly Arg
            20                  25                  30

Cys Arg Gly Phe Arg
```

-continued

```
                            35

<210> SEQ ID NO 155
<211> LENGTH: 37
<212> TYPE: PRT
<213> ORGANISM: Medicago truncatula

<400> SEQUENCE: 155

Arg Thr Cys Glu Ser Gln Ser His Lys Phe Lys Gly Pro Cys Ala Ser
1               5                   10                  15

Asp His Asn Cys Ala Ser Val Ser Gln Thr Glu Arg Phe Ser Gly Gly
            20                  25                  30

Arg Cys Arg Gly Phe
        35

<210> SEQ ID NO 156
<211> LENGTH: 37
<212> TYPE: PRT
<213> ORGANISM: Medicago truncatula

<400> SEQUENCE: 156

Thr Cys Glu Ser Gln Ser His Lys Phe Lys Gly Pro Cys Ala Ser Asp
1               5                   10                  15

His Asn Cys Ala Ser Val Ser Gln Thr Glu Arg Phe Ser Gly Gly Arg
            20                  25                  30

Cys Arg Gly Phe Arg
        35
```